United States Patent

Takeuchi et al.

Patent Number: 6,033,554
Date of Patent: Mar. 7, 2000

[54] CORROSION RESISTANCE TEST PROCESS FOR TEST MATERIAL COMPRISED OF METAL BLANK AND COATING FILM

[75] Inventors: Toshihiro Takeuchi; Tadashi Imanaka; Kazunori Takikawa; Katsuyoshi Kaneko, all of Wako, Japan

[73] Assignee: Honda Giken Kogyo Kabushiki Kaisha, Tokyo, Japan

[21] Appl. No.: 08/945,310

[22] PCT Filed: Jun. 10, 1997

[86] PCT No.: PCT/JP97/01999

§ 371 Date: Dec. 22, 1997

§ 102(e) Date: Dec. 22, 1997

[87] PCT Pub. No.: WO97/47961

PCT Pub. Date: Dec. 18, 1997

[30] Foreign Application Priority Data

Jun. 10, 1996 [JP] Japan ................................. 8-147035

[51] Int. Cl.$^7$ .................................................. G01N 27/26
[52] U.S. Cl. ........................ 205/791; 204/404; 204/434; 205/776.5
[58] Field of Search .................................... 204/404, 434; 205/775.5, 776.5, 777, 791, 791.5

[56] References Cited

U.S. PATENT DOCUMENTS

| | | | |
|---|---|---|---|
| 3,223,598 | 12/1965 | Jacky et al. .............................. | 204/434 |
| 3,660,249 | 5/1972 | Townsend ................................ | 204/404 |
| 3,840,439 | 10/1974 | Marsh ..................................... | 204/404 |
| 4,294,667 | 10/1981 | Yamamoto et al. ..................... | 204/404 |
| 4,425,193 | 1/1984 | Taylor ..................................... | 204/404 |
| 5,076,906 | 12/1991 | DerMarderosian ..................... | 205/791 |

FOREIGN PATENT DOCUMENTS

| | | |
|---|---|---|
| 5-107218 | 4/1993 | Japan . |
| 5-281179 | 10/1993 | Japan . |
| 7-195612 | 8/1995 | Japan . |
| 7-234202 | 9/1995 | Japan . |

*Primary Examiner*—T. Tung
*Attorney, Agent, or Firm*—Nikaido, Marmelstein, Murray & Oram LLP

[57] ABSTRACT

A process for promoting corrosion of a test material, is provided including the steps of immersing, in an electrolytic liquid, a test material which is comprised of a metal blank and a coating film formed on the metal blank, and allowing a DC current to flow between the metal blank and an electrode in the electrolytic liquid while reversing the polarity of the metal blank alternately from positive to negative and vice versa, thereby causing the coating film to be at least partly peeled off the metal blank in one state of polarity and promoting corrosion of the metal blank in the reversed state of polarity. The process may also be conducted with a metal blank having a damaged portion of the coating film which exposes a portion of the surface of the metal blank underlying the coating film.

13 Claims, 52 Drawing Sheets

FIG.45
(a)
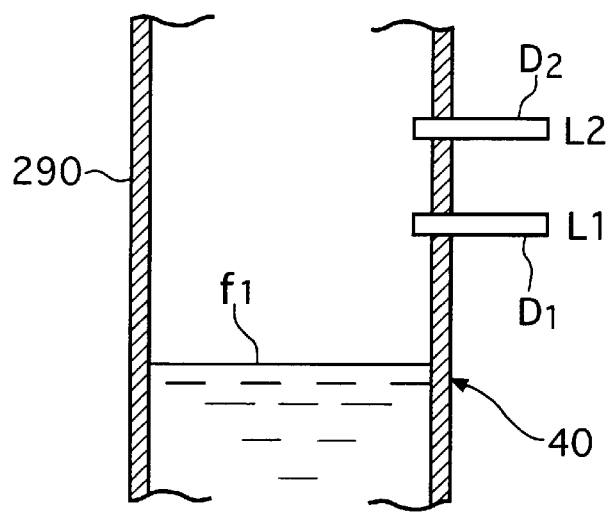
(b)
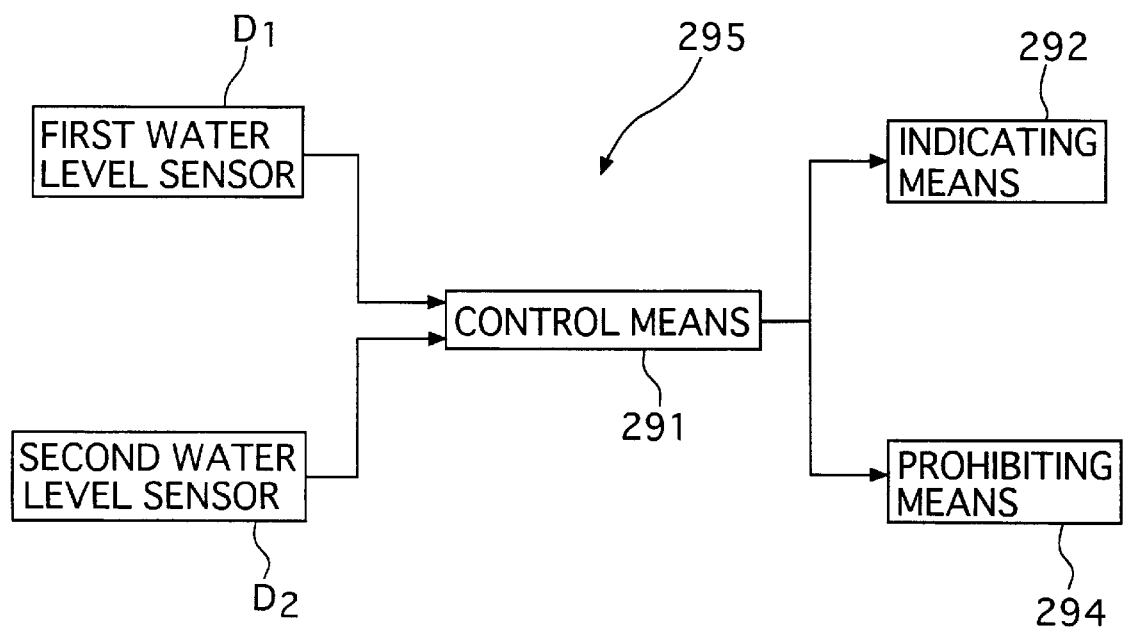

CORROSION RESISTANCE TEST PROCESS FOR TEST MATERIAL COMPRISED OF METAL BLANK AND COATING FILM

FIELD OF THE INVENTION

The present invention relates to a corrosion resistance test process for a test material comprised of a metal blank and a coating film formed on the metal blank, and an electrolytic test machine used for the corrosion resistance test.

BACKGROUND ART

A cathode peel-off test process is conventionally known as a test process for examining an adhesion force of the coating film of such a test material (for example, see Japanese Patent Application Laid-open No.7-195612).

In this test process, a procedure is employed which involves immersing a test material having a damaged portion formed on the coating film to reach the metal blank, into an aqueous solution of NaCl serving as an electrolytic liquid, and allowing a DC current to flow between the metal blank serving as a cathode and an electrode provided in the aqueous solution of NaCl.

During supplying the electric current, OH ion produced by the electrolysis of water on the side of the metal blank as the cathode causes the adhesion force of the coating film to the metal blank to be decreased from a starting point provided by the damaged portion of the coating film, thereby promoting the peeling-off and blistering of the coating film. In this way, the cathode peel-off test process has an advantage that the superiority and inferiority of the adhesion force of the coating film can be simply determined. However, corrosion of the metal blank accompanying the peeling-off of the coating film cannot be predicted, and the cathode peel-off test process suffers from a problem that the overall estimation of the corrosion resistance cannot be carried out for the test material.

Therefore, a cycle corrosion test (CCT) is employed which is capable of simultaneously estimating the deterioration of the coating film and the corrosion of the metal blank.

However, the cycle corrosion test is accompanied by a problem that it requires a lot of test time and for this reason, a test result cannot be obtained early.

DISCLOSURE OF THE INVENTION

It is an object of the present invention to provide a corrosion resistance test process of the above-described type, which is capable of simultaneously estimating the peeling-off of the coating film and the corrosion of the metal blank, and in which the test time can be shortened.

To achieve the above object, according to the present invention, there is provided a corrosion resistance test process for a test material, comprising the steps of immersing, into an electrolytic liquid, a test material which is comprised of a metal blank and a coating film formed on the metal blank and which has a damaged portion extending to reach the metal blank, and allowing a DC current to flow between the metal blank and an electrode in an electrolytic liquid, while the polarity of the metal blank is alternately switched over from positive to negative polarity or vice versa.

In the above test process, when the polarity of the metal blank is negative, a coating film peeling-off step is carried out. On the other hand, when the polarity of the metal blank is positive, a metal blank corroding step, namely an anode oxidation step is carried out. By alternately repeating the coating film peeling-off and the anode oxidation in the above manner, the peeling-off of the coating film and the corrosion of the metal blank from the starting point provided by the damaged portion can be promoted, thereby performing an overall estimation of the corrosion within a short time.

The above test process is also applied to a test material which does not have a damaged portion as described above. In this case, a thinner portion of the coating film, a pin hole or the like serves as a starting point for the peeling-off of the coating film and the corrosion of the metal blank.

It is another object of the present invention to provide an electrolytic test machine which is suitable for carrying out the above-described corrosion resistance test process.

To achieve the above object, according to the present invention, there is provided an electrolytic test machine used for a corrosion resistance test of a test material comprised of a metal blank and a coating film formed on the metal blank, comprising an electrolytic cell in which an electrolytic liquid is stored, an electrode immersed in the electrolytic liquid, a DC power source for supplying an electric current to between the electrode and the metal blank of the test material immersed in the electrolytic liquid, and a polarity switch-over means provided in energizing lines between the electrode and the metal blank as well as the DC power source for alternately switching over the polarity of the metal blank from positive to negative polarity or vice versa.

With this electrolytic test machine, it is possible to carry out the above-described corrosion resistance test process easily.

BRIEF DESCRIPTION OF THE DRAWINGS

FIG. 45(a) is a diagram for explaining the positions of water level sensors disposed in the abnormal-point detector in the exhaust system;

FIG. 45(b) is a block diagram of the abnormal-point detector in the exhaust system;

BEST MODE FOR CARRYING OUT THE INVENTION

[A] Summary of Electrolytic Test Machine

Figure 1:
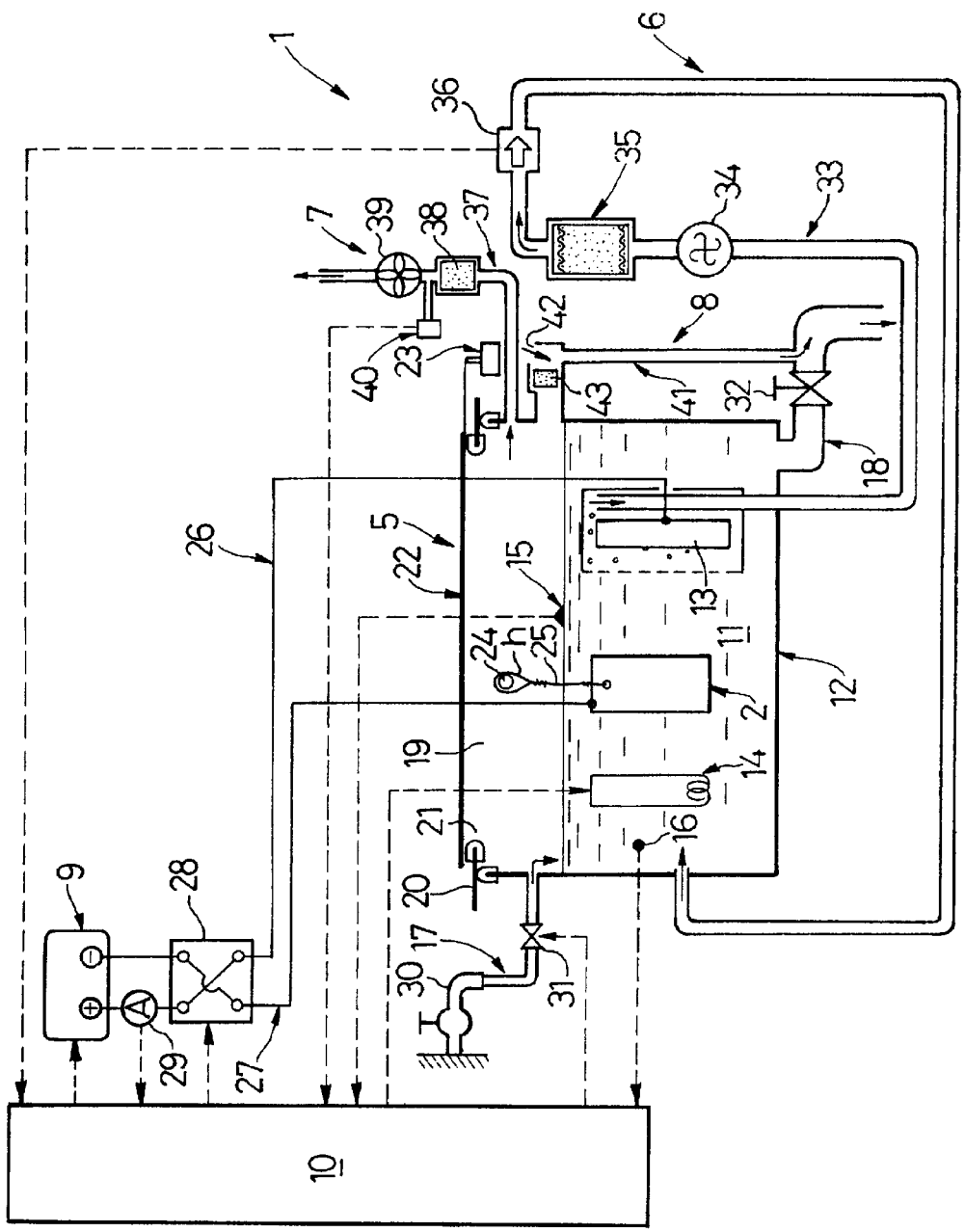
FIG. 1 is a diagrammatic illustration of an electrolytic test machine according to an embodiment of the present invention.
Figure 2:
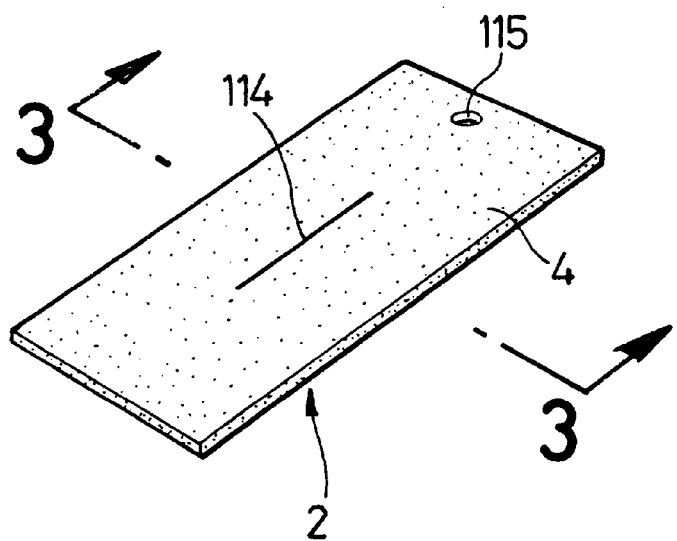
FIG. 2 is a perspective view of a test material.
Figure 3:
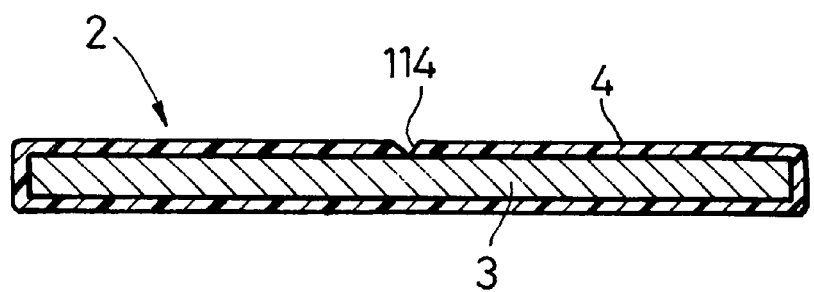
FIG. 3 is a sectional view taken along a line 3—3 in FIG. 2.

An electrolytic test machine 1 shown in FIG. 1 is used for a corrosion resistance test for a test material 2 shown in FIGS. 2 and 3, which is comprised of a steel plate 3 as a metal blank, and a coating film 4 formed on the entire steel plate 3.

The electrolytic test machine 1 includes an electrolytic device 5. A harmful gas treating device 6, an exhaust device 7 and an overflow device 8 having a sucking function are mounted to the electrolytic device 5.

The electrolytic device 5 includes a DC power source (a constant-voltage power source having a maximum voltage of 20 V and a maximum current of 50 A) 9, a computer programmed control unit 10, an electrolytic cell 12 in which an aqueous solution of NaCl 11 as an electrolytic liquid is stored, a plate-like carbon electrode 13 which is a consumable electrode as an electrolytic electrode immersed in the aqueous solution of NaCl 11, an electric heater 14, a water level sensor 15, a temperature sensor 16, a water supply pipe line 17 and a drainage pipe line 18.

Because the aqueous solution of NaCl 11 is used as the electrolytic liquid, a chlorine gas as a harmful gas is generated with the electrolysis of the aqueous solution of NaCl 11 during a test. To cope with this, an upward opening 19 in the electrolytic cell 12 is covered and sealed with a cover 20 made of a synthetic resin. An upward opening 21 in the cover 20 is used for placing and removing the test material 2 into and out of the electrolytic cell 12 and sealed with openable and closable lid 22 upon closing thereof. The lid 22 and cover 20 tightly close the electrolytic cell 12.

An electric power cylinder 23 which is a drive source for opening and closing the lid 22 is supplied with electric current from an external power source.

The test material 2 is hung from a support bar 24 in the electrolytic cell 12 through a string 25 made of a synthetic resin, and is immersed into the aqueous solution of NaCl 11. The carbon electrode 13 and the steel plate 3 of the test material 2 are connected to the DC power source 9 through energizing lines 26 and 27. A polarity switch-over relay 28 as a polarity switch-over means is connected to the energizing lines 26 and 27. An ammeter 29 is connected to one of the energizing lines 27 between the DC power source 9 and the polarity switch-over relay 28.

The DC power source 9 is controlled at a constant voltage by the control unit 10 and also controlled in an ON/OFF manner. The polarity switch-over relay 28 is controlled by the control unit 10, so that the polarity of the steel plate 3 of the test material 2 is alternately switched over from the positive to the negative or vice versa. In this case, the polarity of the carbon electrode 13 is, of course, opposite from that of the steel plate 3. The ammeter 29 inputs an electric current flowing across the carbon electrode 13 and the steel plate 3 to the control unit 10.

The water supply pipe line 17 communicates at one end thereof with a cock 30 of a water service which is a water supply source and at the other end with the electrolytic cell 12. A solenoid valve 31 is mounted at an intermediate portion of the water supply pipe line 17. The opening and closing of the solenoid valve 31 are controlled through the control unit 10 by a detection signal from the water level sensor 15. The drainage pipe line 18 communicates with a bottom of the electrolytic cell 12 and includes a manual cock 32.

The electric heater 14 is supplied with an electric current from the external power source and controlled in an ON/OFF manner through the control unit 10 by detection signals from the water level sensor 15 and the temperature sensor 16.

The chlorine gas treating device 6 as the harmful gas treating device includes a treating pipe line 33 extending from the electrolytic cell 12. An electric suction pump 34, a chlorine gas (harmful gas) purifying device 35 and an abnormal-point detecting flow rate sensor 36 are mounted in the treating pipe line 33. The suction pump 34 is supplied with an electric current from the external power source.

The exhaust device 7 includes an exhaust pipeline 37 extending from the electrolytic cell 12. A chlorine gas (harmful gas) adsorbing member 38, an electric exhaust fan 39 and a detecting means 40 for detecting an abnormality generation are provided in the exhaust pipe line 37. The exhaust fan 39 is supplied with an electric current from the external power source.

The overflow device 8 having the sucking function is comprised of an overflow pipe 41 extending from the electrolytic cell 12, a gas intake port 42 provided in the overflow pipe 41, and a chlorine gas (harmful gas) adsorbing member 43 disposed in an inlet of the overflow pipe 41.

[B] Entire structure of Electrolytic Test Machine (FIGS. 4 to 9)

The electrolytic test machine 1 is constructed into a movable type, wherein this side thereof as viewed in FIGS. 4 to 6, 8 and 9 is a front portion X. Therefore, testing personnel conducts a testing operation from the side of the front portion X.

As shown in FIGS. 5 to 9, the electrolytic test machine 1 includes a rectangular machine base 44. A plurality of casters 45 as traveling wheels are mounted on a lower surface of the machine base 44 at four corners thereof, respectively, in the illustrated embodiment. If the direction a of movement of the machine base 44 is a lengthwise direction, namely, a lateral direction, a tracking/urging hook 46 is provided on opposite outer end faces of the machine base 44 as viewed in the direction a of movement of the machine base 44, namely, on left and right outer end faces.

Figure 7:
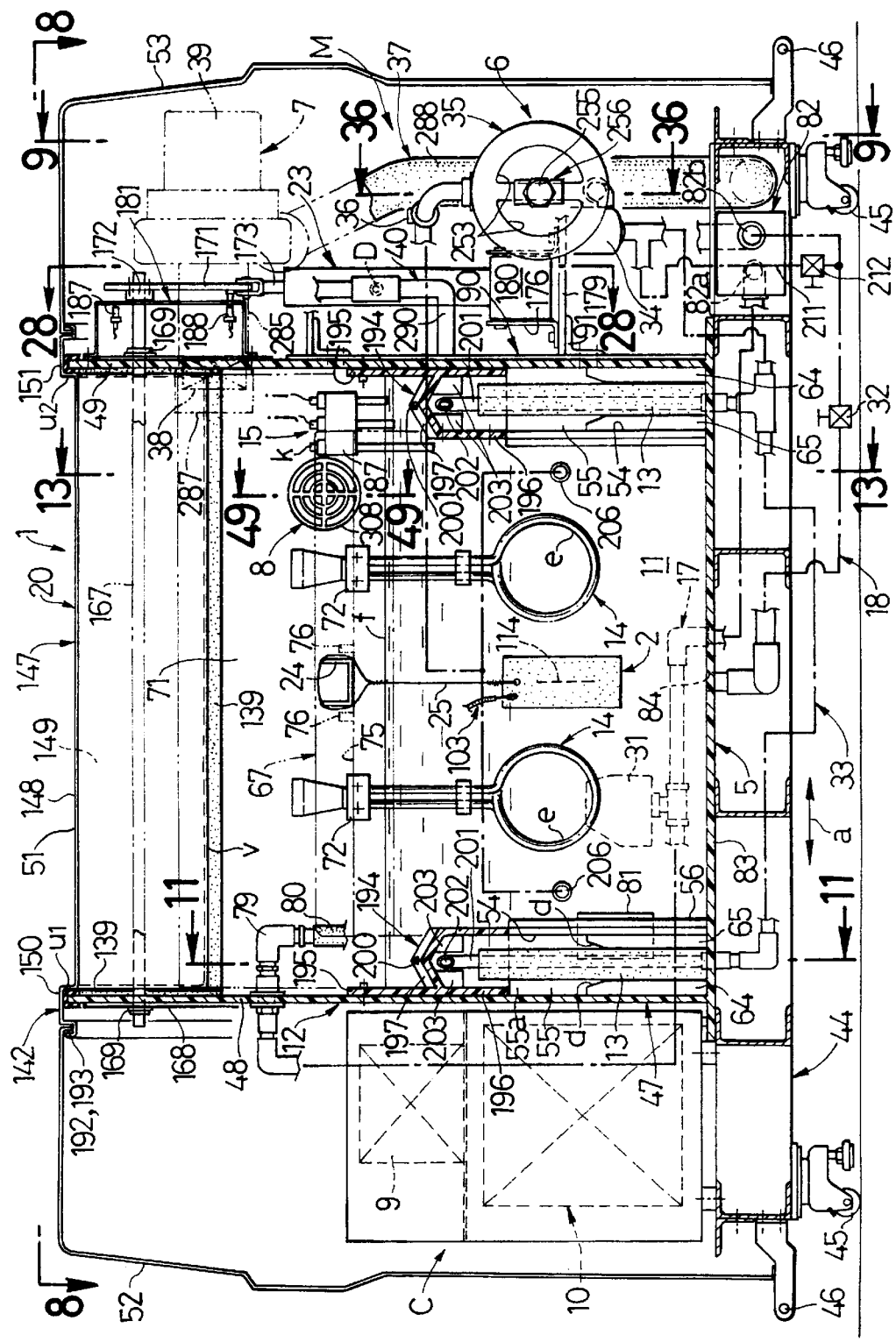
FIG. 7 is a vertical sectional front view of the electrolytic test machine, which corresponds to a sectional view taken along a line 7—7 in FIG. 6.
Figure 8:
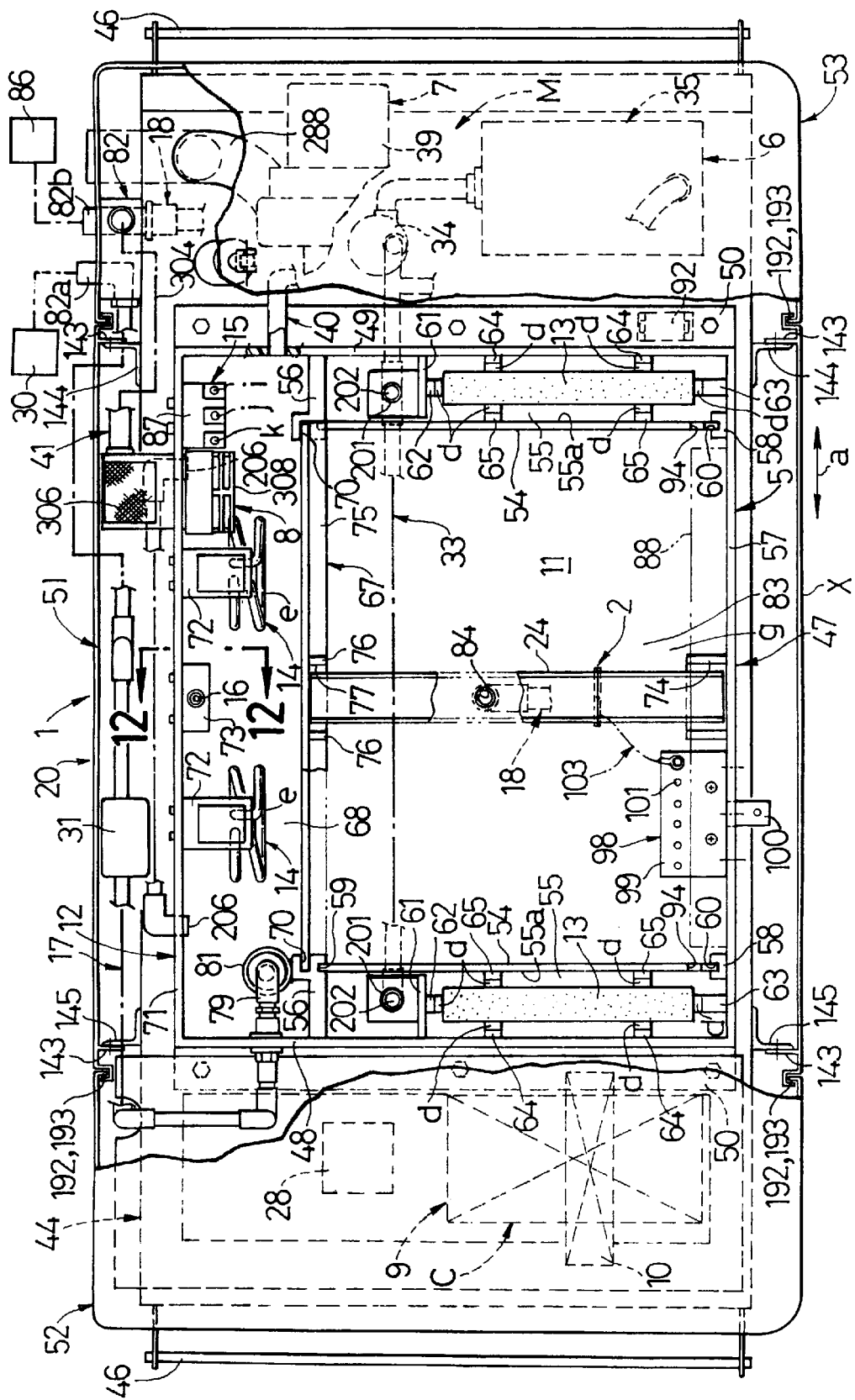
FIG. 8 is a cutaway plan view of an essential portion of the electrolytic test machine, which corresponds to a sectional view taken along a line 8—8 in FIG. 7.

A mechanical section M is disposed on the machine base 44 on one end side, i.e., on the right side as viewed in FIGS. 7 and 8 along the direction a of movement; the box-like electrolytic cell 12 made of a synthetic resin is disposed at a central portion of the machine base 44; and a control section C is disposed on the machine base 44 on the other end side, i.e., on the left side as viewed in FIGS. 7 and 8.

The electrolytic cell 12 is detachably mounted to the machine base 44 through a pair of mounting plates 50 protruding from lower ends of outer surfaces of left and right sidewall portions 48 and 49 of a peripheral wall 47, as shown in FIGS. 7 and 8.

The electrolytic cell 12, the mechanical section M and the control section C are covered respectively with a central cover section 51, a left cover section 52 and a right cover section 53 which constitute the cover 20 made of a synthetic resin. The central cover section 51 covering the electrolytic cell 12 seals the upward opening 19 in the electrolytic cell 12, and has the upward rectangular opening 21 which is used for placing and removing the test material 2 into and out of the electrolytic cell 12. The lid 22 for opening and closing the opening 21 has a hinge on the side of one end thereof, namely, on the side of a rear portion thereof.

Figure 9:
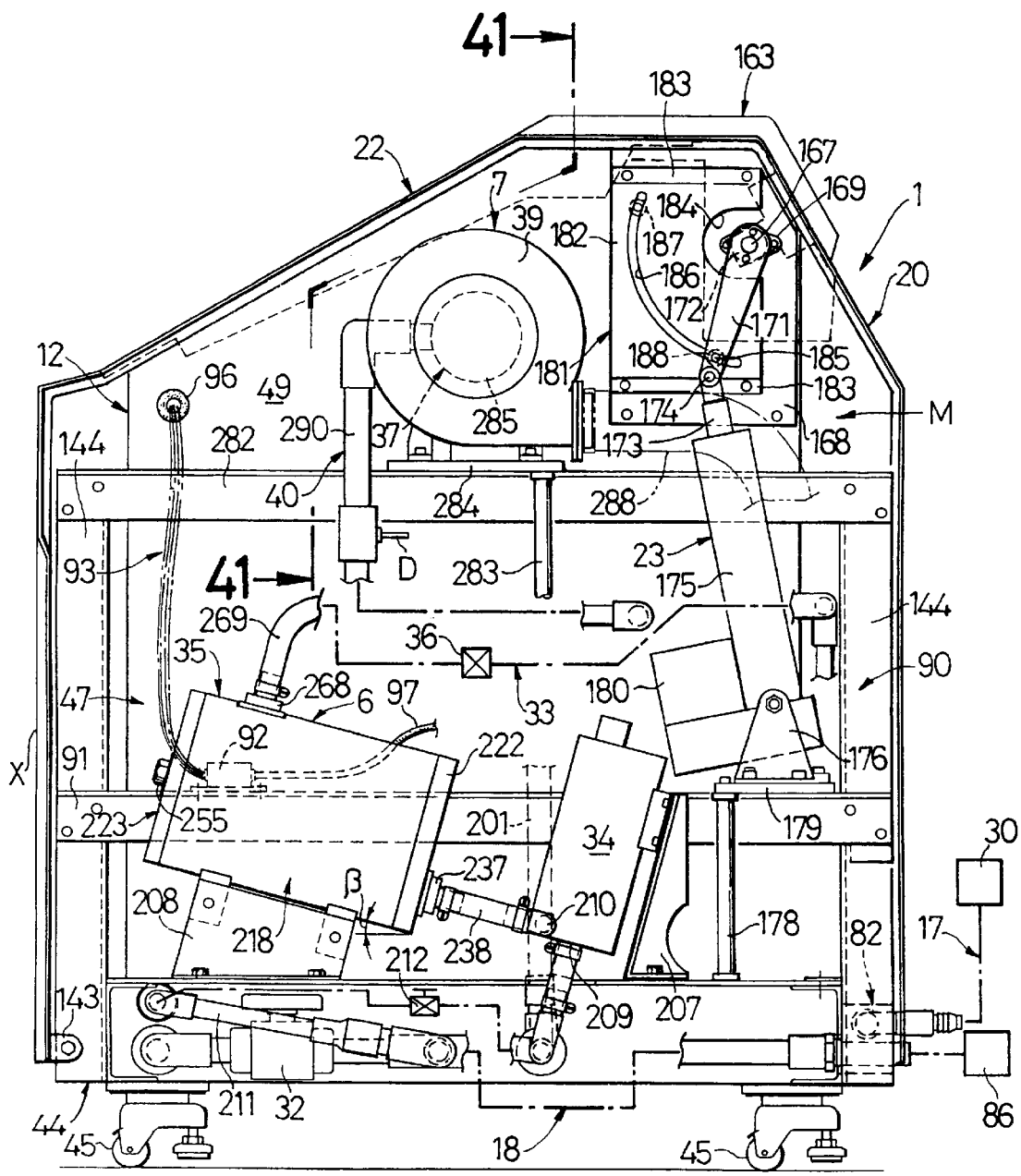
FIG. 9 is a sectional view taken along a line 9—9 in FIG. 7.

As best shown in FIGS. 7 and 9, included in the mechanical section M are the electric power cylinder 23 which is the drive source for opening and closing the lid 22, the suction pump 34 and the chlorine gas purifying device 35 in the chlorine gas treating device 6, the exhaust fan 39 of the exhaust device 7, and the like.

In addition, as best shown in FIGS. 7 and 8, included in the control section C are transformers (not shown), various switches and the like for the suction pump 34 and the exhaust fan 39, in addition to the DC power source 9, the computer programmed control unit 10 and the polarity switch-over relay 28.

With such construction, the electrolytic cell 12 is independent from the mechanical section M and the control section C. Therefore, it is possible to sufficiently increase the volume of the electrolytic cell 12, thereby moderating the limitation for the size of the test material 2.

The electrolytic cell 12, the mechanical section M and the control section C are independent from one another, leading to a good workability of maintenance for them.

Further, the electrolytic test machine 1 is of a movable type and therefore, it is possible to easily perform transportation of the test machine 1 into and out of a test room.

Moreover, the relatively large-sized and heavy electrolytic cell 12 is disposed at the central area and therefore, the electrolytic test machine 1 can be moved with a good balance.

Figure 6:
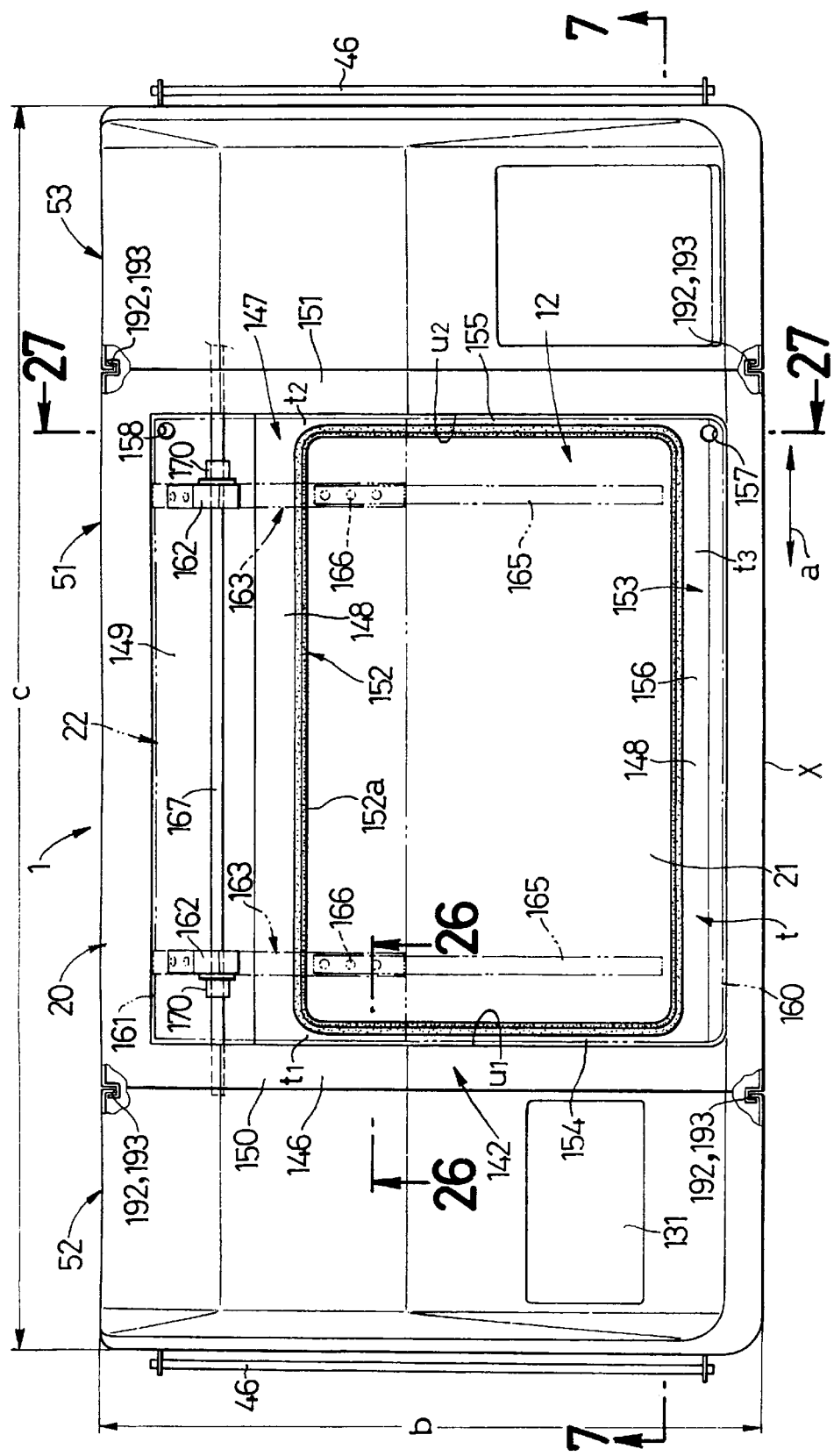
FIG. 6 is a view taken along an arrow 6 in FIG. 5.

Yet further, the electrolytic cell 12, the mechanical section M and the control section C are disposed in a line in the direction a of movement of the electrolytic test machine 1 and therefore, the width dimension perpendicular to the direction a of movement can be easily adjusted to the width dimension of an access port of a ready-made test room. For example, the width b in the electrolytic test machine 1 is set at 800 mm, and the length c in the direction a of movement is set at 1,600 mm, as shown in FIG. 6.

[C] Structure of Disposition of Carbon Electrode and Electric Heater (FIGS. 7, 8 and 10 to 13)

In a left and lower area within the electrolytic cell 12, an electrode chamber 55 is defined so as to become immersed into the aqueous solution of NaCl 11, by the peripheral wall 47 of the electrolytic cell 12, and a partition plate 54 which is opposed to and in proximity to an inner surface of the peripheral wall 47 and which is attachable to and detachable from the electrolytic cell 12.

The left sidewall portion 48 of the peripheral wall 47 has a division plate 56 made of a synthetic resin, which forms a rear wall of the electrode chamber 55. A front wall portion 57 of the peripheral wall 47 has a projection 58 which forms a front wall of the electrode chamber 55 and is opposed to the division plate 56. The partition plate 54 is slidably fitted into opposed guide grooves 59 and 60 in the division plate 56 and the projection 58. Therefore, the partition plate 54 forms a right sidewall of the electrode chamber 55, while the left sidewall portion 48 forms a left sidewall of the electrode chamber 55.

The plate-like carbon electrode 13 is accommodated within the electrode chamber 55 in a standing state and in parallel to the partition plate 54. An upper portion of the carbon electrode 13 protrudes above the top end of the partition plate 54. Front and rear end faces of the carbon electrode 13 are clamped by a clamping member 62 of a protruding plate 61 of the left sidewall portion 48 and by a clamping member 63 of the front wall portion 57. The left and right flat sides of the carbon electrode 13 are clamped by a pair of clamping members 64 of the left sidewall portion 48 and a pair of clamping members 65 of the partition plate 54. The carbon electrode 13 is capable of being set in and withdrawn from between the clamping members 62 to 65, and in order to guide the insertion of the electrode 13, a slope d is formed on an upper portion of each of the clamping members on the insertion side of the electrode. The partition plate 54 has a large number of through-holes 66 at locations opposed to the carbon electrode 13 for permitting the aqueous solution of NaCl 11 to be passed therethrough.

In a right lower area within the electrolytic cell 12, another electrode chamber 55 similar to the above-described electrode chamber 55 is defined utilizing the right sidewall portion 49 of the peripheral wall 47, and another plate-like carbon electrode 13 similar to the above-described electrode 13 is accommodated in the another electrode chamber 55. Thus, the distribution of voltage in the test material 2 can be made uniform. Components of the right electrode chamber 55 similar to those of the left electrode chamber 55 are designated by the like reference characters.

In a rear area within the electrolytic cell 12, a heater chamber 68 is defined by the peripheral wall 47 of the electrolytic cell 12 and a partition plate 67 which is opposed to and in proximity to the inner surface of the peripheral wall 47 and which is attachable to and detachable from the electrolytic cell 12. The partition plate 67 has a plurality of through-holes 69 for permitting the aqueous solution of NaCl 11 to be passed therethrough, and is slidably fitted into opposed guide grooves defined in the pair of division plates 56 of both the electrode chambers 55. Therefore, a front wall of the heater chamber 68 is formed by the partition plate 67 and the pair of division plates 56; a rear wall of the heater chamber 68 is formed by a rear wall portion 71 of the peripheral wall 47 and further, left and right sidewalls of the heater chamber 68 are formed by the left and right sidewall portions 48 and 49.

As best shown in FIGS. 7, 8, 12 and 13, the pair of electric heaters 14 are accommodated within the heater chamber 68 at a predetermined distance in left and right directions and with their coiled portions e turned downwards. An upper portion of each of the electric heaters 14 is supported by a support 72 mounted on the rear wall portion 71 above the liquid level f of the aqueous solution of NaCl 11. The temperature sensor 16 for detecting the temperature of the aqueous solution of NaCl 11 is disposed between both the electric heaters 14. The temperature sensor 16 has a lower end portion immersed in the aqueous solution of NaCl 11, and an upper portion supported by a support 73 mounted on the rear wall portion 71 above the liquid level f.

Within the electrolytic cell 12, an area surrounded by the three partition plates 54 and 67 and the front wall portion 57 is used as a space g for placement of the test material 2.

Figure 13:
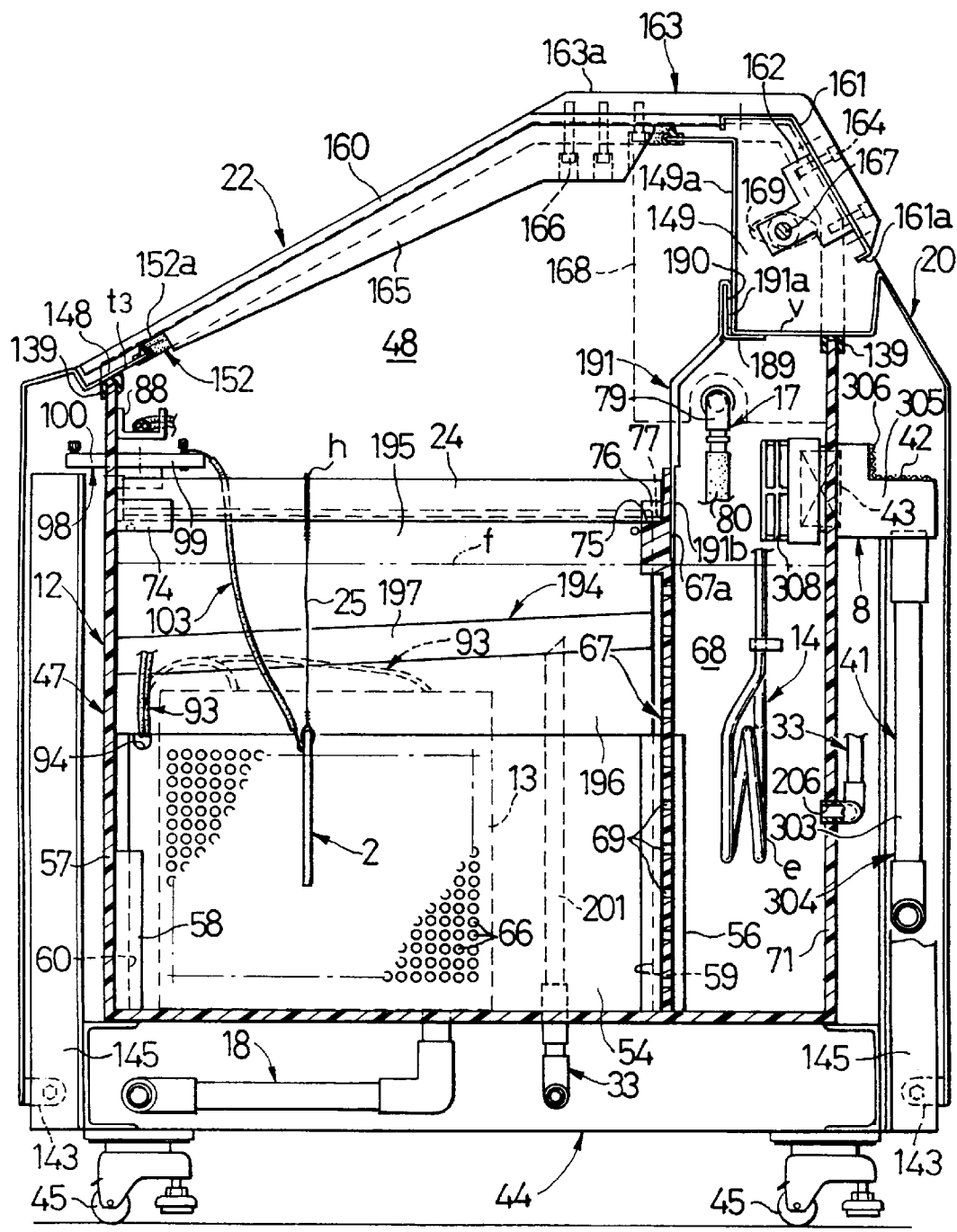
FIG. 13 is a sectional view taken along a line 13—13 in FIG. 7.

As shown in FIGS. 7, 8 and 13, in the space i, a U-shaped support 74 is projectingly provided on an inner surface of the front wall portion 57, so that it is located above the liquid level f of the aqueous solution of NaCl 11 and at laterally intermediate portion. A recess 77 is defined by a pair of protrusions 76 located at a stepped portion 75 of the partition plate 67 adjacent to the heater chamber 68, so that it is opposed to the support 74. The test material supporting bar 24 made of a synthetic resin and having a channel-like shape is detachably suspended between the U-shaped support 74 and the recess 77. As shown in FIGS. 1 and 13, the test material 2 is immersed into the aqueous solution of NaCl 11 in such a manner that it is hung from the supporting bar 24 through a looped portion h of the string 25 of a synthetic resin attached to the test material 2.

If both the carbon electrodes 13 and both the electric heaters 14 are accommodated within the electrode chambers 55 and the heater chambers 68, respectively as described above, the contact of the electrodes 13 and the electric heaters 14 with the test material 2 can be reliably prevented, and both the carbon electrodes 13 and both the electric heaters 14 can be protected. Each of the partition plates 54 and 67 are in proximity to the peripheral wall 47 of the electrolytic cell 12 and moreover, each of the electrode chamber 55 and the heater chamber 68 use a portion of the peripheral wall 47 as a portion of the chamber wall. Therefore, the space g for placement of the test material 2 can be made wider, as compared with a case where another partition plate is used in place of the peripheral wall 47. Further, each of the partition plates 54 and 67 can be removed from the electrolytic cell 12 and as a result, each of the carbon electrodes 13 can be also removed from the electrolytic cell 12. Therefore, the partition plates 54 and 67 and the carbon electrodes 13 cannot become obstacles in carrying out the maintenance, for example, in washing the inside of the electrolytic cell 12, leading to a good workability of the maintenance. Moreover, each of the carbon electrodes 13 is clamped by the peripheral wall 47 and the partition plate 54 and therefore, the structure of supporting the carbon electrode 13 is simple and firm. Further, each of the electric heaters 14 is attached to the fixed peripheral wall 47 and therefore, the structure of attaching the electric heater 14 is firm. The three partition plates 54 and 67 may be formed into a ⊐-shaped integral configuration.

[D] Water-supply and Discharge Structure of Electrolytic Cell (FIGS. 7, 8, 10, 13 and 14)

Figure 10:
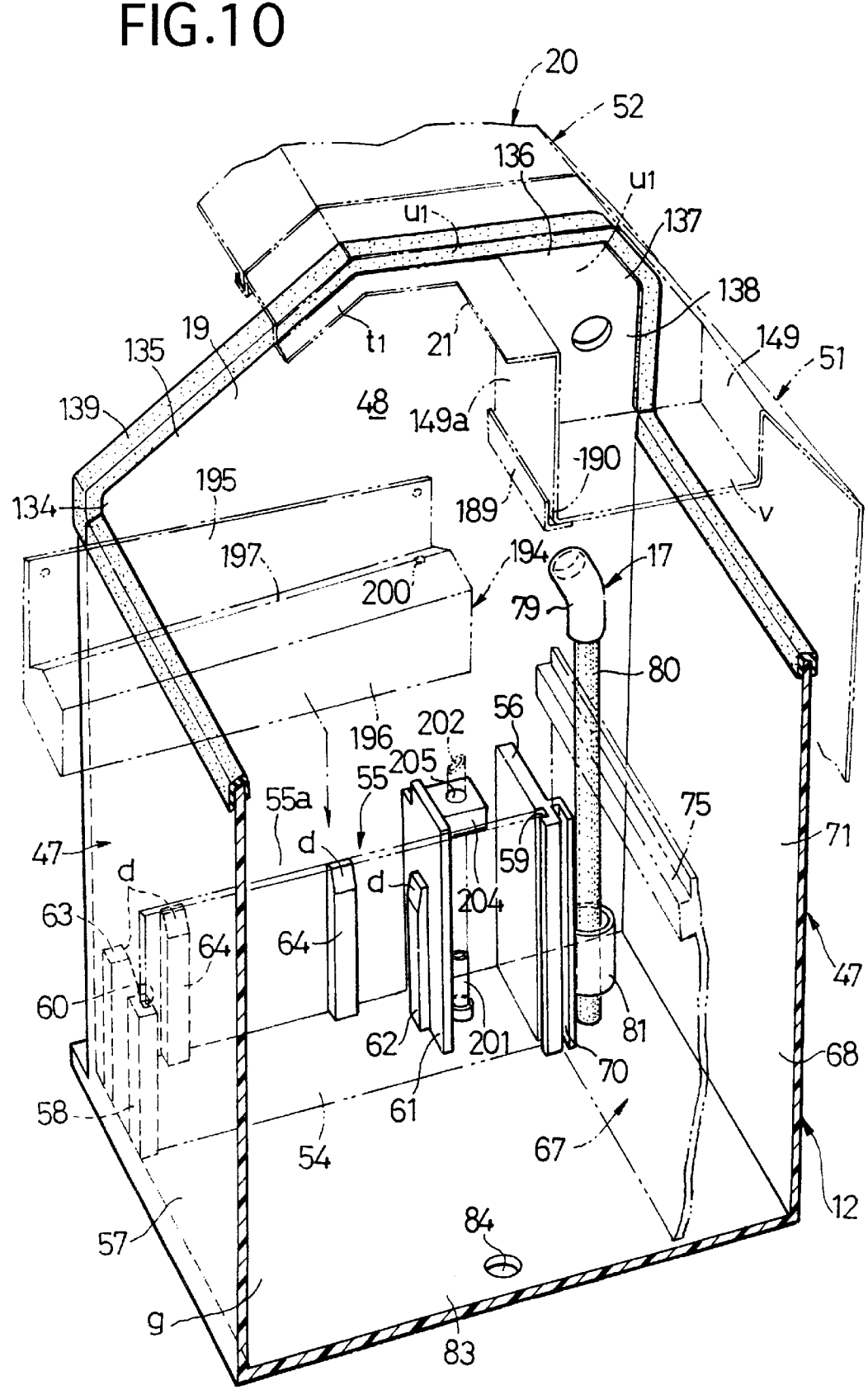
FIG. 10 is a perspective view showing the relationship among an electrolytic cell, a cover and a hood.

Above the heater chamber 68, an L-shaped water supply pipe 79 made of a synthetic resin pipe material in the water supply pipe line 17 is disposed in the left sidewall portion 48 of the electrolytic cell 12 with its outlet turned downwards. A tube 80 made of a soft synthetic resin is attached to the water supply pipe 79, as best shown in FIG. 10, and has a lower end portion loosely inserted into a retaining sleeve 81 made of a synthetic resin and mounted to a rear surface of the division plate 56 adjacent to the heater chamber 68. The retaining sleeve 81 prevents the lower end portion of the tube 80 from being swung uselessly during supplying of water. The tube 80 is withdrawn from the retaining sleeve 81 and also used for washing the electrolytic cell 12.

Figure 14:
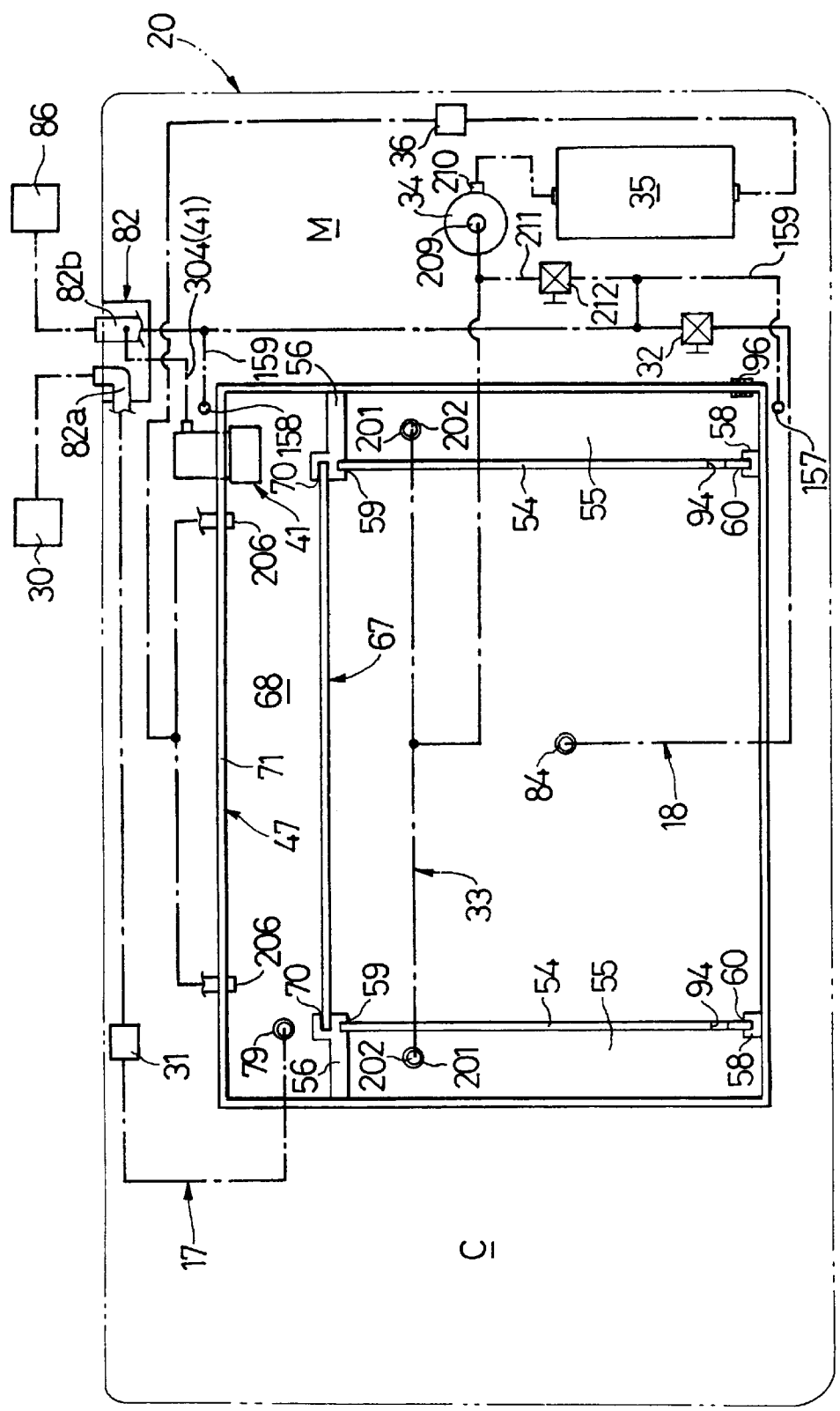
FIG. 14 is an illustration of a piping in the electrolytic test machine.

As best shown in FIGS. 8 and 14, half of the water supply pipe line 17 on the side of the water supply pipe 79 is connected to a water supply portion 82a of a water dispensing block 82 mounted on the machine base 44 via outer surfaces of the left sidewall portion 48 and the rear wall portion 71, and half of the water supply pipe line 17 on the side of the cock 30 for the water service is connected to the water supply portion 82a. In the half of the water supply pipe line 17 on the side of the water supply pipe 79, the solenoid valve 31 is mounted at an intermediate portion thereof. The preparation of the aqueous solution of NaCl 11 is carried out within the electrolytic cell 12 after supplying of water to the electrolytic cell 12.

A drainage port 84 is opened in a central portion of a bottom wall 83 of the electrolytic cell 12, and the drainage pipe line 18 made of a synthetic resin pipe material is connected to the drainage port 84. Half of the drainage pipe line 18 on the side of the drainage port 84 is passed through the inside of the machine base 44 and connected to a drainage portion 82b of the water dispensing block 82. Half of the drainage pipe line 18 on the side of a drainage channel 86 is connected to the drainage portion 82b. In the half of the drainage pipe line 18 on the side of the drainage port 84, the manual cock 32 is mounted at an intermediate portion thereof.

[E] Control of Water Level of Electrolytic Cell (FIGS. 7 and 8)

The water level sensor 15 for controlling the amount of the aqueous solution of NaCl 11 is disposed at the right end of the inner surface of the rear wall portion 71 of the electrolytic cell 12. The water level sensor 15 includes first, second and third detecting elements i, j and k extending vertically and different in level of their lower end from one another. These detecting elements are supported on a support 87 of the rear wall portion 71 located above the liquid level f of the aqueous solution of NaCl 11. The lower end of the first detecting element i lies at a highest position; the lower end of the third detecting element k lies at a lowest position and the lower end of the second detecting element j lies at a middle position between both the lower ends of the first and third detecting elements i and k.

During supplying of water to the electrolytic cell 12, the first and third detecting elements i and k are non-conducting therebetween, and the solenoid valve 31 is controlled into an opened state by the control unit 10. If the liquid level f is risen up to the lower end of the first detecting element i, the first and third detecting elements i and k are brought into conduction therebetween, and the solenoid valve 31 is controlled into a closed state by the control unit 10. This causes the supplying of water to be stopped. If the liquid level f is lowered and spaced apart from the lower end of the first detecting element i during a test, the first and third detecting elements i and k are brought into non-conducting therebetween, and the solenoid valve 31 is brought into the opened state, thereby permitting the supplying of water to be effected. In this manner, the amount of aqueous solution of NaCl 11 is usually controlled by the first detecting element i.

On the other hand, if the supplying of water is not carried out even if the liquid level f is spaced apart from the lower end of the first detecting element i due to the failure of movement of the first detecting element i in the test, the second and third detecting elements j and k are brought into non-conduction therebetween when the liquid level f is lower and is spaced apart from the lower end of the second detecting element j, and the DC power source 9 is controlled into an OFF state by the control unit 10. This causes the supplying of electric current to the carbon electrodes 13 and the test material 2 to be cut off, thereby stopping the test.

The second and third detecting elements j and k are also used for the control of both the electric heaters 14. More specifically, if the aqueous solution of NaCl 11 is in a defined amount, the lower ends of the second and third detecting elements j and k are located in the aqueous solution of NaCl 11, and the second and third detecting elements j and k are in conduction therebetween and hence, both the electric heaters 14 are controlled into energized states by the control unit 10. For example, if the liquid level f is spaced apart from the lower end of the second detecting element j, the second and third detecting elements j and k are brought into non-conduction therebetween and hence, both the electric heaters 14 are controlled into energization-stopped states by the control unit 10.

[F] Structure of Wiring of Carbon Electrode and Energizing Terminal Base for Test Material (FIGS. 8, 9, 11, 13 and 15)

In the front wall portion 57 of the electrolytic cell 12, a receiving member 88 made of a synthetic resin having a channel-like configuration is fixed to extend laterally above the U-shaped support 74.

As best shown in FIGS. 8 and 9, a vertical and quadrilateral frame 90 in the machine base 44 extends along the outer surface of the right sidewall portion 49 of the electrolytic cell 12, and a terminal box 92 is fixed to an upper surface of a lower angle member 91 extending longitudinally of the frame 90.

Figure 11:
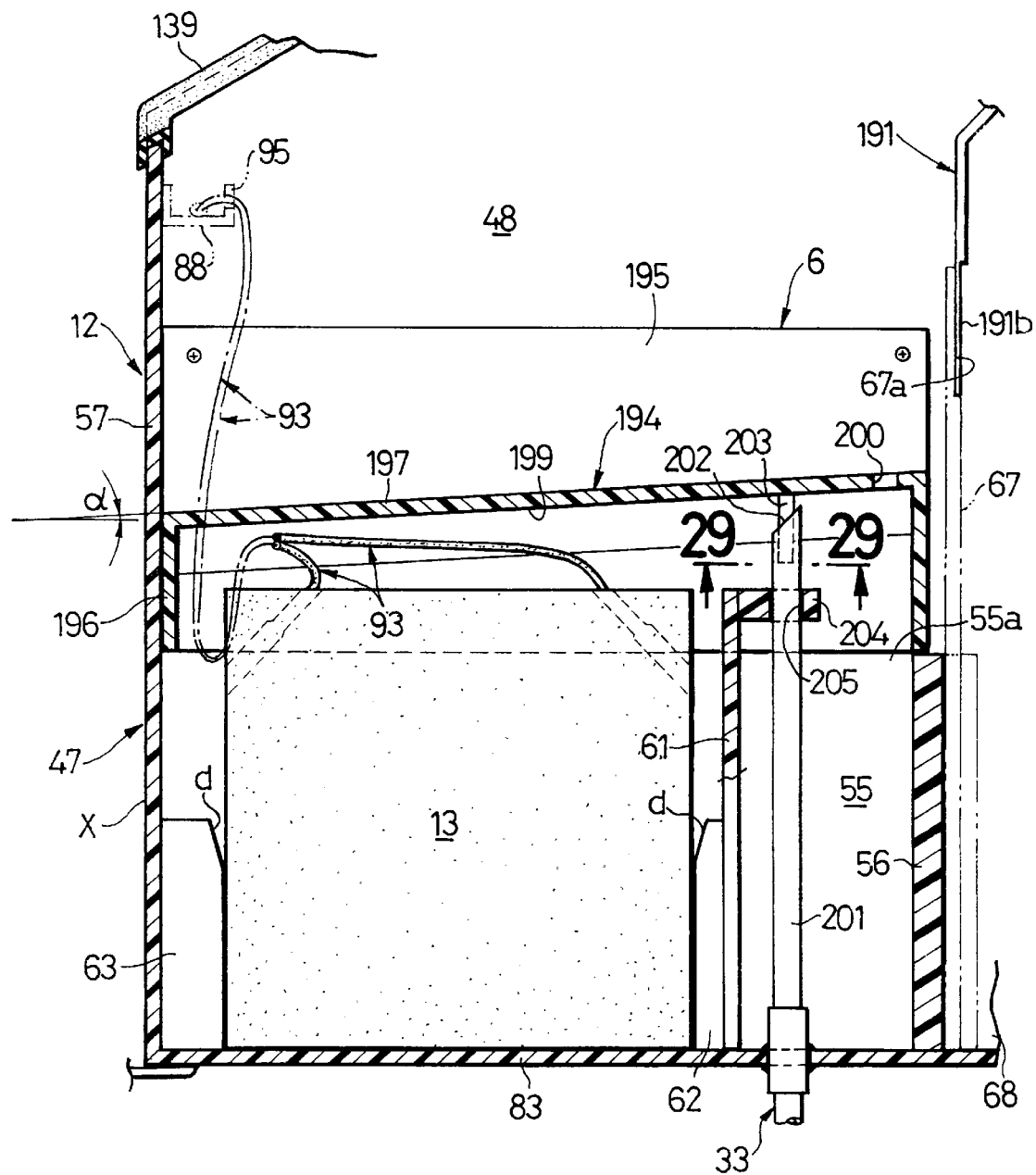
FIG. 11 is a sectional view taken along a line 11—11 in FIG. 7.
Figure 12:
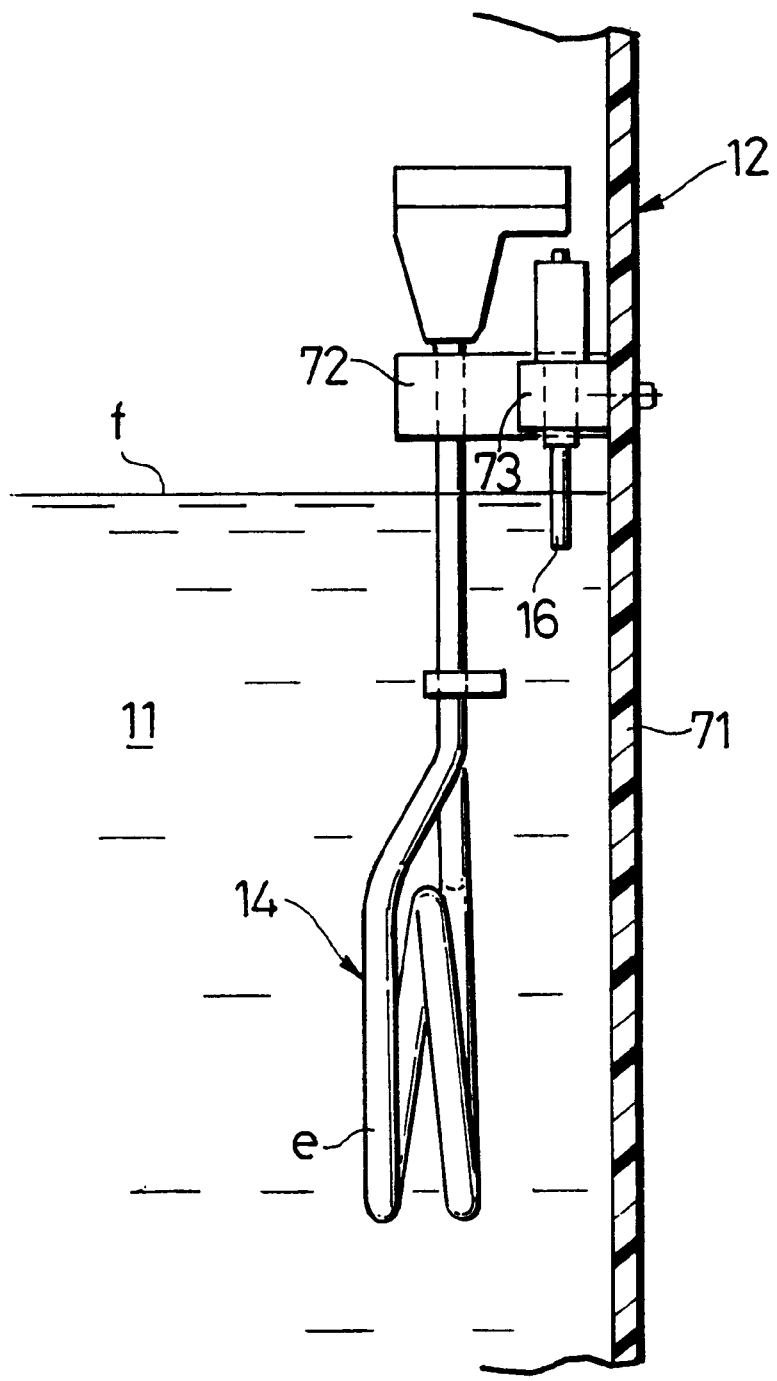
FIG. 12 is a sectional view taken along a line 12—12 in FIG. 8.
Figure 15:
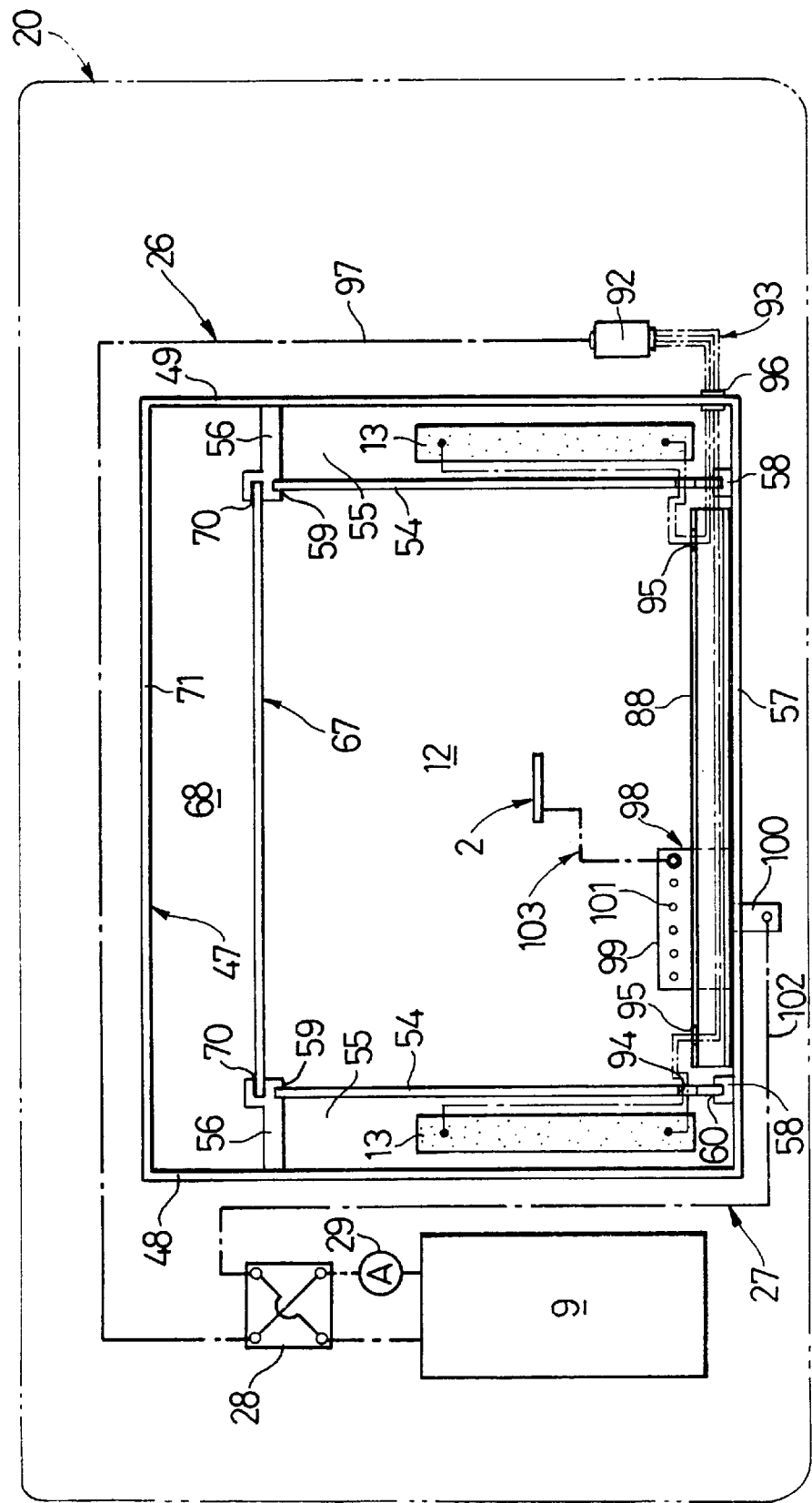
FIG. 15 is an illustration of a wiring in the electrolytic test machine.

Referring to FIGS. 11, 13 and 15, feeder wires 93 are connected to front and rear sides of the upper portions of the left and right carbon electrodes 13, respectively. The two feeder wires 93 of each carbon electrode 13 are drawn to the outside of the electrode chamber 55 through a notch 94 of each partition plate 54. As shown in FIGS. 9 and 15, the feeder wires are passed into the inside of the receiving member 88 from notches 95 of the receiving members 88, where they are collected into four wires. The feeder wires are drawn through a grommet 96 of the right sidewall portion 49 to the outside of the electrolytic cell 12 and connected to connection terminals of the terminal box 92. Mains 97 connected to the connection terminals of the terminal box 92 are drawn from the terminal box 92. The mains 97 are extended along the outer surfaces of the right sidewall portion 49, the rear wall portion 71 and the left sidewall portion 48 of the electrolytic cell 12, and connected to the DC power source 9 through the polarity switch-over relay 28. The feeder wires 93, the terminal box 92 and the mains 97 constitute one of the energizing lines 26.

Referring again to FIGS. 8, 13 and 15, an energizing terminal base 98 made of titanium used for connection to the test material 2 is mounted on the front wall portion 57 of the electrolytic cell 12 to lie below the receiving member 88 and in the vicinity of the U-shaped support 74. A first connecting portion 99 of the energizing terminal base 98 with the test material 98 is disposed within the electrolytic cell 12, and a second connecting portion 100 of the energizing terminal base 98 with the DC power source 9 is disposed outside the electrolytic cell 12. A plurality of connecting bores 101 each having internal threads are defined in the first connecting portion 99, so that they correspond to a plurality of feeder wires 103 connected to a plurality of test materials 2. Mains 102 are connected to the second connecting portion 100. The mains 102 are extended along the outer surfaces of the front wall portion 57 and the left sidewall portion 48, and connected to the DC power source 9 through the polarity switch-over relay 28. The feeder wires 103, the energizing terminal base 98 and the mains 102 constitute the other energizing line 27.

Figure 16:
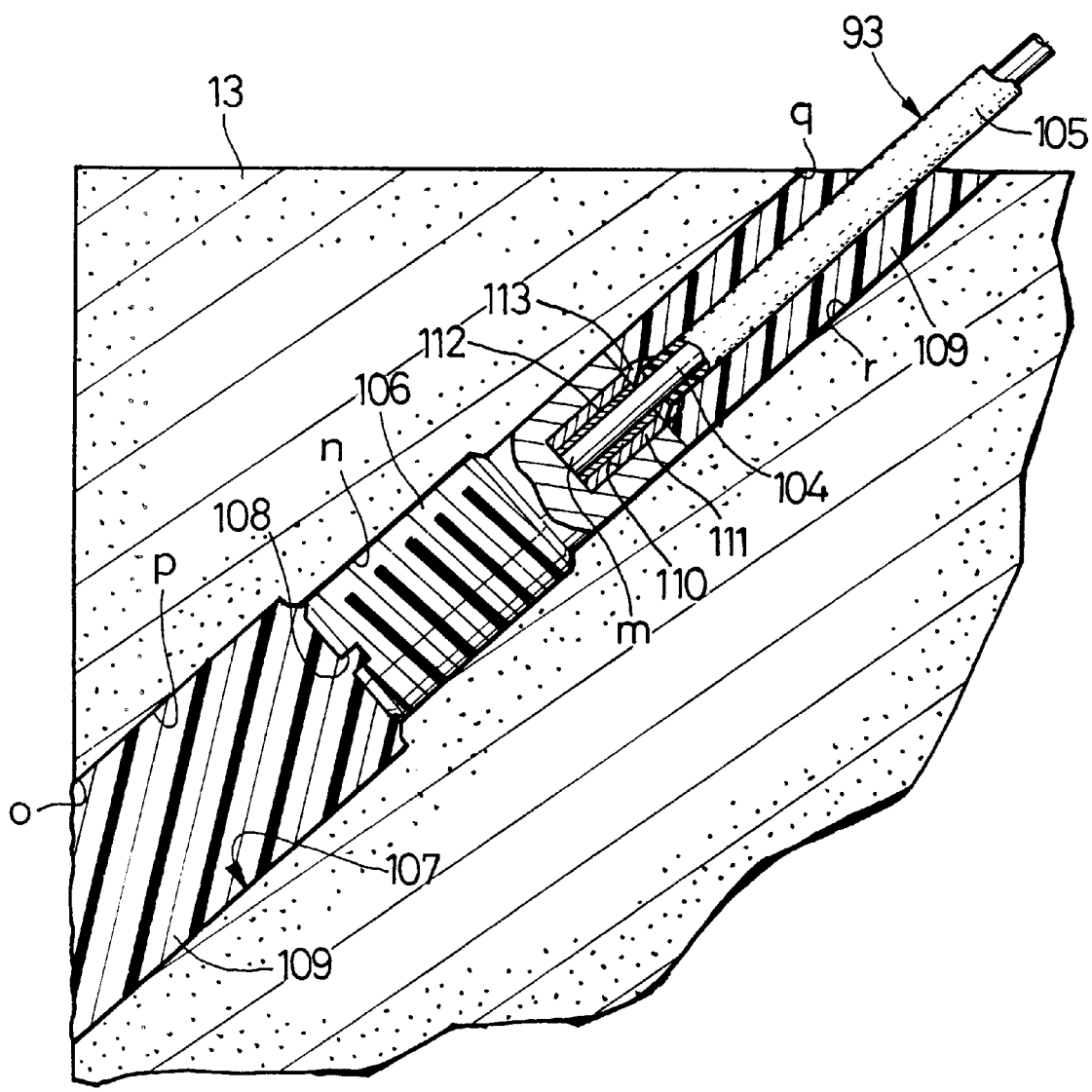
FIG. 16 is a sectional view showing the structure of a connection of a carbon electrode with an electric feeder wire.

[G] Structure of Connection of Carbon Electrode with Feeder Wires (FIG. 16)

Each of the feeder wires 93 has a conductor 104 and a corrosion-resistant insulating coating layer 105. A terminal end m of the conductor 104 protruding from the corrosion-resistant insulating coating layer 105 of the feeder wire 93 is connected to a conductive connecting bolt 106. A connecting bore 107 is defined in a corner of the carbon electrode 13 and has a threaded portion n at its deep area. The connecting bolt 106 is threadedly engaged with the threaded portion n.

The connecting bore 107 may be a blind bore, but in the illustrated embodiment, the connecting bore 107 is a through-bore extending obliquely and vertically. The feeder wire 93 and the connecting bolt 106 are inserted into the connecting bore 107 through a lower opened end o of the connecting bore 107. To this end, the connecting bolt 106 has an engage portion for engagement with a tool, e.g., a minus screwdriver, namely, an engage groove 108, at an end opposite from an end to which the feeder wire 93 is connected.

A seal material 109 such as a silicone is filled in a void space p of the connecting bore 107 located between the lower opened end o of the connecting bore 107 and an end face of the connecting bolt 106 on the side of the engage groove 108. A seal material 109 similar to the above seal material is also filled in a void space r of the connecting bore 107, which is located between an upper opened end q and an end face of the connecting bolt 106, from which the feeder wire 93 extends, and which surrounds the insulating coating layer 105 of the feeder wire 93.

The structure of connection of the connecting bolt 106 with the terminal end m of the conductor 104 of the feeder wire 93 is as follows: The connecting bolt 106 is formed of a titanium for the purpose of enhancing the corrosion resistance of the connecting bolt 106, and has a blind bore 110 which opens into one end face thereof. A hollow tubular member 111 made of a copper alloy, e.g., brass in the illustrated embodiment is press-fitted into the blind bore 110, and the terminal end m of the conductor 104 is inserted into the hollow tubular member 111. and connected thereto through a soldering layer 112. Titanium is hard to solder and hence, the hollow tubular member 111 made of brass which is easier to solder is used.

A seal member 113 similar to the above-described seal material is disposed between one end face of the hollow tubular member 111 and an end face of the insulating coating layer 105 of the feeder wire 93 to surround the conductor 104 protruding from the end face of the insulating coating layer 105. Thus, it is possible to enhance the water-tightness of the conductor 104 protruding from the hollow tubular member 111 made of brass and the insulating coating layer 105 with respect to the aqueous solution of NaCl 11.

With the above construction, the connection between the carbon electrode 13 and the feeder wire 93 is performed within the connecting bore 107 in the carbon electrode 13 and hence, only the feeder wire 93 is exposed to the outside, thereby providing a compactness of the connecting structure.

In addition, the connecting portion between the carbon electrode 13 and the conductor 104 of the feeder wire 93 is reliably sealed and hence, the water-tightness of the connecting portion to the aqueous solution of NaCl 11 can be largely enhanced to avoid the corrosion of the connecting portion.

Further, since the connecting portion has an excellent water-tightness as described above, the carbon electrode 13 can be immersed into the aqueous solution of NaCl 11, thereby increasing the effective volume of the aqueous solution of NaCl, as compared with the case where the upper portion of the carbon electrode is placed to protrude from the liquid level, and the connecting portion is disposed therein.

Moreover, since the connecting bolt 106 is threadedly engaged with the internal threaded portion n of the carbon electrode 13, the property of close contact between the internal threaded portion n and the connecting bolt 106 can be improved, whereby the carbon electrode 13 and the feeder wire 93 can be reliably electrically connected to each other.

The connecting bolt 106 and the end of the feeder wire 93 connected to the connecting bolt 106 are fixed within the connecting bore 107 by the seal material 109, leading to a high strength of mechanical connection between the carbon electrode 13 and the feeder wire 93.

[H] Corrosion resistance test for Test Material (FIGS. 1 to 3, 13, 15 and 17 to 21)

For a corrosion resistance test, a damaged portion 114 is formed by a cutter in the coating film 4 on one flat surface of the test material 2 to reach the steel plate 3, as shown in FIGS. 1 and 2. In this case, each of the coating film 4 on the other surface of the test material 2 and the coating film 4 on the peripheral surface function as a masking for the steel plate 3. The bore 115 in the test material 2 is used for permitting the hanging string 25 made of the synthetic resin to be passed therethrough.

In the corrosion resistance test for the test material 2, a process is carried out which includes immersing the test material 2 into the aqueous solution of NaCl 11, and then allowing a DC current to flow between the steel plate 3 and both the carbon electrodes 13 in the aqueous solution of NaCl 11 and alternately switching over the polarity of the steel plate 3 to the positive or negative.

When the polarity of the steel plate 3 is negative, the coating film peeling-off step is performed. During this step, OH ions produced by electrolysis of water reduce the adhesion force of the coating film 4 to the steel plate 3 starting at the damaged portion 114 of the coating film 4, thereby promoting the peel-off and a blister of the coating film. On the other hand, when the polarity of the steel plate 3 is positive, the steel plate corroding step, namely, the anode oxidizing step, is performed. By alternately repeating such peeling-off of the coating film and anode oxidation, the peeling-off of the coating film 4 and the corrosion of the steel plate 3 starting at the damaged portion 114 can be promoted, whereby an overall estimation of corrosion resistance can be performed within a short time.

In the steel plate corroding step, the amount of steel plate 3 corroded is proportional to an amount of coulomb used for the energization, but even in the same amount of coulomb, if the coating film peeled-off area of the steel plate 3 is varied, the amount of corrosion is varied. Therefore, the amount of coulomb required to corrode the steel plate 3 is determined based on the coating film peeled-off area of steel plate 3.

Thereupon, a procedure is employed which involves measuring the coating film peeled-off area of steel plate 3 after the coating film peeling-off step, and determining the amount of coulomb in the steel plate corroding step in accordance with the coating film peeled-off area of steel plate 3.

Figure 17:
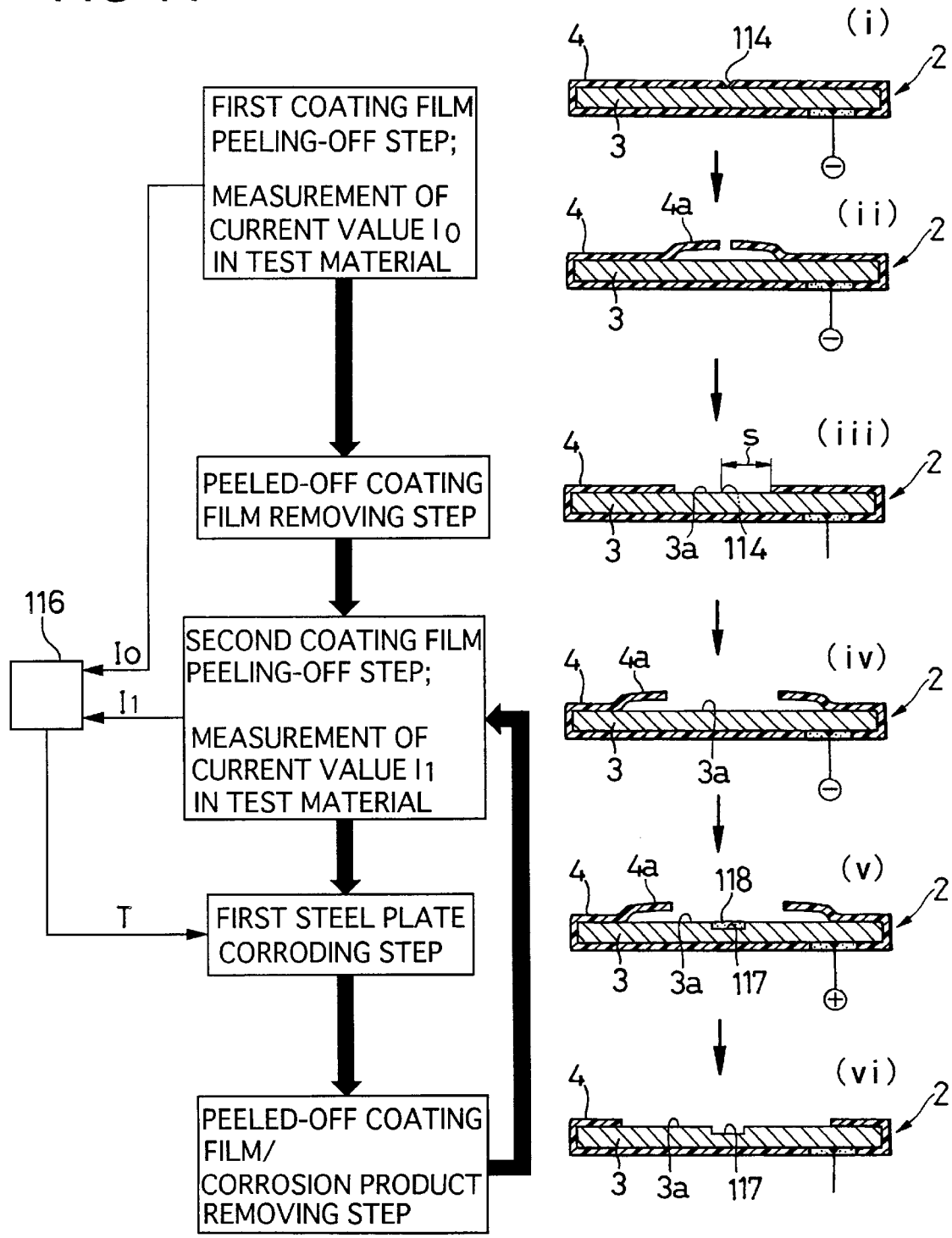
FIG. 17 is an illustration for explaining a corrosion resistance test.

FIG. 17 illustrates a corrosion resistance test process. The corrosion resistance test process will be described specifically with reference to FIG. 17.

(a) First Coating Film Peeling-off Step

At this step, the polarity of both the carbon electrodes 13 in the aqueous solution of NaCl 11 is set at the positive, while the polarity of the steel plate 3 of the test material 2 is set at the negative by the polarity switch-over relay 28, as shown in FIG. 17(*i*), and an electric current is supplied under a constant voltage from the DC power source 9 to between both the carbon electrodes 13 and the steel plate 3 through the aqueous solution of NaCl 11.

After a lapse of 5 to 10 minutes from the start of the supplying of the current, namely, after the current value is stabilized to some extent, a value $I_0$ of an electric current flowing in the steel plate 3 is measured by the ammeter 29.

The peeling-off of the coating film 4 does not occur within the above-described time, but a peeled-off coating film 4a is produced by a subsequent supplying of electric current, as shown in FIG. 17(*ii*).

The measurement of the current value $I_0$ may be carried out before the start of the first coating film peeling-off step. In this case, the polarity of the steel plate 3 is set at the negative. If the polarity of the steel plate 3 is set at the positive, the steel plate 3 is corroded at the damaged portion 114 of the coating film 4 and as a result, the coating film 4 is hardly peeled off at a next coating film peeling-off step.

(b) Peeled-off Coating Film Removing Step

The test material 2 is withdrawn out of the aqueous solution of NaCl 11, and the peeled-off coating film 4a is removed from the test material 2 using an adhesive tape, thereby exposing the coating film-peeled off surface 3a in the steel plate 3, as shown in FIG. 17(*iii*). This removal can be carried out by an ultra-sonic washing or a high-pressure water jet in the aqueous solution of NaCl 11.

(c) Second Coating Film Peeling-off Step

In this step, the polarity of both the carbon electrodes 13 in the aqueous solution of NaCl 11 is set at the positive, while the polarity of the steel plate 3 of the test material 2 is set at the negative by the polarity switch-over relay 28, as shown in FIG. 17(*iv*), and an electric current is supplied under a constant voltage from the DC power source 9 to between the carbon electrodes 13 and the steel plate 3 through the aqueous solution of NaCl 11.

Likewise, after a lapse of 5 to 10 minutes from the start of the supplying of the current, namely, after the current value is stabilized to some extent, a value $I_1$ of an electric current flowing in the steel plate 3 is measured by the ammeter 29.

The peeling-off of the coating film 4 does not occur within the above-described time, but a peeled-off coating film 4a is produced by a subsequent supplying of electric current, as shown in FIG. 17(*iv*).

(d) Step of Setting Amount of Coulomb in Corrosion of Steel Plate

The current values $I_0$ and $I_1$ measured at the step (a) and (c) are introduced to a calculating unit 116. In this calculating unit 116, a difference $\Delta I$ between both the current values $I_0$ and $I_1$ is first calculated. This difference $\Delta I$ is substantially proportional to the coating film peeled-off area of the steel plate 3 and hence, the measurement of the coating film peeled-off area is replaced by the calculation of the difference $\Delta I$. Then, an amount of coulomb corresponding to the difference $\Delta I$ is determined in terms of an energization time T under the constant voltage. This amount of coulomb can be determined by measuring a variation in voltage under a constant current, or by simultaneously measuring a current and a voltage.

(e) First Steel Plate Corroding Step

At this step, as shown in FIG. 17(*v*), the peeled-off coating film 4a produced at the step (c) is not removed, and the polarity of the carbon electrodes 13 in the aqueous solution of NaCl 11 is set at the negative, while the polarity of the steel plate 3 of the test material 2 is set at the positive by the polarity switch-over relay 28. An electric current is supplied under a constant voltage from the DC power source 9 to between the carbon electrodes 13 and the steel plate 3 through the aqueous solution of NaCl 11. The time of supplying the current is the energization time T determined at the step (d).

Thus, a recess 117 is formed in the coating film peeled-off surface 3a of the steel plate 3 by the corrosion (anode oxidization), and a corrosion product 118 is accumulated within the recess 117.

It be required that the first steel plate corroding step is carried out without removal of the peeled-off coating film 4a produced at the step (c) [in FIG. 17(*iv*)]. If the peeled-off coating film 4a is removed, the amount of coulomb determined at the step (d) and the coating film peeled-off area of the steel plate 3 are unequal to each other. In addition, if the peeled-off coating film 4a is not removed, the coating film peeled-off area of the steel plate 3 in the corroding step is little different from the coating film peeled-off area of the steel plate 3 produced at the step (b) [FIG. 17(*iii*)].

(f) Step of Removing Peeled-off Coating Film and Corrosion Product

The test material 2 is withdrawn from the aqueous solution of NaCl 11, and the peeled-off coating film 4a and the corrosion product 118 are removed from the test material 2 using an adhesive tape, thereby exposing the coating film peeled-off surface 3a and the recess 117 in the steel plate 3, as shown in FIG. 17vi. This removal can be carried out likewise by an ultrasonic washing or a high-pressure water jet in the aqueous solution of NaCl 11.

Thereafter, if required, a plurality of cycles each including steps from the second coating film peeling-off step to the peeled-off coating film/corrosion product removing step may be repetitively carried out. In this case, the difference $\Delta I$ is calculated, for example, from a current value $I_1$ measured at the second coating film peeling-off step in a first cycle and a current value $I_2$ measured at the third coating film peeling-off step in a second cycle.

If the coating film peeling-off step is carried out subsequent to the steel plate corroding step, the peeling-off of the coating film 4 is obstructed by the corrosion product 118 and hence, it is necessary to interpose the peeled-off coating film/corrosion product removing step between both the coating film peeling-off step and the steel plate corroding step.

Particular examples will be described below.

I. Coating film Peeling-off Test

A coating film peeling-off test which will be described below was carried out to examine the relationship between the applied voltage and the degree of peeling-off of the coating film 4.

(1) Conditions for Test Material 2

Steel plate:
   width: 70 mm; length: 150 mm; thickness: 1.017 mm

Coating film:
   A pre-treating agent available under the trade name SD2800 from Nippon Paint is used; a coating method: a cation electrostatic coating; film thickness: 20 to 25 $\mu$m; a damaged portion is formed into a length of 50 mm using a cutter.

In addition, a test material 2 was made under the same conditions, except that the pre-treatment was not carried out.

Figure 18:
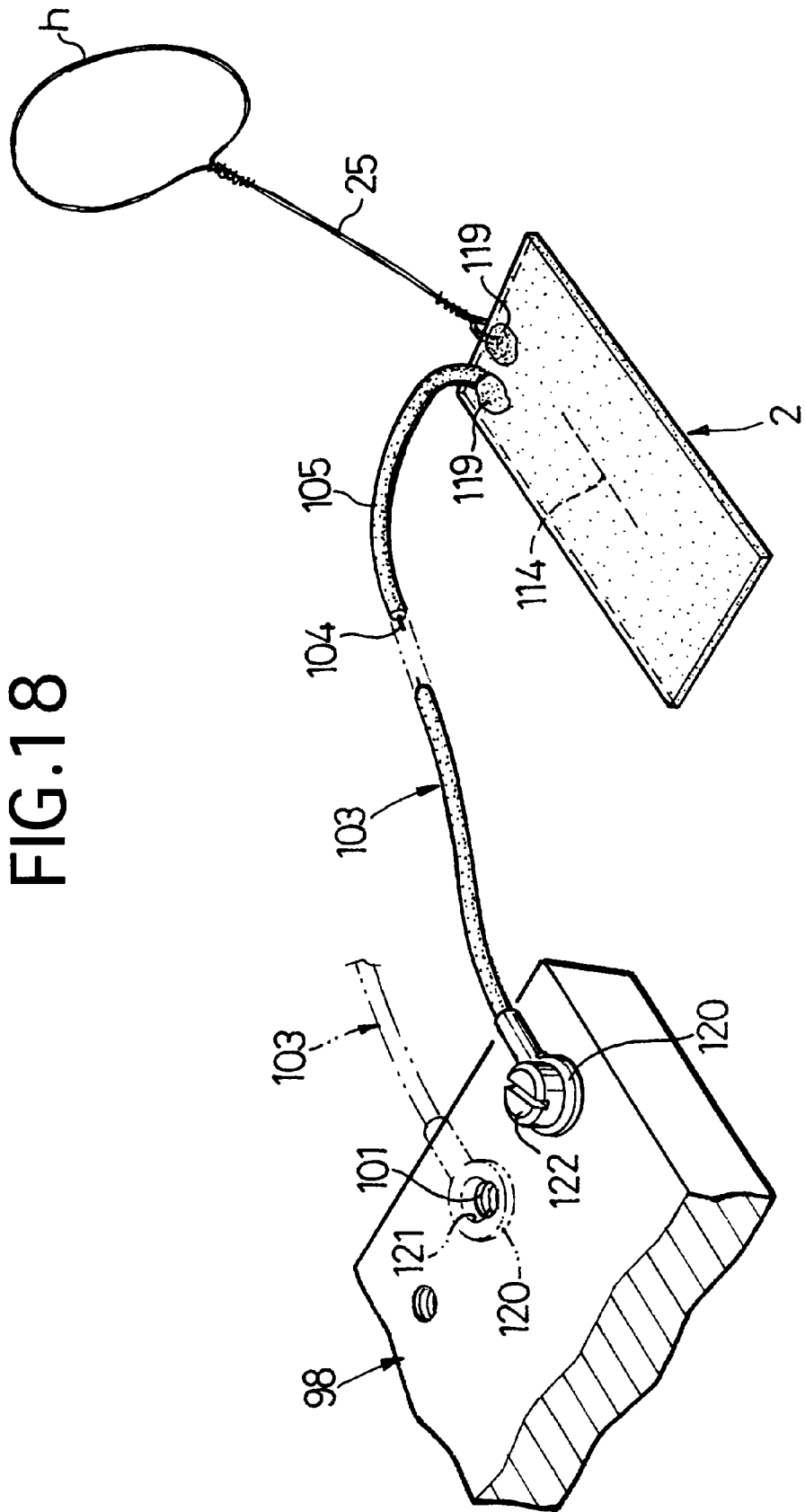
FIG. 18 is a perspective view showing the connection of the test material with an energizing terminal base.

As shown in FIG. 18, one end of the string 25 made of the synthetic resin was tied in the bore 115 in the test material 2, and a loop h was formed at the other end of the string 25. The conductor 104 protruding from the corrosion resistant insulating coating layer 105 of the feeder wire 103 was soldered to the steel plate 3 on the surface of the test material 2 opposite from the surface having the damaged portion 114 provided thereon. Exposed portions of the steel plate 3 in the bore 115 in the test material 2 and the soldered zone of the test material 2 and the conductor 104 were covered by a seal member 119 similar to that described above. A bolt insertion bore 121 in a terminal 120 connected to the other end of the feeder wire 103 was aligned with the connecting bore 101 in the energizing terminal base 98, and the bolt 122 was threadedly inserted into the connecting bore 101 through the bolt insertion bore 121. This caused the steel plate 3 and the DC power source 9 to be electrically connected to each other through the polarity switch-over relay 28. The test material 2 was immersed into the aqueous solution of NaCl 11 by hanging it from the support bar 24 through the loop h of the string 25 made of the synthetic resin.

(2) The concentration of the aqueous solution of NaCl 11 was set at 3%, and the temperature of the aqueous solution of NaCl 11 was set at 40° C. The polarity of the steel plate 3 was set at the negative, while the polarity of the carbon electrode 13 was set at the positive, and the test time was set at 2 hours. The applied voltage was varied in a range of 0 to 20 V. Under such conditions, the coating film peeling-off test for the test material 2 was carried out.

(3) Test Result

Figure 19:
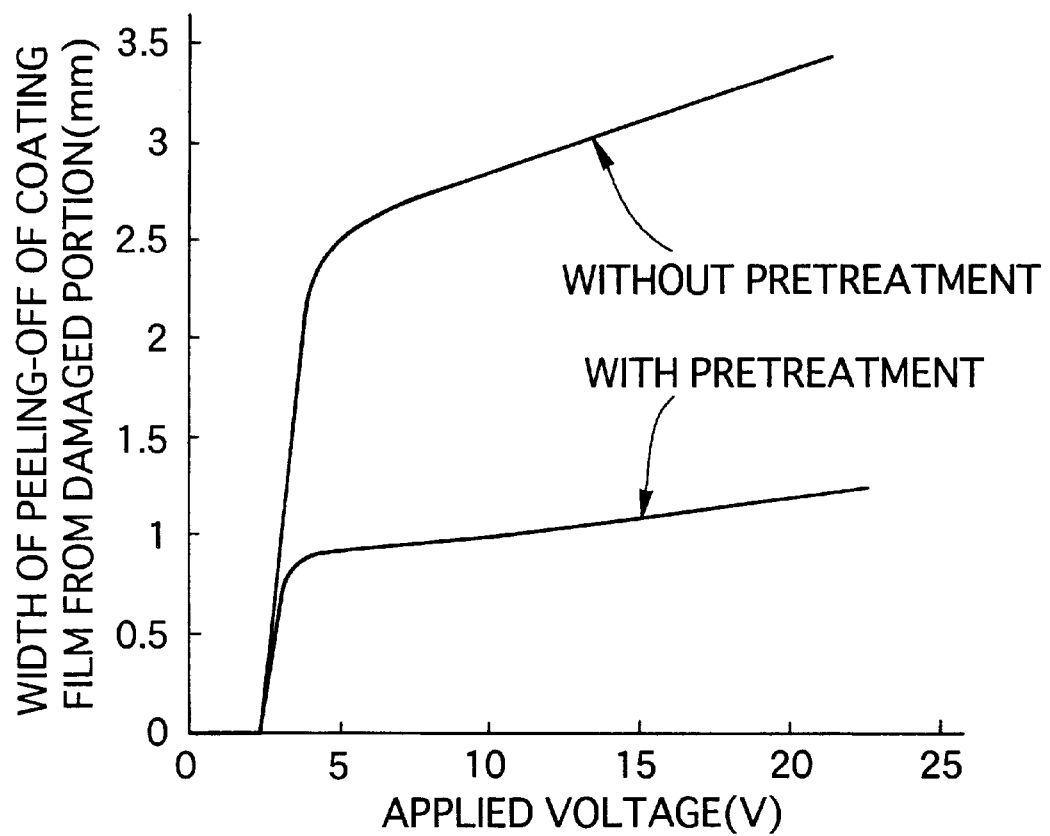
FIG. 19 is a graph illustrating the relationship between the applied voltage and the width of peeling-off of a coating film from a damaged portion of the test material.

FIG. 19 is a graph illustrating the relationship between the applied voltage and the width s of coating film peeled off from the damaged portion 114 [see FIG. 17 (iii)]. As apparent from FIG. 19, the peeling-off of the coating film 4 is started at the applied voltage of about 2.5 V, whether the pre-treatment is carried out or not carried out. To perform the peeling-off of the coating film with stability, it is preferred that the applied voltage is set at about 5.5 V or more for the test material 2 subjected to the pretreatment and at about 8 V or more for the test material 2 not subjected to the pretreatment.

At the same applied voltage, the amount of coating film 4 peeled off is smaller in the test material 2 subjected to the pretreatment than in the test material 2 not subjected to the pretreatment. It can be mentioned from this that the pretreatment is preferably carried out in order to enhance the durability of the coating film 4.

II. Corrosion Resistance Test (1) Conditions for the test material 2 in the corrosion resistance test are identical to those described in the item I.

(2) Steps and conditions for the steps in a particular example are as shown in Table 1. In this case, the concentration of aqueous solution of NaCl was set at 3%, and the temperature the aqueous solution of NaCl was set at 45° C.

TABLE I

| Cycle | Step | Voltage | Current Value | Difference $\Delta I$ | Energizing time |
|---|---|---|---|---|---|
| 1 | first coating film peeling-off | 16 V | $I_0$ = 1.9 A | — | 4 hours |
|  | second coating film peeling off | 16 V | $I_1$ = 14.9 A | $I_1 - I_0$ | 4 hours |
|  | first steel plate corrosion | 10 V | — | — | T = 1810 seconds |
| 2 | third coating film peeling-off | 16 V | $I_2$ = 18.3 A | $I_2 - I_1$ | 4 hours |
|  | second steel plate corrosion | 10 V | — | — | T = 1984 seconds |
| 3 | fourth coating film peeling-off | 16 V | $I_3$ = 19.6 A | $I_3 - I_2$ | 4 hours |

TABLE I-continued

| Cycle | Step | Voltage | Current Value | Difference $\Delta I$ | Energizing time |
|---|---|---|---|---|---|
|  | third steel plate corrosion | 10 V | — | — | T = 1986 seconds |
| 4 | fifth coating film peeling-off | 16 V | $I_4$ = 19.4 A | $I_4 - I_3$ | 4 hours |
|  | fourth steel plate corrosion | 10 V | — | — | T = 1472 seconds |

(3) A cycle corrosion test (CCT) enabling the deterioration of the coating film 4 and the corrosion of the steel plate 3 to be simultaneously estimated was carried out as a comparative example, using a test material 2 subjected to a pretreatment similar to the above-described pretreatment and a test material 2 not subjected to the pretreatment. Conditions for this test are as follows: a step for carrying out a spraying of salt water for 2 hours, a wetting for 2 hours and a drying for 4 hours was repeated three times. This was defined as one cycle. Therefore, the time required for one cycle is 24 hours.

(4) Result of Test

Figure 20:
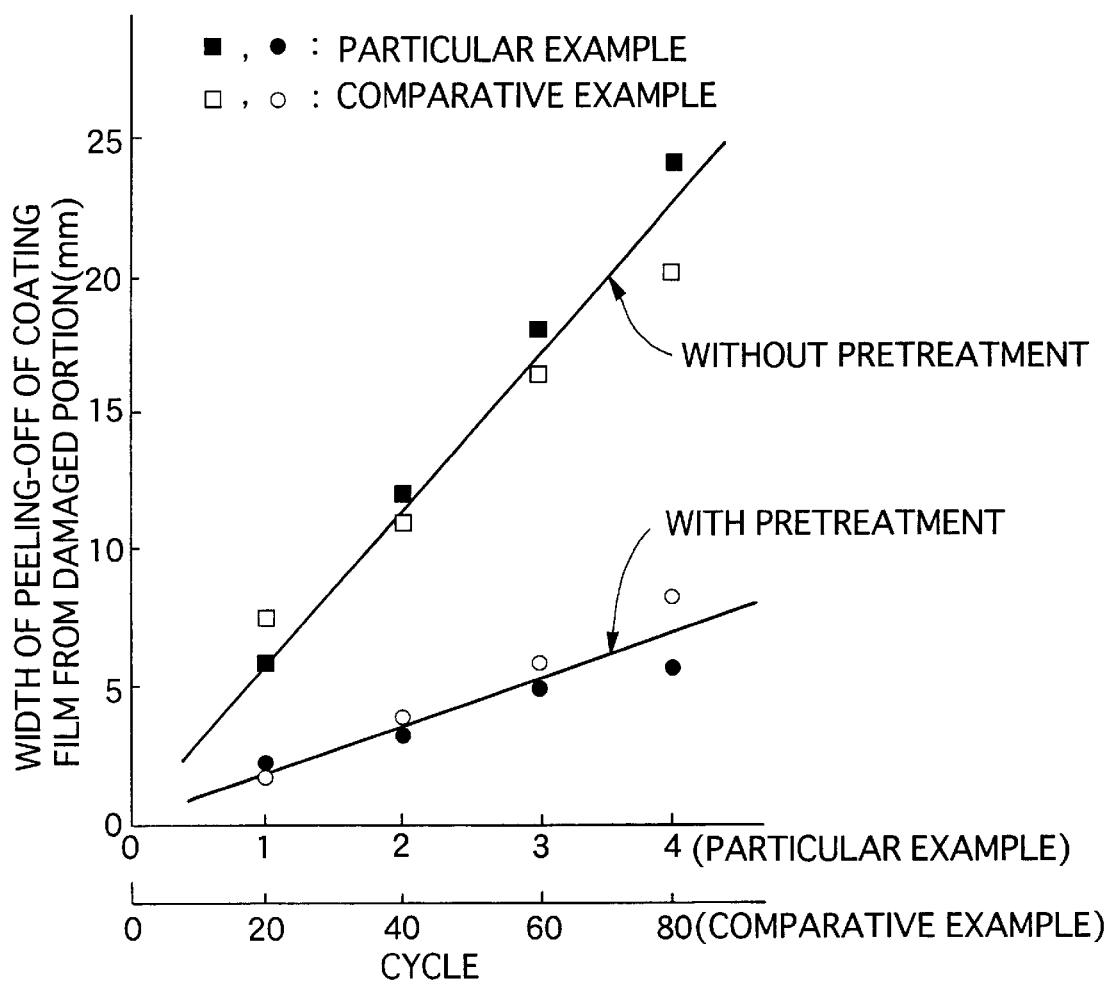
FIG. 20 is a graph illustrating the relationship between the cycle and the width of peeling-off of the coating film from the damaged portion of the test material.

FIG. 20 is a graph illustrating the relationship between the cycle and the width s [see FIG. 17(iii)] of coating film peeled off from the damaged portion 114 when 20, 40, 60 and 80 cycles in the comparative example correspond to 1, 2, 3 and 4 cycles in the particular example. As apparent from FIG. 20, the 1 cycle in the particular example substantially compares with 20 cycles in the comparative example in the above-described width s of coating film peeled off.

Table 2 shows the relationship between the cycle and the maximum decrement in plate thickness in the particular example using the test material 2 subjected to the pretreatment.

TABLE 2

| Cycle | Maximum decrement in plate thickness (mm) |
|---|---|
| 1 | 0.146 |
| 2 | 0.347 |
| 3 | 0.643 |
| 4 | 0.968 |

Figure 21:
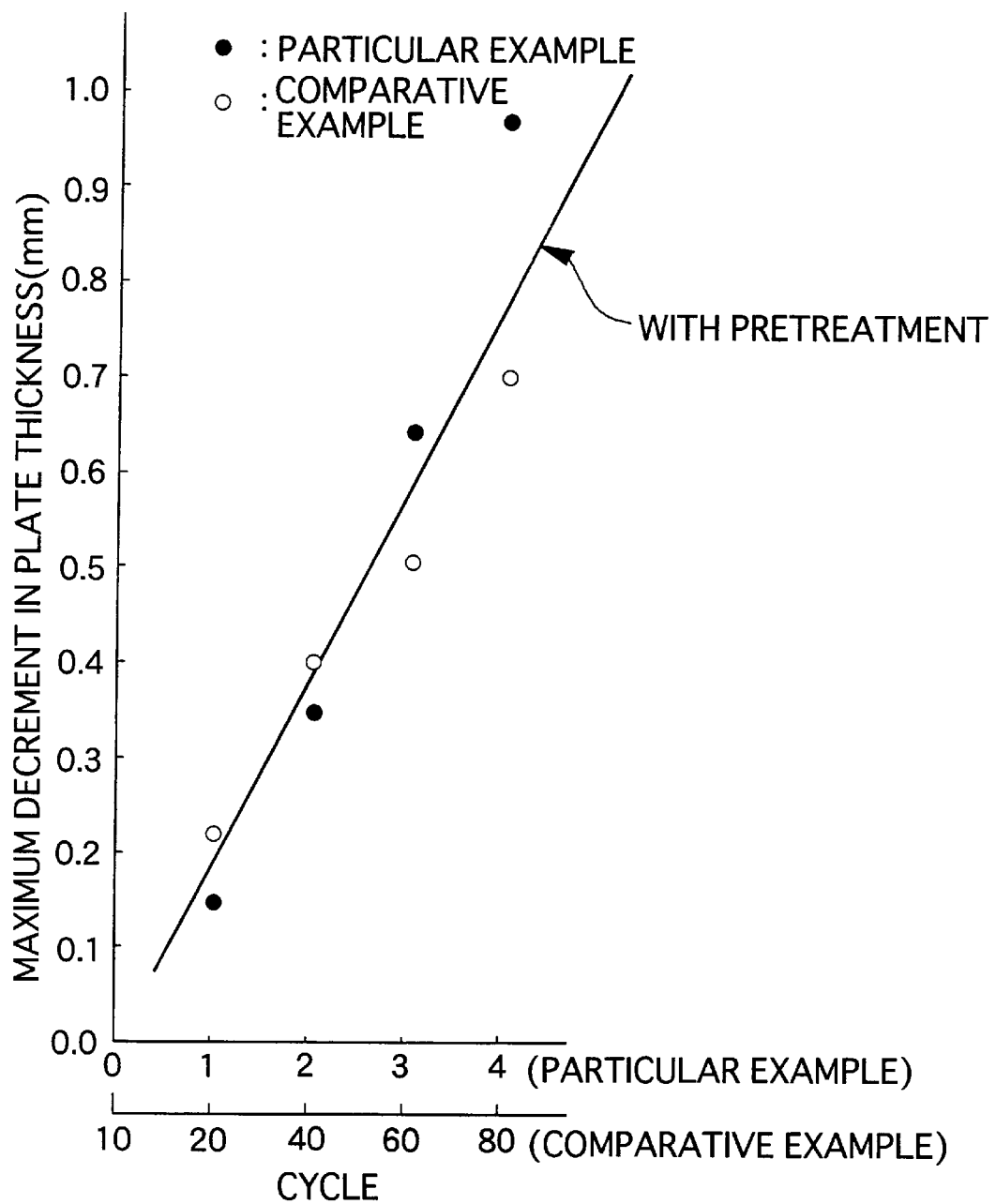
FIG. 21 is a graph illustrating the relationship between the cycle and the maximum decrement in plate thickness of the test material.

FIG. 21 is a graph illustrating the relationship between the cycle similar to the above-described cycle and the maximum decrement in plate thickness. Even in the comparative example, the test material 2 subjected to the pretreatment was used. As apparent from FIG. 21, the 1 cycle in the particular example substantially compares with the 20 cycles in the comparative example even in the above-described maximum decrement in plate thickness.

It is apparent from such result that in the particular example, the peeling-off of the coating film 4 and the corrosion of the steel plate 3, i.e., the metal blank, can be promoted, and the overall estimation of the corrosion resistance can be performed in a short time.

When only the peeling-off test for the coating film 4 is carried out, the polarity switch-over relay 28 is switched over, so that the polarity of the steel plate 3 is negative. In this case, the coating film 4 is provided only on one surface of the steel plate 3. This is because the steel plate corroding step is not included and hence, it is unnecessary to mask the other surface of the steel plate 3 and the like.

[I] Determining Device for Determining Timing of Replacement of Carbon Electrode (FIGS. 4 to 6 and 22 to 24)

Carbon particles of the carbon electrode 13 are drop from the carbon electrode 13 with use of the carbon electrode 13 for a long time, resulting in a varied energized area. In order to replace the carbon electrode 13 by a new carbon electrode 13, if it reaches the end of its service life, a determining device 123 is mounted in the electrolytic test machine 1. The device 123 is incorporated in the computer programmed control unit 10.

Figure 22:
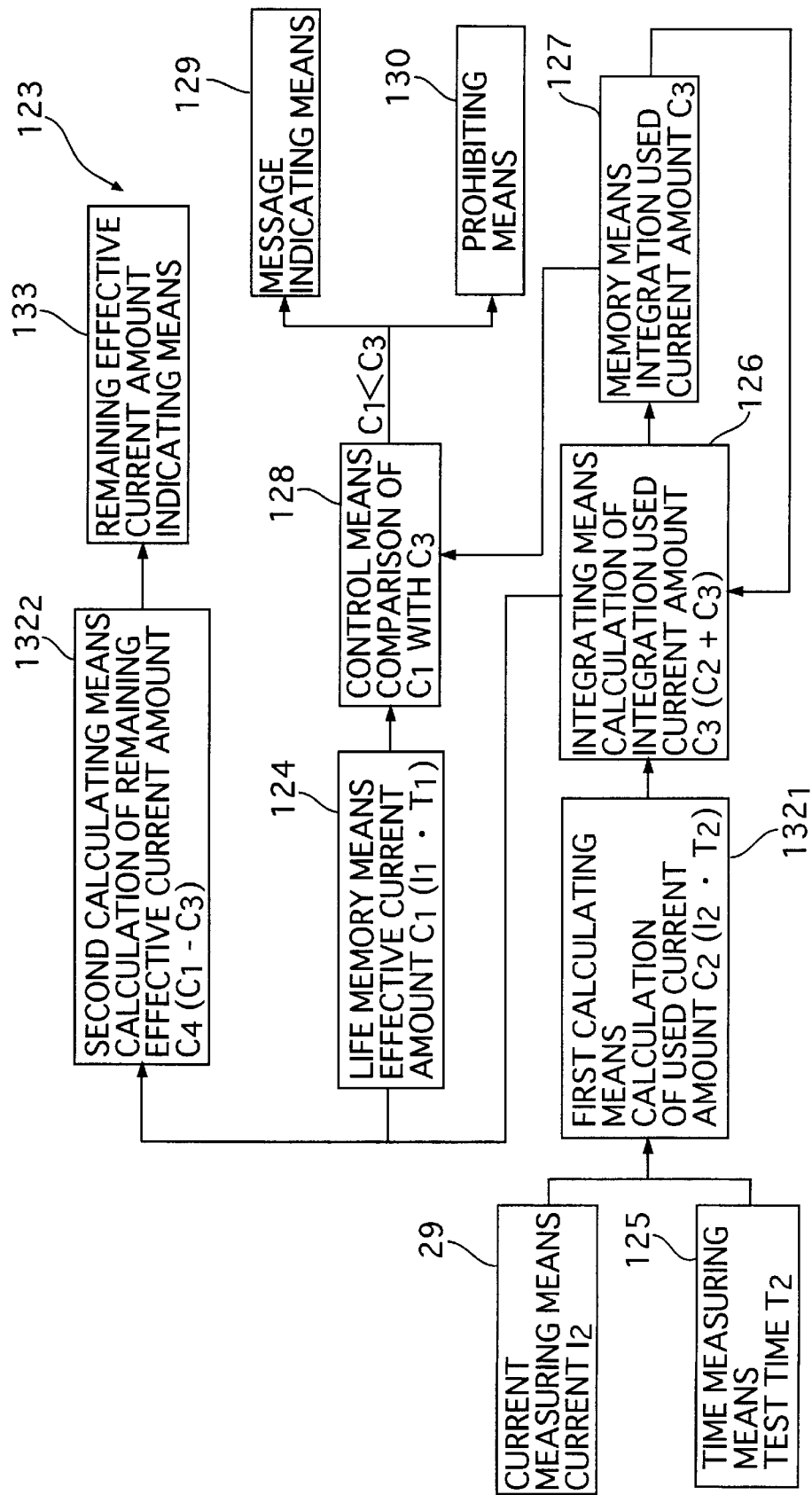
FIG. 22 is a block diagram of a determining device for determining a replacement time of the carbon electrode.
Figure 23:
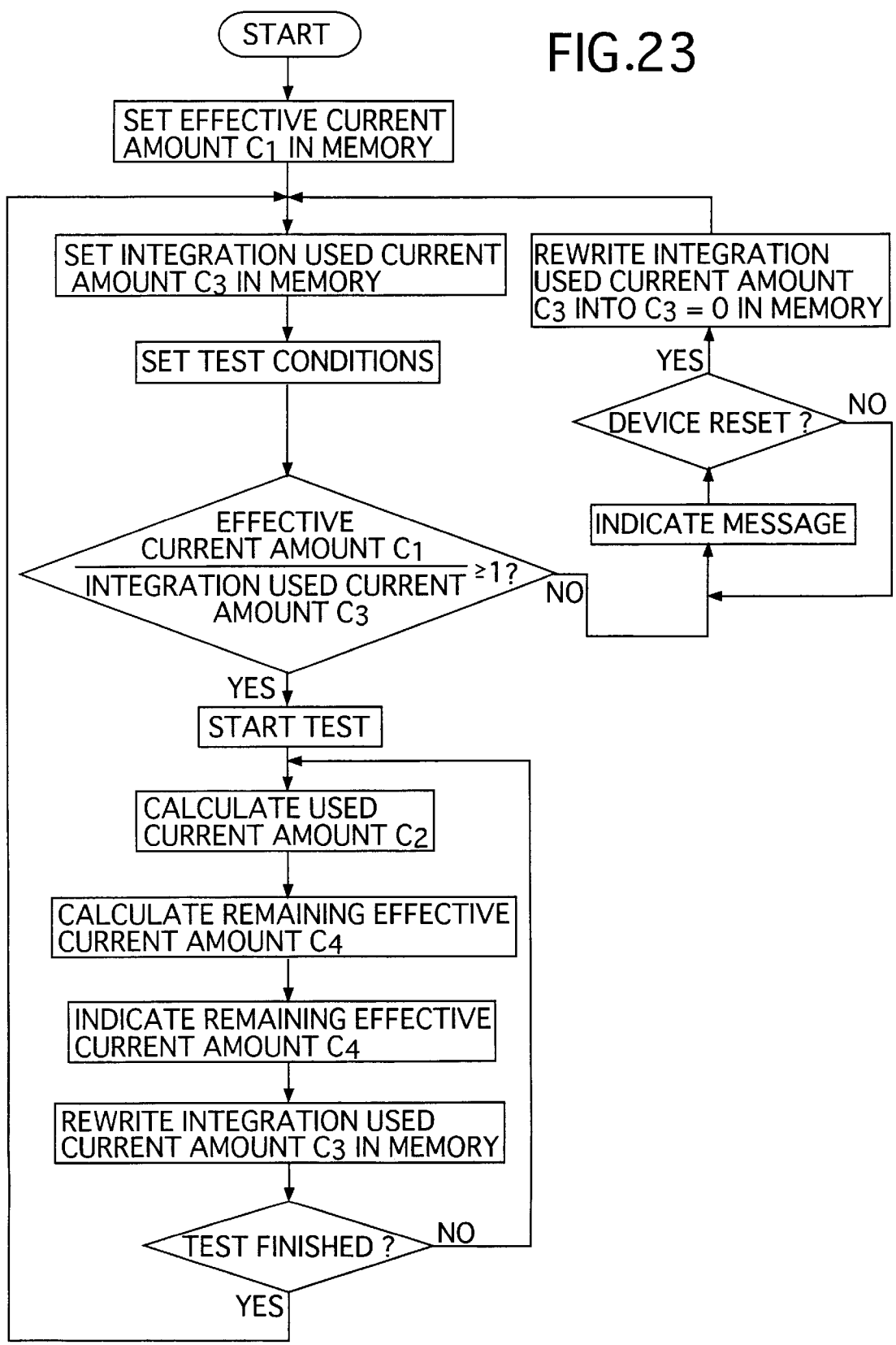
FIG. 23 a flow chart illustrating the operation of the determining device for determining the replacement time of the carbon electrode.

FIG. 22 is a block diagram of the determining device 123, and FIG. 23 is a flow chart illustrating the operation of the device 123. The term "set test conditions" in FIG. 23 means that any one of the condition that the corrosion resistance test including the coating film peeling step and the steel plate corroding step is to be carried out, the condition that the coating film peeling-off test is to be carried out and the condition that the test is to be finished, is selected, and each condition therefor is inputted.

Referring to FIG. 22, the determining device 123 includes a life memory means 124 for storing the service life of the carbon electrode 13 in the form of an effective current amount $C_1$ which is a product $I_1 \cdot T_1$ of a certain current $I_1$ flowing in the carbon electrode 13 and a total test time $T_1$ capable of being used when the current $I_1$ continues to flow, a current measuring means (ammeter) 29 for measuring a current $I_2$ flowing in the carbon electrode 13 during a test, a time measuring means 125 for measuring a test time $T_2$, a first calculating means $132_1$ for calculating a used current amount $C_2$ which is a product $I_2 \cdot T_2$ of the current $I_2$ and the test time $T_2$, an integrating means 126 for integrating the used current amounts $C_2$ to calculate an integration used current amount $C_3$ from the start of the use of the carbon electrode 13, a memory means 127 for storing the integration used current amount $C_3$, and a control means 128 adapted to compare the effective current amount $C_1$ with the integration used current amount $C_3$ at the start of the test and to transmit an electrode replacing signal, when $C_1 < C_3$.

With such arrangement, as the carbon electrode 13 which is a consumable electrode reaches the end of its service life, the timing of replacement of the carbon electrode 13 can be automatically detected.

In this case, even if the relationship between the effective current amount $C_1$ and the integration used current amount $C_3$ becomes $C_1 < C_3$ after the start of the test, the test is continued. This is permitted by counting on a margin of the effective current amount $C_1$ corresponding to several runs of the test.

The determining device 123 includes a message indicating means 129 for informing a testing operator of the reaching of the electrode replacing timing, based on the electrode replacing signal from the control means 128, and a prohibiting means 130 for prohibiting the supplying of current to the carbon electrode 13.

Figure 4:
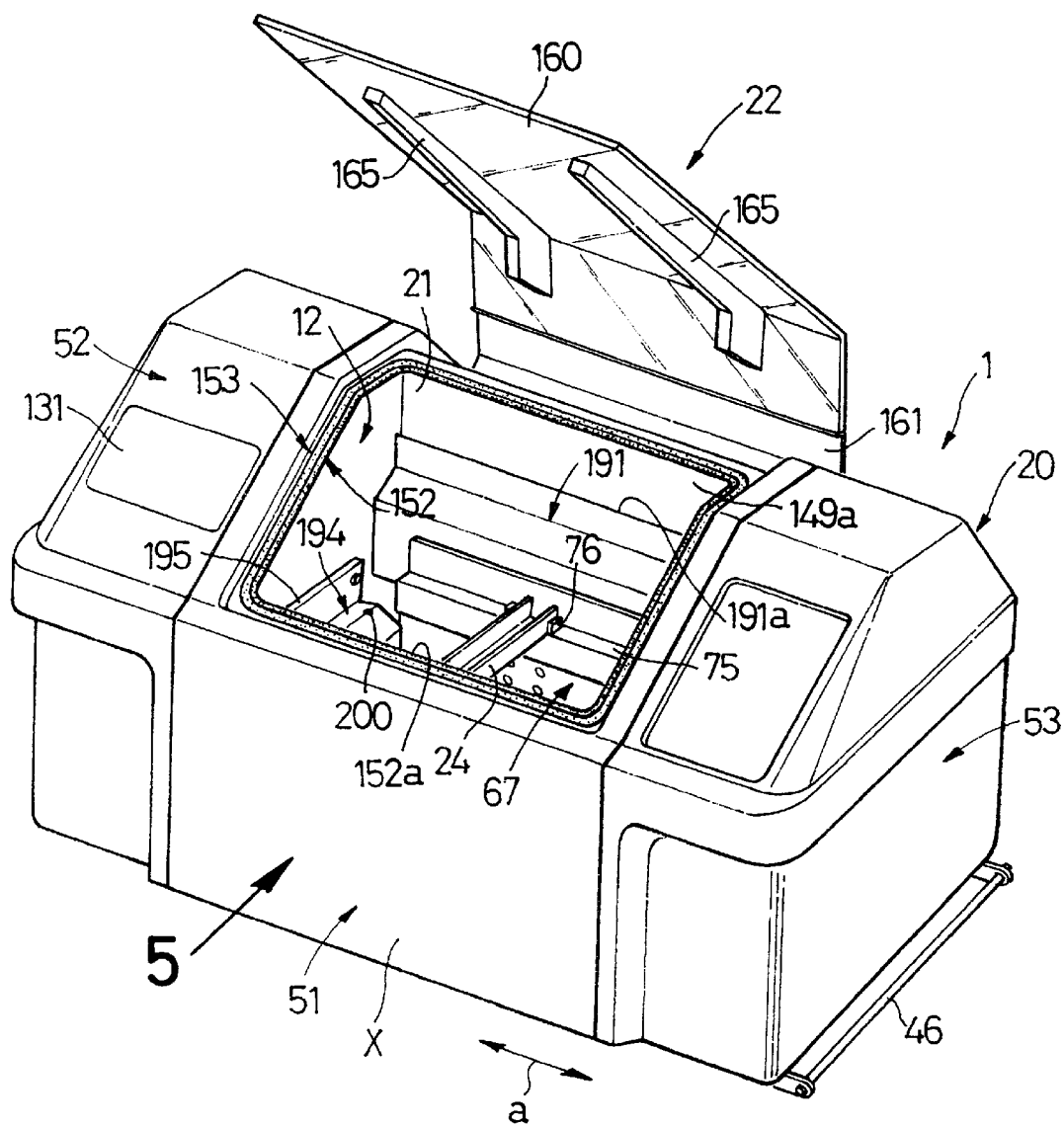
FIG. 4 is a perspective view of an electrolytic test machine.
Figure 5:
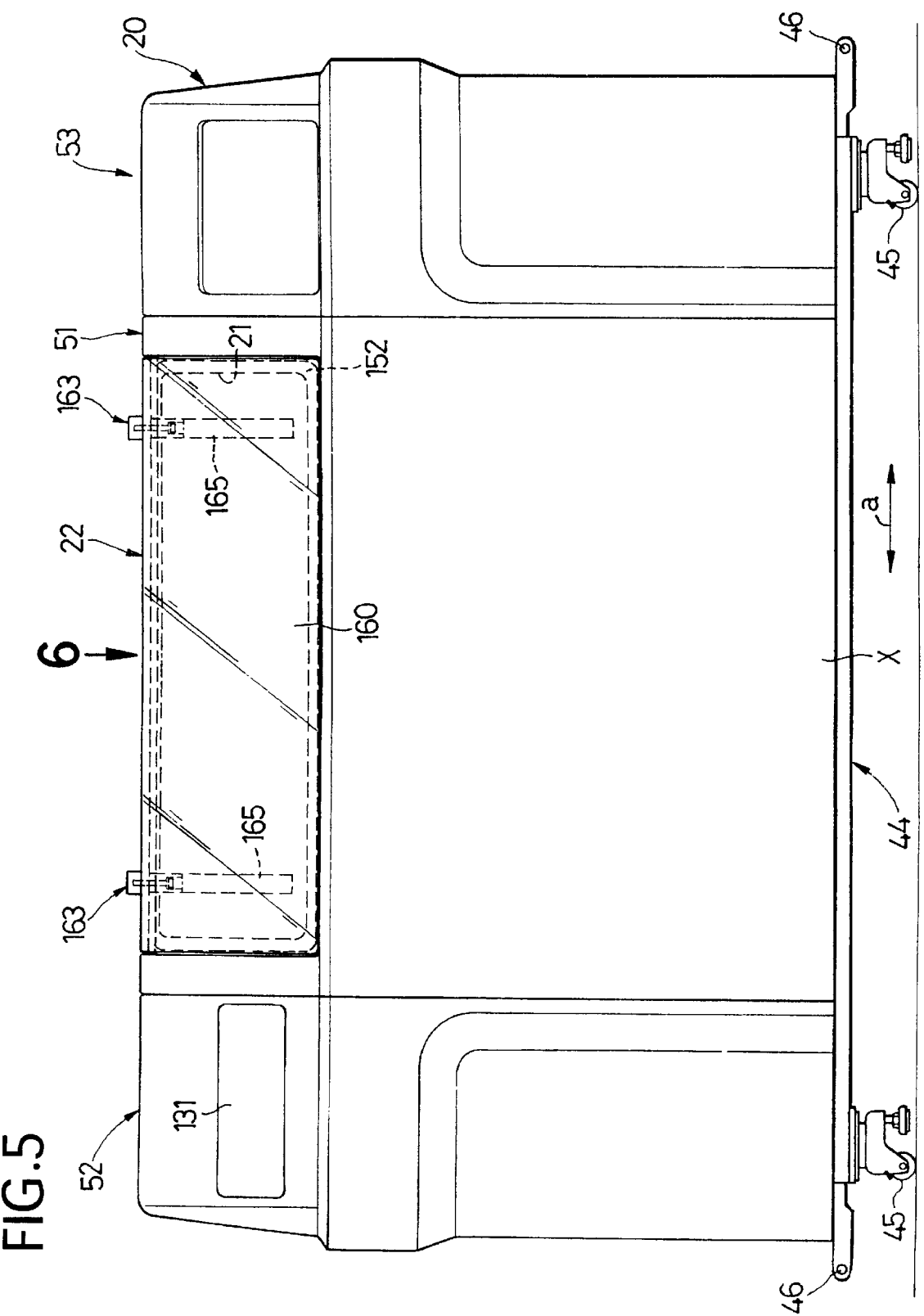
FIG. 5 is a front view of the electrolytic test machine, taken along an arrow 5 in FIG. 4.

As best shown in FIGS. 4 to 6, a message provided by the message indicating means 129 is displayed by characters on a liquid crystal display plate 131 mounted on the upper surface of the left cover section 52 which covers the control section C. The prohibiting means 130 is operated to maintain the DC power source 9 in its OFF state. Thus, the testing operator can reliably know the timing of replacement of the carbon electrode 13.

As shown in FIG. 23, the determining device 123 is constructed, so that the device 123 is not operated after replacing the electrode 13 unless the device 123 is reset to bring the integration used current amount $C_3$ in the memory means 127 into 0.

If the effective current amount $C_1$ and the integration used current amount $C_3$ are in a relation of $C_1 \geq C_3$ in starting the test, the test is started, and the calculation and the integration of the used current amount $C_2$ and the like are carried out.

The determining device 123 includes a second calculating means $132_2$ for subtracting the integration used current amount $C_3$ from the effective current amount $C_1$ in the carbon electrode 13 to determine a remaining effective current amount $C_4$, and a remaining effective current indicating means 133 for indicating the remaining effective current amount $C_4$.

Figure 24:
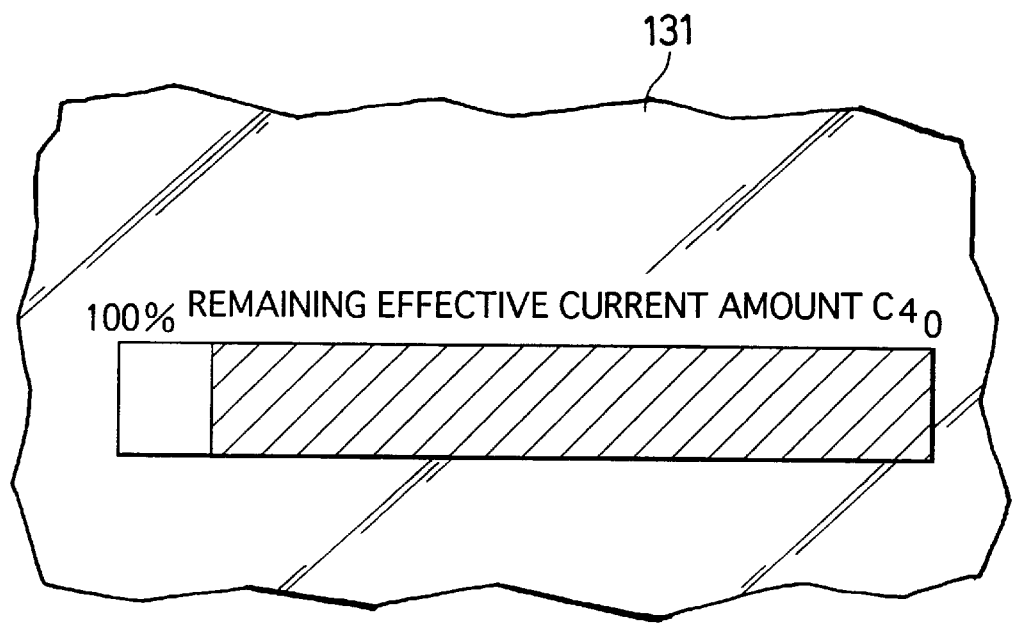
FIG. 24 is a diagram for explaining a remaining effective current amount Indicating portion.

The second calculating means $132_2$ calculates the remaining effective current amount $C_4$ according to $C_4 (\%) = \{1 - (C_3/C_1)\} \times 100$. The remaining effective current amount $C_4$ indicated by the remaining effective current indicating means 133 is indicated by a bar graph on the liquid crystal display plate 131, so that the remaining effective current amount $C_4$ is gradually decreased, as shown in FIG. 24. Thus, it is possible for the testing operator to easily know the remainder of the service life of the carbon electrode 13 and the situation of variation thereof.

When the effective current amount $C_1$ and the integration used current amount $C_3$ are in a relation of $C_1 \leq C_3$, the remaining effective current amount $C_4$ is displayed as being $C_4 = 0\%$.

[J] Structure of sealing of the opening in the electrolytic cell (FIGS. 6 to 10, 13 and 25 to 27)

As shown in FIG. 10, the heights of the front and rear wall portions 57 and 71 in the peripheral wall 47 of the electrolytic cell 12 are lower than those of the left and right sidewall portions 48 and 49. That part of each of the left and right sidewall portions 48 and 49, which protrudes from the front and rear wall portions 57 and 71, has a vertical front edge 134, a forward declined upper edge 135, a horizontal upper edge 136, a rearward declined upper edge 137 and a vertical rear edge 138. A seal member 139 made of a rubber is mounted on upper edges of the front and rear wall portions 57 and 71 and all the edges 134 to 138 of the left and right sidewall portions 48 and 49, i.e., an entire peripheral edge of the upward-turned opening 19.

Figure 25:
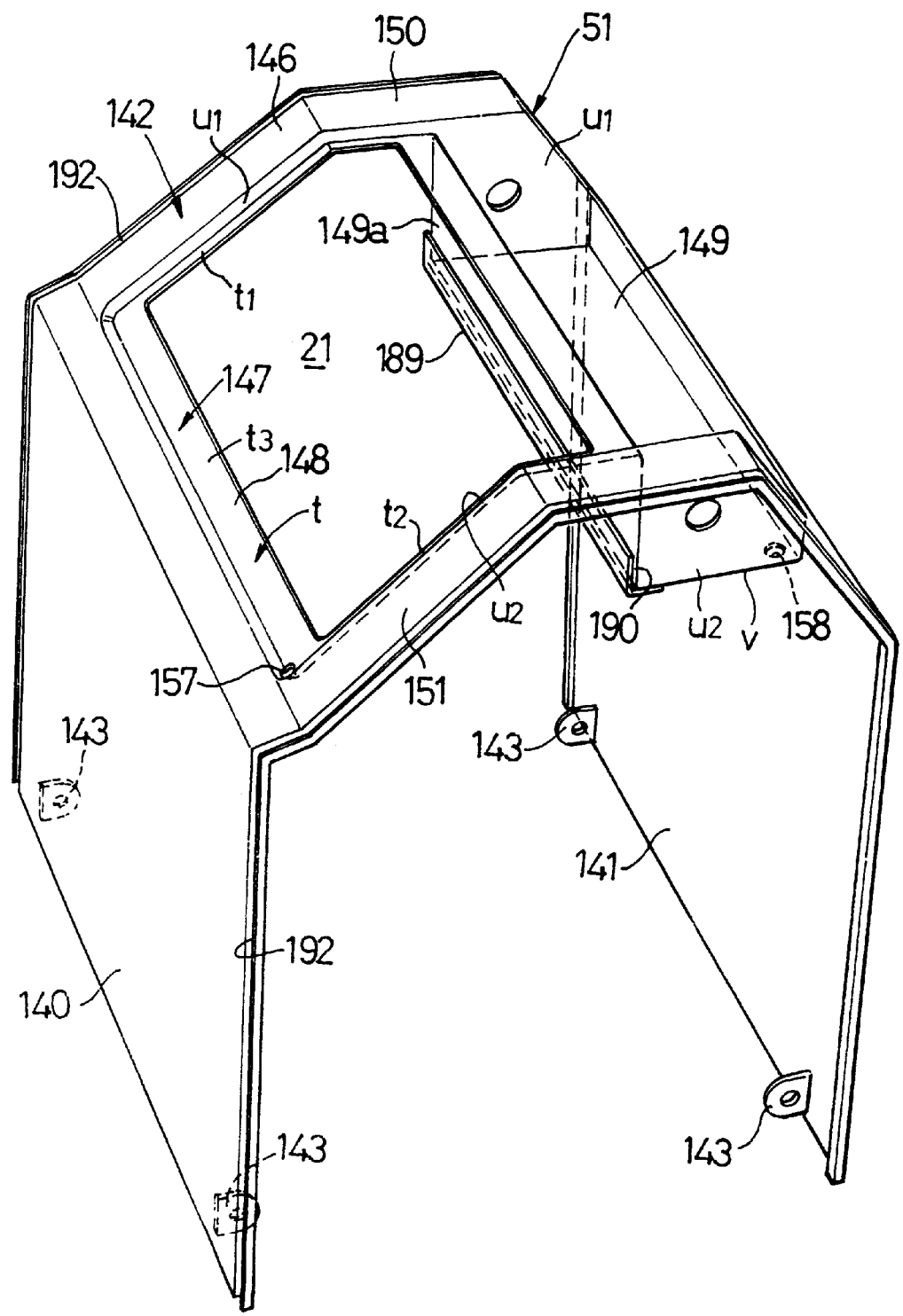
FIG. 25 is a perspective view of a central cover section.

As best shown in FIG. 25, the central cover section 51 is comprised of a front wall 140, a rear wall 141 and an upper wall 142 which connects the front and rear walls 140 and 141 to each other. The central cover section 51 is placed over the electrolytic cell 12 from above the electrolytic cell 12. Thus, the front, upper and rear portions of the electrolytic cell 12 are covered with the central cover section 51. As shown in FIGS. 8, 9 and 25, inward-turned projecting pieces 143 are provided on right and left ends of lower portions of inner surfaces of the front and rear walls 140 and 141. The projecting pieces 143 at the right end are detachably mounted to front and rear angle members 144 extending vertically to form the frame 90 of the machine base 44. The projecting pieces 143 at the left end are detachably mounted to front and rear angle members 145 extending vertically of the machine base 44.

As best shown in FIGS. 6, 10 and 25, the upper wall 142 has an outer peripheral frame-like section 146, and a recess 147 surrounded by the outer peripheral frame-like section 142. The recess 147 is comprised of a relatively large and shallow recess portion 148 located on a front side, and a relatively small and deep recess portion 149 located on a rear side. The upward quadrilateral opening 21 for placing and removing the test material 2 into and out of the electrolytic cell 12 is provided in a bottom wall t of the shallow recess portion 148.

Each of left and right portions 150 and 151 of the outer peripheral frame-like section 146 has a shape extending along the forward-declined upper edge 134, the horizontal upper edge 136 and the rearward-declined upper edge 137 in the left and right sidewall portions 48 and 49 of the electrolytic cell 12, as shown in FIG. 10. In addition, each of left and right portions t₁ and t₂ of the bottom wall of the shallow recess portion 148 has a shape extending along portions of the forward-declined upper edge 135 and the horizontal upper edge 136.

As best shown in FIGS. 7, 10, 25 and 26, left and right sidewalls u₁ and u₂ of the recess 147 are fitted between the left and right sidewall portions 48 and 49 of the electrolytic cell 12. Thus, lower surfaces of the left and right portions 150 and 151 of the outer peripheral frame-like section 146 are brought into close contact with the upper surface of the seal member 139 at portions of the forward-declined upper edge 135, the horizontal upper edge 136 and the rearward-declined upper edge 137 of the left and right sidewalls 48 and 49. In addition, outer surface of the left and right sidewalls u₁ and u₂ of the recess 147 are brought into close contact with the inner surface of the seal member 139 at the vertical front edge 134, the forward-declined upper edge 135, the horizontal upper edge 136, the rearward-declined upper edge 137 and the vertical rear edge 138 of the left and right sidewalls 48 and 49.

Further, as best shown in FIGS. 7, 10, 13 and 27, a lower surface of a front portion t₃ of the bottom wall of the shallow recess portion 148 is brought into close contact with the upper surface of the seal member 139 at the front wall portion 57 of the electrolytic cell 12, and a lower surface of a bottom wall v of the deep recess portion 149 is brought into close contact with the upper surface of the seal member 139 at the rear wall portion 71 of the electrolytic cell 12.

In this way, when the central cover section 51 is placed over the electrolytic cell 12 from above the electrolytic cell 12 and mounted to the machine base 44, the opening 19 in the electrolytic cell 12 can be reliably sealed.

[K] Structure for opening and closing lid and structure for collecting water drops deposited on inner surface of lid (FIGS. 4 to 7, 9, 13, 14 and 25 to 28)

Figure 26:
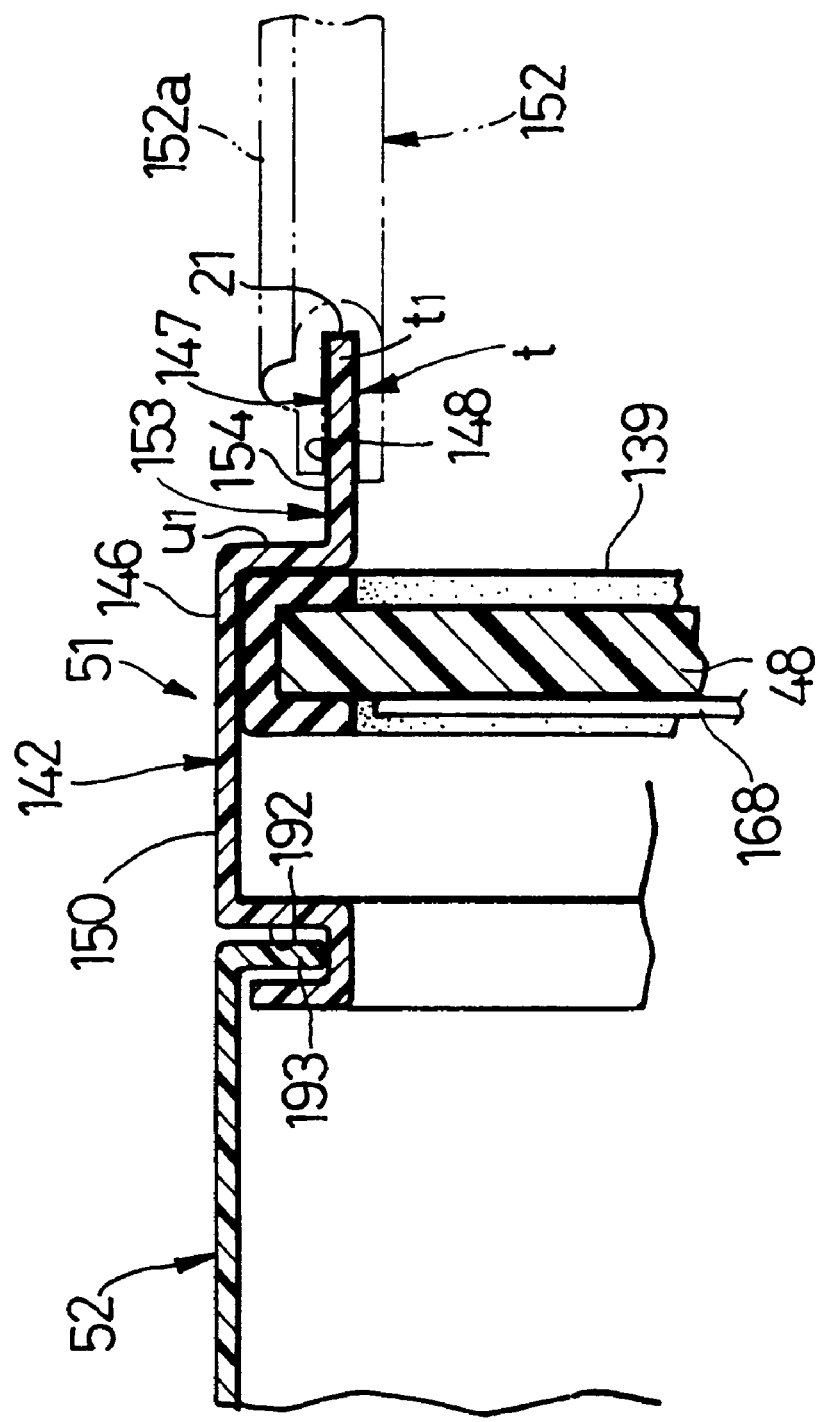
FIG. 26 is a sectional view taken along a line 26—26 in FIG. 6.
Figure 27:
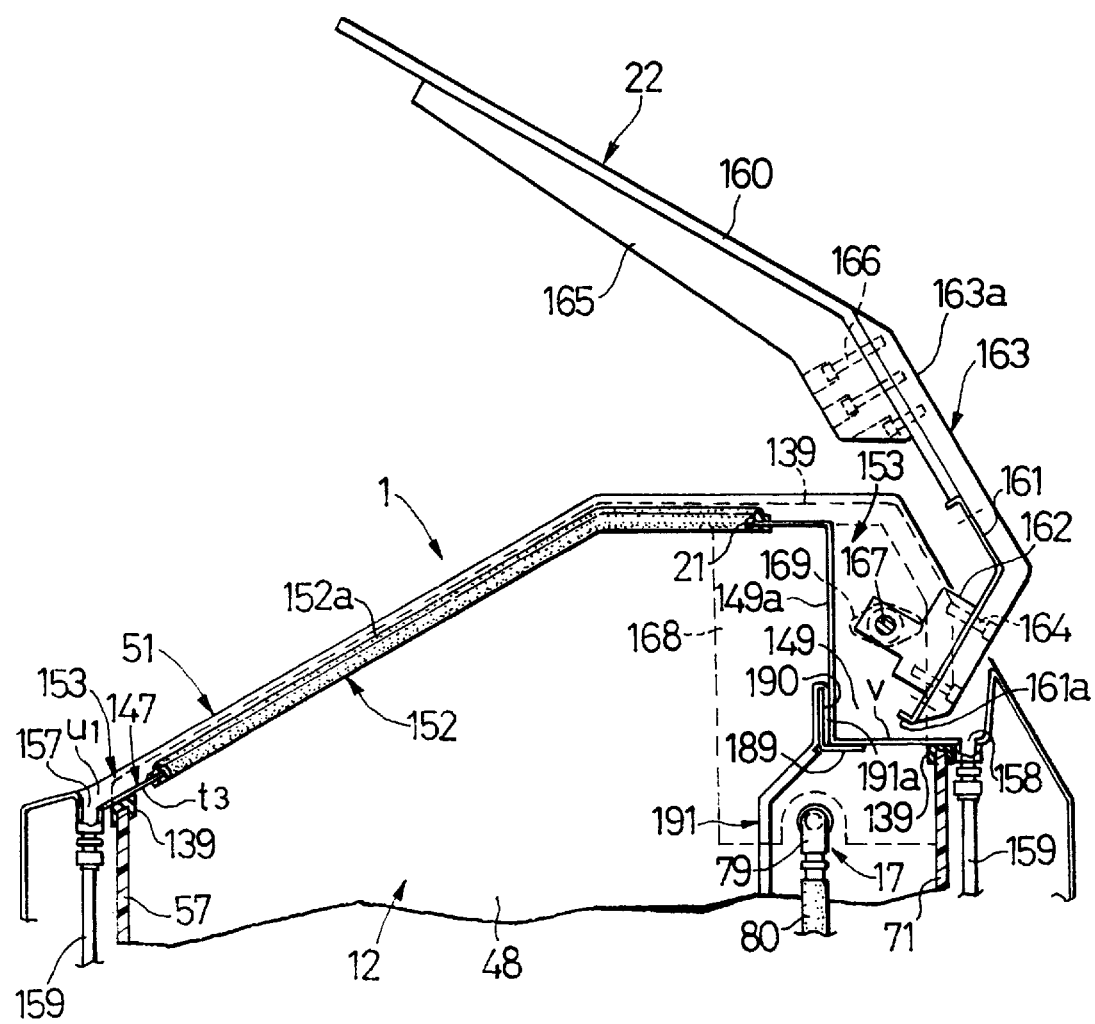
FIG. 27 is a sectional view taken along a line 27—27 in FIG. 6.

As shown in FIGS. 4, 6, 26 and 27, an annular seal member 152 is mounted to that entire peripheral edge of the upper wall 142 of the central cover section 51 which defines the upward opening 21. The annular seal member 152 includes an annular lip 152a which protrudes from an upper surface of the annular seal member 152 and surrounds the opening 21. Thus, an annular tub 153 is formed by cooperation of the annular seal member 152, the shallow recess portion 148 and the deep recess portion 149 with one another and located outside the annular seal member 152 to surround the annular seal member 152. The substantially wholes of left and right grooves 154 and 155 in the annular tub 153 are forward declined, and a front groove 156 in the annular tub 153 assumes a V-shape. As best shown in FIGS. 6, 14 and 27, drainage ports 157 and 158 are opened in right ends of bottoms of the front groove 156 and the rear deep recess portion 149 and connected to a downstream portion of the drainage pipe line 18 from the manual cock 32 through a tube 159.

As best shown in FIGS. 4, 5, 13 and 27, the lid 22 for opening and closing the opening 21 includes a transparent synthetic resin plate 160 located in a front side and forming a main body of the lid 22, and a steel plate 161 made of a stainless steel, which is mated to a rear edge of the plate 160. As best shown in FIGS. 6 and 13, when the opening 21 has been closed, the transparent synthetic resin plate 160 covers the substantially entire shallow recess portion 148, with its inner surface put in close contact with the annular lip 152a of the annular seal member 152, and the steel plate 161 covers the substantially entire deep recess portion 149, with its rear edge 161a located in the vicinity of an opening of the deep recess portion 149. Namely, the substantially entire annular tub 153 is covered with the lid 22.

A pair of brackets 162 made of a stainless steel and disposed at a predetermined distance on an inner surface of the steel plate 161 and a pair of reinforcing rib members 163 made of a stainless steel and disposed on an outer surface of the steel plate 161 are coupled to each other with the steel plate 161 interposed therebetween by a plurality of bolts 164. Protrusion 163a of the reinforcing rib members 163 which are disposed on an outer surface of a rear portion of the transparent synthetic resin plate 160 to project forwards from the steel plate 161 are coupled to rear portions of a pair of reinforcing rib members 165 made of a synthetic resin and disposed on an inner surface of the main plate 160, with the transparent synthetic resin plate 160 interposed therebetween, by a plurality of bolts 166. A front portion of each of the reinforcing rib members 165 is bonded to the transparent synthetic resin plate 160.

As best shown in FIGS. 6, 7 and 9, a support shaft 167 for the lid extends laterally in a substantially central area of the deep recess portion 149 in such a manner that its opposite ends are passed through the left and right sidewalls u₁ and u₂ of the recess 147 and the left and right sidewall portions 48 and 49 of the electrolytic cell 12 and turnably supported on bearings 169 on outer surfaces of reinforcing plates 168 made of a steel and mounted on the outer surfaces of the left and right sidewall portions 48 and 49. The support shaft 167 is passed through the brackets 162 of the lid 22 and short tubes 170 fixed to the brackets 162, and is coupled in a rotation-prevented manner to the short tube 170.

Figure 28:
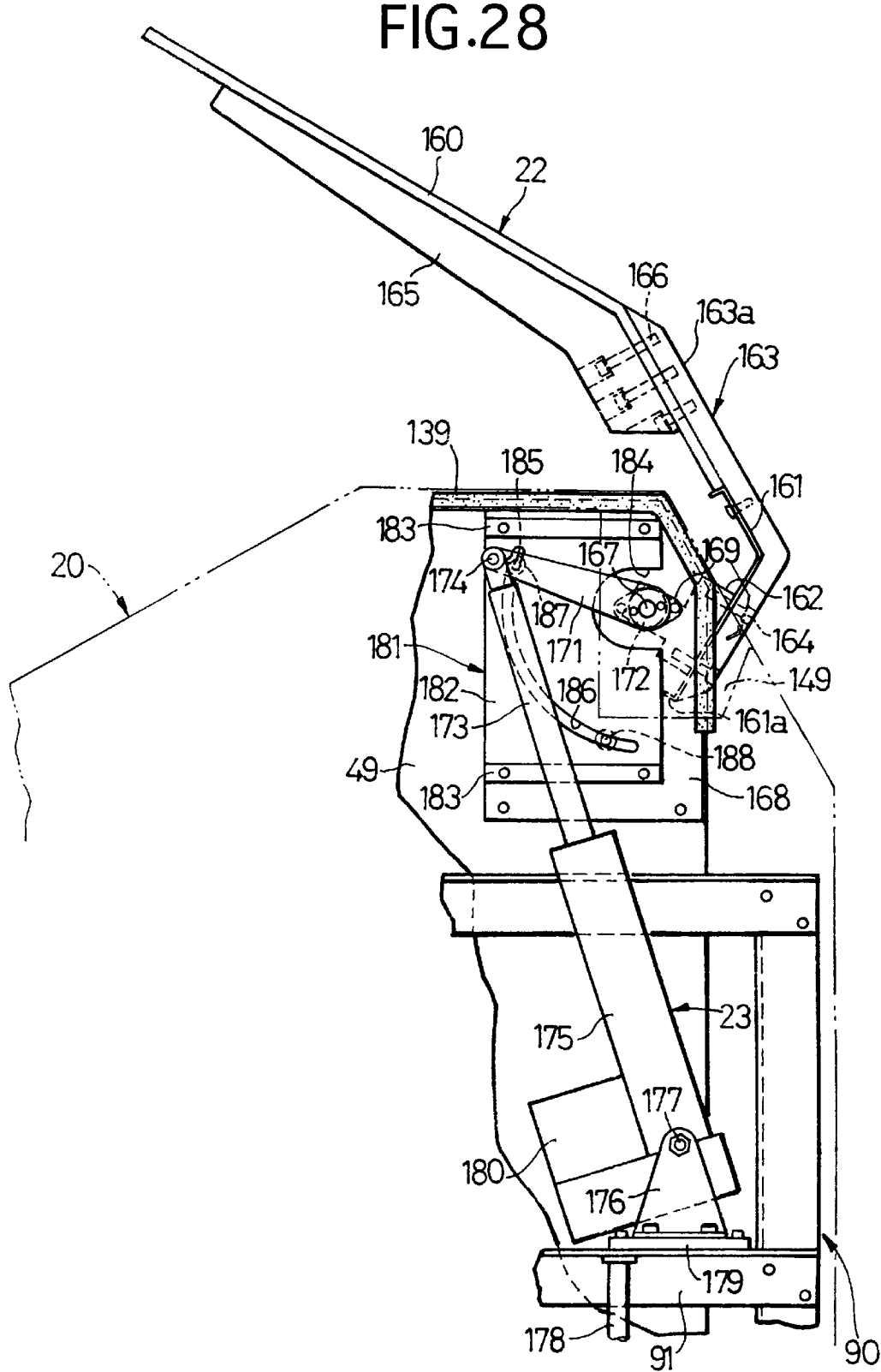
FIG. 28 is a sectional view taken along a line 28—28 in FIG. 7.

As best shown in FIGS. 7, 9 and 28, a right end of the support shaft 167 protruding from the right sidewall portion 49 of the electrolytic cell 12 is passed through an upper end of a link 171 and a short tube 172 fixed to the link 171, and is coupled to the short tube 172 in a rotation-prevented manner. The link 171 is pivotally connected at its lower end through a connecting pin 174 to a piston rod 173 of the electric power cylinder 23 disposed below the link 171.

A cylinder body 175 of the power cylinder 23 is pivotally connected at its lower end to a bifurcated support member 176 of the machine base 44 through a connecting shaft 177. The support member 176 is fixed to a mounting base 179 supported by the lower angle member 91 of the frame 90 and a support pillar 178. The power cylinder 23 includes an electric motor 180 integral with the cylinder body 175.

On the outer surface of the right sidewall portion 49 of the electrolytic cell 12, a guide plate 181 for the link is disposed in an superposed relation to the reinforcing plate 168. The guide plate 181 has L-shaped legs 183 at upper and lower edges of a flat plate portion 182 thereof. The L-shaped legs 183 are mounted to the right sidewall portion 49 through the reinforcing plate 168. The flat plate portion 182 has a notch 184 for avoiding the interference with the support shaft 167, and an arcuate guide bore 186 in which a guide pin 185 projectingly provided on the link 171 is slidably fitted and which extends vertically. Limit switches 187 and 188 are mounted to an inner surface of the flat plate portion 182 in the vicinity of upper and lower ends of the guide bore 186 and operated by the guide pin 185. The lower limit switch 188 determines a closed position of the lid 22, as shown in FIG. 9, and the upper limit switch 187 determines an opened position of the lid 22, as shown in FIG. 28. When the opening 21 is opened, one end of the lid 22 on the side of its rotational center, e.g., the rear edge 161a of the steel plate 161 in the illustrated embodiment, is disposed within the deep recess portion 149 of the annular tub 153, as best shown in FIG. 27.

In the corrosion resistance test, the temperature of the aqueous solution of NaCl 11 is risen to about 40° C. as described above and hence, many waterdrops are liable to be deposited onto the inner surface of the transparent synthetic resin plate 160 of the lid 22 closing the opening 21.

With the above construction, many waterdrops deposited on the inner surface of the transparent synthetic resin plate 160 is transmitted along the steel plate 161 upon opening of the lid 22; dropped from the rear edge 161a into and collected in the deep recess portion 149 of the annular tub 153. Waterdrops deposited on the annular seal member 152 and dropped outside the seal member 152 are likewise collected into the annular tub 153. The water collected in the above manner is discharged through the tube 159 into the drainage pipe line 18.

As shown in FIGS. 4, 10, 13, 25 and 27, an L-shaped plate 189 is mounted to a lower portion of the front wall 149a defining the deep recess portion 149 in the central cover section 51, and a fine groove 190 is defined by cooperation of the L-shaped plate 189 and the front wall 149a with each other. An upper folded edge 191a of a cover member 191 covering the heater chamber 68 is engaged in the fine groove 190, and a lower portion 191b of the cover member 191 is fitted into a notch-like recess 67a in a rear surface of the upper surface of the partition plate 67 defining the heater chamber 68, as shown in FIGS. 11 and 13.

[L] Structure of coupling of central cover section and left and right cover sections (FIGS. 6 to 8, 25 and 26)

The structure of coupling the central cover section 51 covering the front, upper and rear portions of the electrolytic cell 12 and the left cover section 52 covering the control section C adjacent to the central cover section 51 is constructed in the following manner: As best shown in FIGS. 25 and 26, a recessed groove 192 is defined in an edge of the central cover section 51 adjacent to the left cover section 52 continuously over the entire periphery thereof, so that it is opened forwards, upwards and rearwards. A projection 193 is formed on an edge of the left cover section 52 adjacent to the central cover section 51 continuously over the entire periphery thereof, so that it is folded inwards.

In a condition in which the central cover section 51 has been fixed to the machine base 44, the left cover section 52 is coupled to the central cover section 51 by bringing the lower ends of the front and rear portions of the projection 193 of the left cover section 52 into engagement with the upper ends of the front and rear portions of the recessed groove 192 in the central cover section 51 to lower the left cover section 52, and then bringing the upper portion of the projection 193 into engagement with the upper portion of the recessed groove 192. The structure of coupling of the central cover section 51 and the right cover section 53 is the same as the above structure.

With such construction, even if the left and right cover sections 52 and 53 pour water upon themselves, the entering of water into the control section C and the mechanical section M can be prevented.

The water entering coupled portions of the central cover section 51 and the left and right cover sections 52 and 53 is received into each of the recessed grooves 192 and discharged downwards.

Further, in carrying out the maintenance of the electrolytic cell 12, the mechanical section M and the control section C, the left and right cover sections 52 and 53, if they are lifted, can be removed from the central cover section 51. On the other hand, as described above, it is also simple to couple the left and right cover sections 52 and 53 to the central cover section 51. In addition, the removing and attaching operations are not required, because no seal member is used at each of the coupled portions.

Thus, in carrying out the maintenance of the electrolytic cell 12, the mechanical section M and the control section C, the workability thereof can be improved.

[M] Chlorine Gas Treating Device (1) Entire structure and Function thereof (FIGS. 4, 7 to 11, 13, 14 and 29 to 32)

At the coating film peeling-off step in the corrosion resistance test, a chlorine gas is generated on the side of the carbon electrodes 13 in response to the electrolysis of the aqueous solution of NaCl 11 due to the fact that the polarity of the carbon electrodes 13 is set at the positive.

The chlorine gas treating device 6 is mounted in the electrolytic test machine 1 to purify the chlorine gas, and has a function to collect the chlorine gas generated in response to the electrolysis of the aqueous solution of NaCl 11, out of the aqueous solution of NaCl 11 together with a part of the aqueous solution of NaCl 11, a function to decompose NaClO which is a product of reaction of the chlorine gas and the aqueous solution of NaCl, thereby producing NaCl, and a function to return the NaCl to the electrolytic cell 12.

The chlorine gas treating device 6 will be described more specifically below. As shown in FIGS. 4, 7, 8, 10, 11 and 13, a chlorine gas (harmful gas) collecting hood 194 is placed on the partition plate 54 and the division plate 56 in the left electrode chamber 55. A mounting plate 195 integral with the hood 194 is screwed to the left sidewall portion 48 of the electrolytic cell 12. As best shown in FIGS. 7 and 11, the hood 194 covers the entire upper portion of the carbon electrode 13 and closes the upward opening 55a in the electrode chamber 55. The hood 194 includes a box-like hood body 196 placed on the partition plate 54 and the division plate 56, and a roof-like portion 197 integral with the hood body 196 and assuming an angle shape in cross section. A lower surface of the roof-like portion 197, namely, a lower ridgeline 199, is inclined at an angle $\alpha \geq 1$ degree, so that its rear end which is one end is located at a higher location than its front end which is the other end. A through-hole 200 is defined in the rear end of the roof-like portion 197 for venting air within the electrode chamber 55 at the start of the supplying of water into the electrolytic cell 12.

Figure 29:
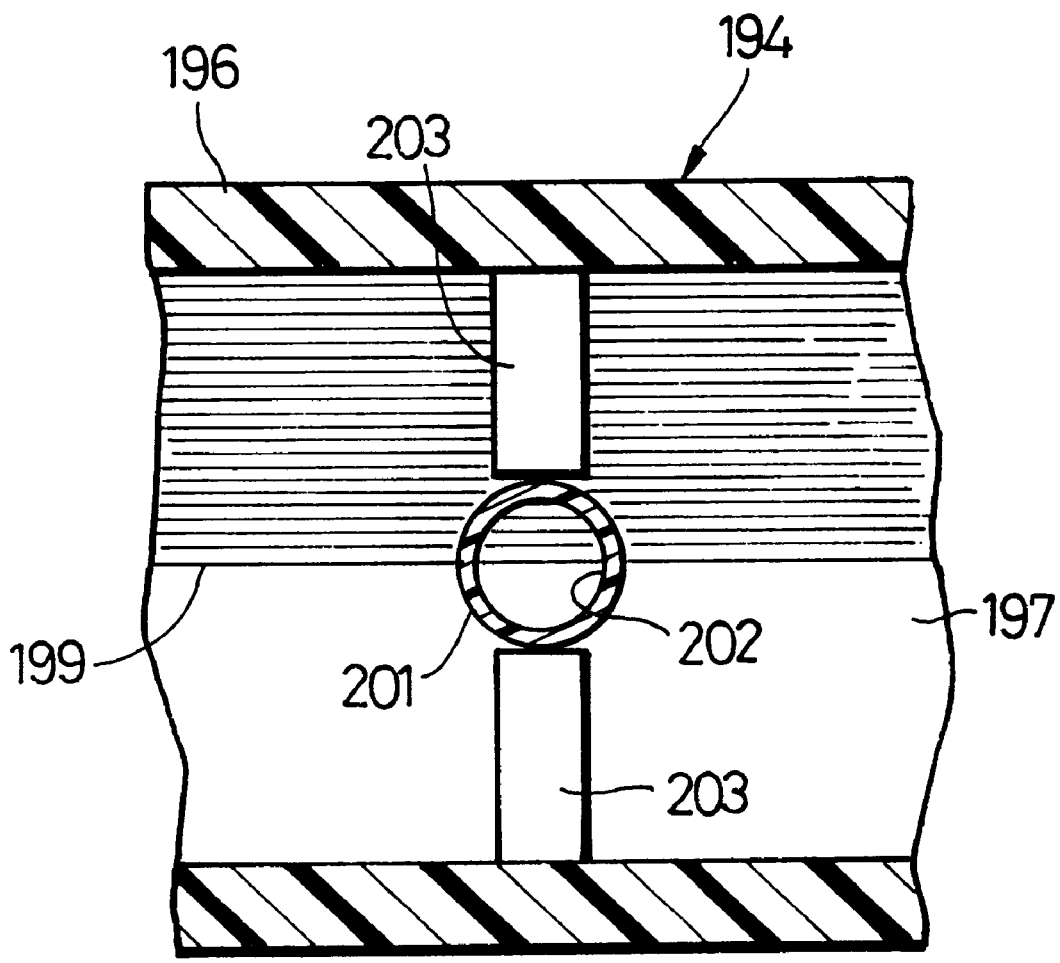
FIG. 29 is a sectional view taken along a line 29—29 in FIG. 11.

The sucking side of the treating pipe line 33 is passed through the bottom wall 83 of the electrolytic cell 12, and a sucking pipe 201 which is a terminal end of the treating pipe line 33 is risen within the electrode chamber 55. The sucking pipe 201 has a suction port 202 which is disposed in proximity to a higher location of the ridgeline 199 of the roof-like portion 197 and inclined forwards and toward the ridgeline 199 in order to smoothly suck the chlorine gas. As best shown in FIGS. 7, 11 and 29, a pair of baffles 203 are provided on the hood 194 over opposed inner surfaces of the hood body 196 and the lower surface of the roof-like portion 197 to lie on opposite sides of the suction port 202. The baffles 203 act to prevent the chlorine gas (harmful gas) from keeping out of the suction port 202 and flowing toward the air venting through-hole 200.

The suction pipe 201 extends along the rear surface of the protruding plate 61 located on the left sidewall portion 48 of the electrolytic cell 12. The suction pipe 201 is fitted into a through-hole 205 in an annular member 204 projectingly provided on an upper portion of the rear surface of the protruding plate 61, and is fixed in a stationary state in the electrolytic cell 12.

A chlorine gas collecting hood 194 and a suction pipe 201 similar to those described above and the like are also provided in the right electrode chamber 55. Therefore, in the right electrode chamber 55, like reference characters are affixed to portions or components similar to those of the left electrode chamber 55.

As best shown in FIGS. 7, 8 and 14, the treating pipe line 33 including the two suction pipes 201 extends from the inside of the machine base 44 via mechanical section M along the outer surface of the rear wall portion 71 of the electrolytic cell 12, and is finally bifurcated, wherein two discharge ports 206 open into portions of the rear wall portion 71 of the electrolytic cell 12 in which the aqueous solution of NaCl 11 is stored.

As best shown in FIGS. 9 and 14, the suction pump 34 is disposed in the treating pipe line 33 in the mechanical section M. On the side of the outlet of the suction pump 34 in the treating pipe line 33, the chlorine gas purifying device 35 is disposed upstream, and the flow rate sensor 36 for detecting an abnormality of the treating system is disposed downstream. The suction pump 34 is mounted to a support member 207 on the machine base 44, and the chlorine gas purifying device 35 is mounted on a support 208 on the machine base 44. The suction pump 34 has a suction port 209 in its lower end face, and a discharge port 210 in a lower end of its outer peripheral surface.

A drainage pipe 211 diverges from the treating pipe line 33 at a location adjacent to the suction side of the suction pump 34. The drainage pipe 211 has a manual cock 212 at its intermediate portion and is connected to the drainage pipe line 18 at a location downstream from the manual cock 32. The drainage pipe 211 is located at a level lower than the suction pump 34 and the chlorine gas purifying device 35. Thus, it is possible to withdraw water from the suction pump 34 and the chlorine gas purifying device 35.

The chlorine gas purifying device 35 includes a filter and a catalyst therein. The catalyst has a function to adsorb the chlorine gas and to decompose NaClO which is a reaction product of the chlorine gas and the aqueous solution of NaCl 11, thereby producing NaCl. The NaClO whitens the coating film 4 by its bleaching effect, so that the appearance of the coating film 4 is significantly different from a corroded state provided in a natural environment. Therefore, the NaClO is a harmful compound in the corrosion resistance test.

If the chlorine gas treating device is constructed in the above manner, the chlorine gas generated around the carbon electrodes 13 immersed in the aqueous solution of NaCl 11 in the electrolytic cell 12 is immediately collected out of the aqueous solution of NaCl 11 together with a part of the aqueous solution of NaCl 11; then purified by the chlorine gas purifying device 35. Thereafter, the aqueous solution of NaCl 11 is returned to the electrolytic cell 12.

In this case, the foamy chlorine gas generated in the vicinity of each of the carbon electrodes 13 is floated up in the aqueous solution of NaCl 11 and smoothly introduced in the form of a foam to the suction port 202 by a guide effect of the chlorine gas collecting hood 194. In addition, the chlorine gas is sucked with a good efficiency through the suction port 202 into the treating pipe line 33 by effects of the baffles 203 for preventing the gas from keeping out of the suction port. Further, the generated chlorine gas cannot be accumulated within the hood 194 sucked by virtue of the inclination of the lower surface of the hood 194, and the accumulated chlorine gas cannot be sucked and hence, the suction pump 34 cannot intake air.

Thus, the diffusion of the chlorine gas into the aqueous solution of NaCl 11 is inhibited. Therefore, it is possible to inhibit the production of NaClO in the aqueous solution of NaCl 11 and the dissolution of the chlorine gas into the aqueous solution of NaCl 11 to the utmost.

Figure 30:
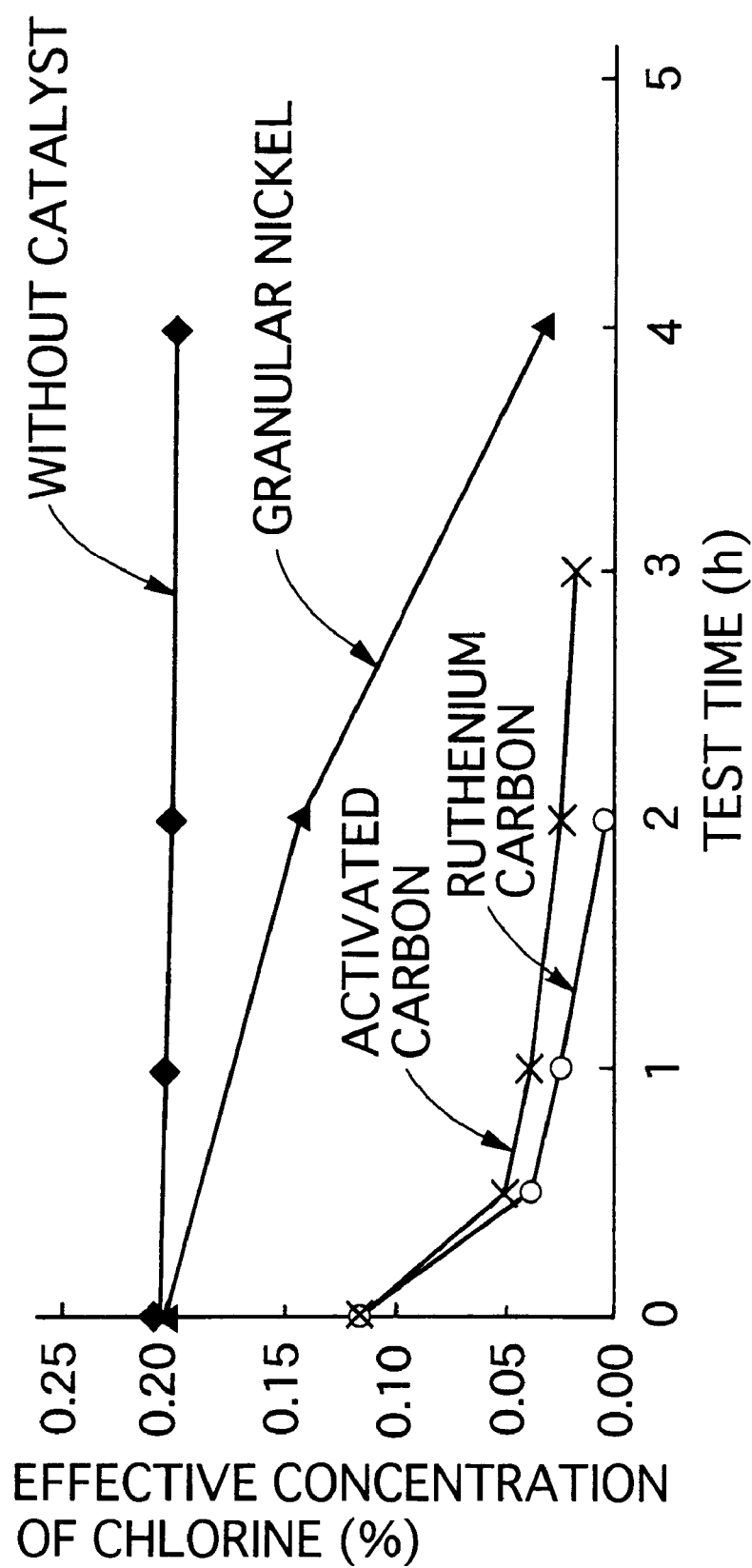
FIG. 30 is a graph illustrating a first example of the relationship between the test time and the effective concentration of chlorine.

FIG. 30 illustrates the relationship between the test time and the effective concentration of chlorine with regard to activated carbon, ruthenium carbon and granular nickel serving as a catalyst used in the chlorine gas purifying device 35. In FIG. 30, the term "effective concentration of chlorine" indicates a determined amount of chlorine gas dissolved in the aqueous solution of NaCl 11 (see JIS K1425). In measuring the effective amount of chlorine, a procedure was employed which involves continuously supplying an electric current at 50 A for 20 hours while maintaining the temperature of the aqueous solution of NaCl 11 at 45° C., sampling 200 cc of the aqueous solution of NaCl 11, throwing the catalyst into the sampled aqueous solution of NaCl maintained at 45° C., and determining the effective concentration of chlorine every after a lapse of a predetermined time. As apparent from FIG. 30, the activated carbon and the ruthenium carbon having an excellent effective chlorine decomposing capability are effective as the catalyst used in the chlorine gas purifying device 35.

Figure 31:
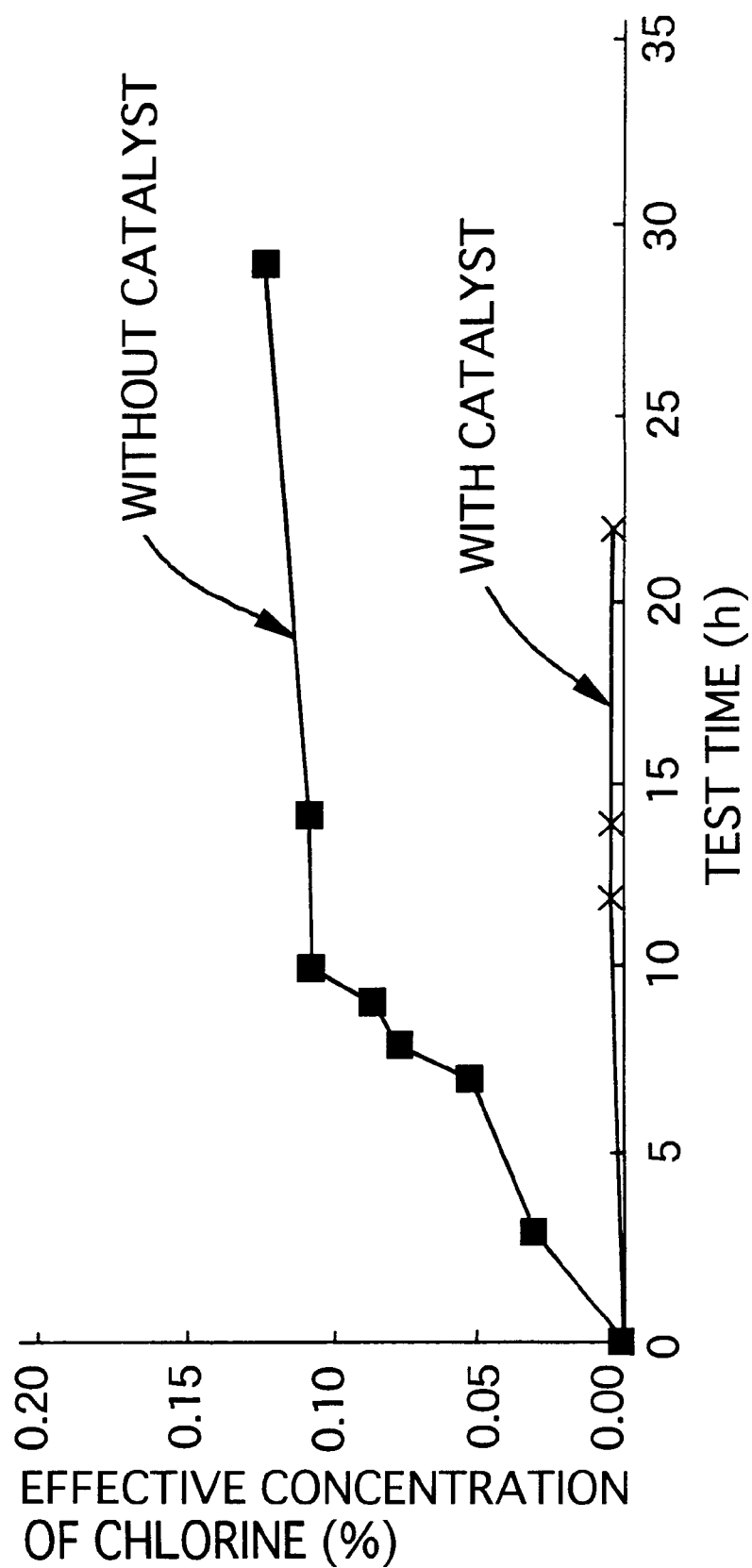
FIG. 31 is a graph illustrating a second example of the relationship between the test time and the effective concentration of chlorine.

FIG. 31 illustrates the relationship between the test time and the effective concentration of chlorine when the activated carbon was used as the catalyst. Conditions for the test are such that an electric current of 50 A is supplied continuously, and the temperature of the aqueous solution of NaCl 11 is 45° C. As apparent from FIG. 31, if the above-described treating device 6 is used, and the activated carbon is used as the catalyst, the effective concentration of chlorine can be maintained at an extremely low value such as about 0.003% or lower, even after the test time exceeds 20 hours.

Figure 32:
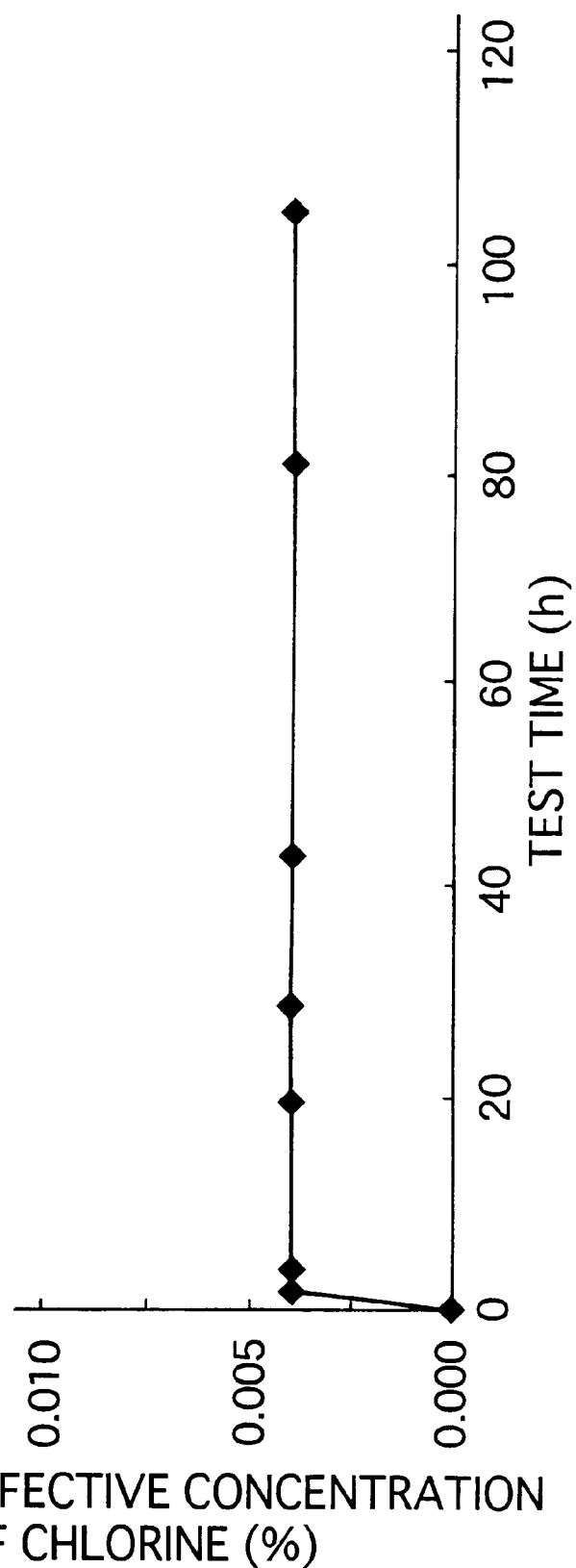
FIG. 32 is a graph illustrating a third example of the relationship between the test time and the effective concentration of chlorine.

FIG. 32 illustrates the relationship between the test time and the effective concentration of chlorine when an electric current of 20 A was continuously supplied at a temperature of the aqueous solution of NaCl 11 equal to 45° C. Even in this case, the effective concentration of chlorine can be maintained at about 0.004% or lower, even after the test time exceeds 100 hours.

As a result of the various tests, it was confirmed that if the effective concentration of chlorine is equal to or lower than 0.005%, the whitening of the coating film 4 does not occur.

In the treating device 6, the flow rate of the aqueous solution of NaCl 11 flowing downstream from the chlorine gas purifying device 35 is measured by the flow rate sensor 36. Therefore, for example, if the chlorine gas purifying device 35 is not clogged and is normal, the flow rate sensor 36 measures a corresponding flow rate. On the other hand, if the clogging of the chlorine gas purifying device 35 is produced, the flow rate is decreased more than that when the chlorine gas purifying device 35 is normal. Therefore, the flow rate sensor measures such a decreased flow rate.

With the above-described construction, an abnormality of the treating system can be easily and reliably detected. In addition, since the flow rate sensor 36 is disposed downstream from the chlorine gas purifying device 35, so that a fine foreign matter entering the treating pipe line 33 is caught by the chlorine gas purifying device 35, the operation of the flow rate sensor 36 cannot be obstructed by the foreign matter. Thus, the accuracy of the flow rate sensor 36 can be maintained over a long period.

(2) Abnormal-point Detector in Treating System (FIGS. 4 to 6 and 33 to 35)

Figure 33:
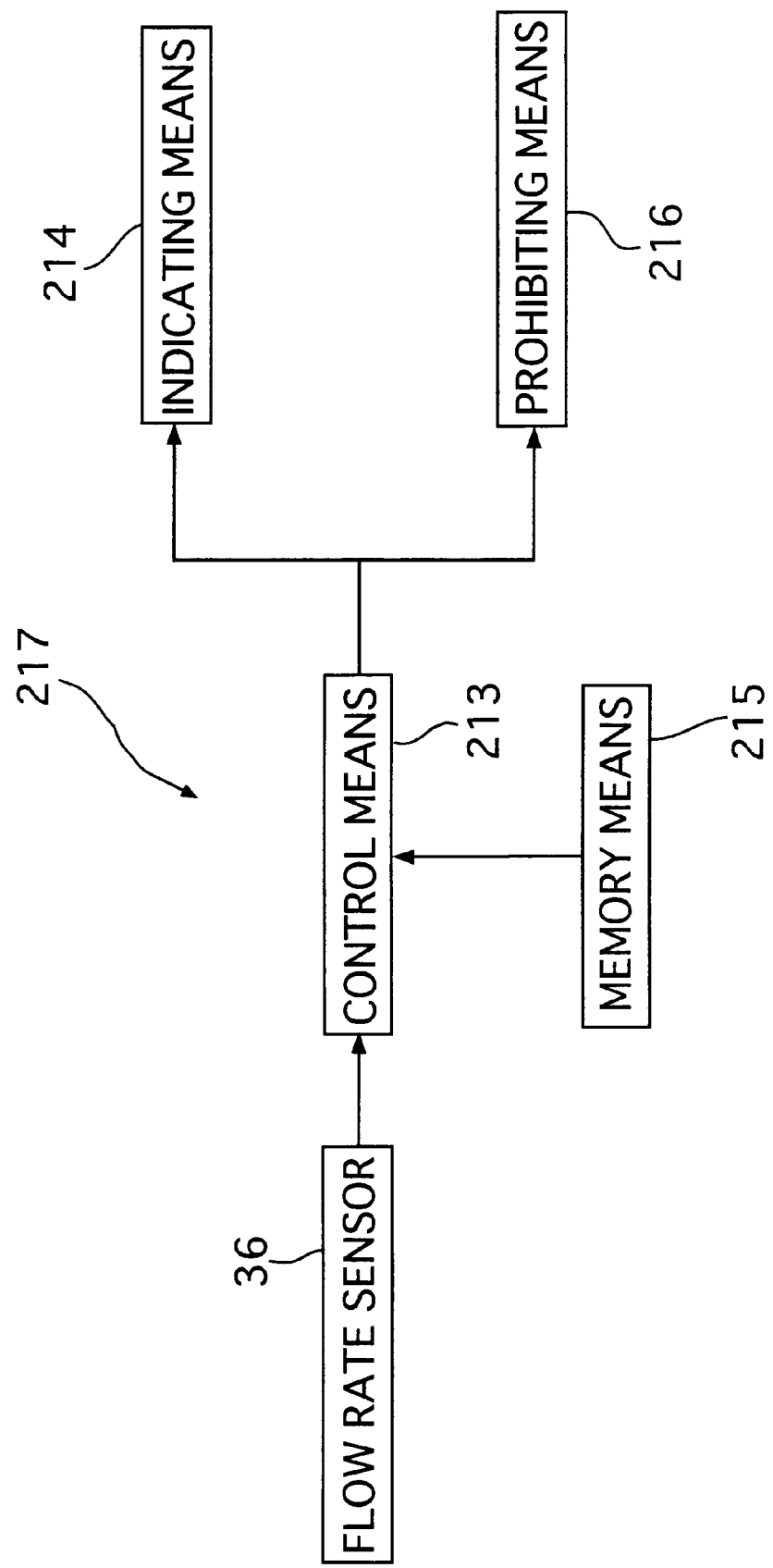
FIG. 33 is a block diagram of an abnormal-point detector in a chlorine gas treating device.

Referring to FIG. 33, the flow rate sensor 36 has a function to transmit an abnormality signal varied depending upon the type of an abnormality of the treating system. A control means 213 is connected to the flow rate sensor 36 and adapted to discriminate the type of the abnormality based on the abnormality signal from the flow rate sensor 36 and transmit an output signal corresponding to the type of the abnormality. An indicating means 214 is connected to the control means 213 for indicating the type of the abnormality in accordance to the output signal from the control means 213.

Figure 34:
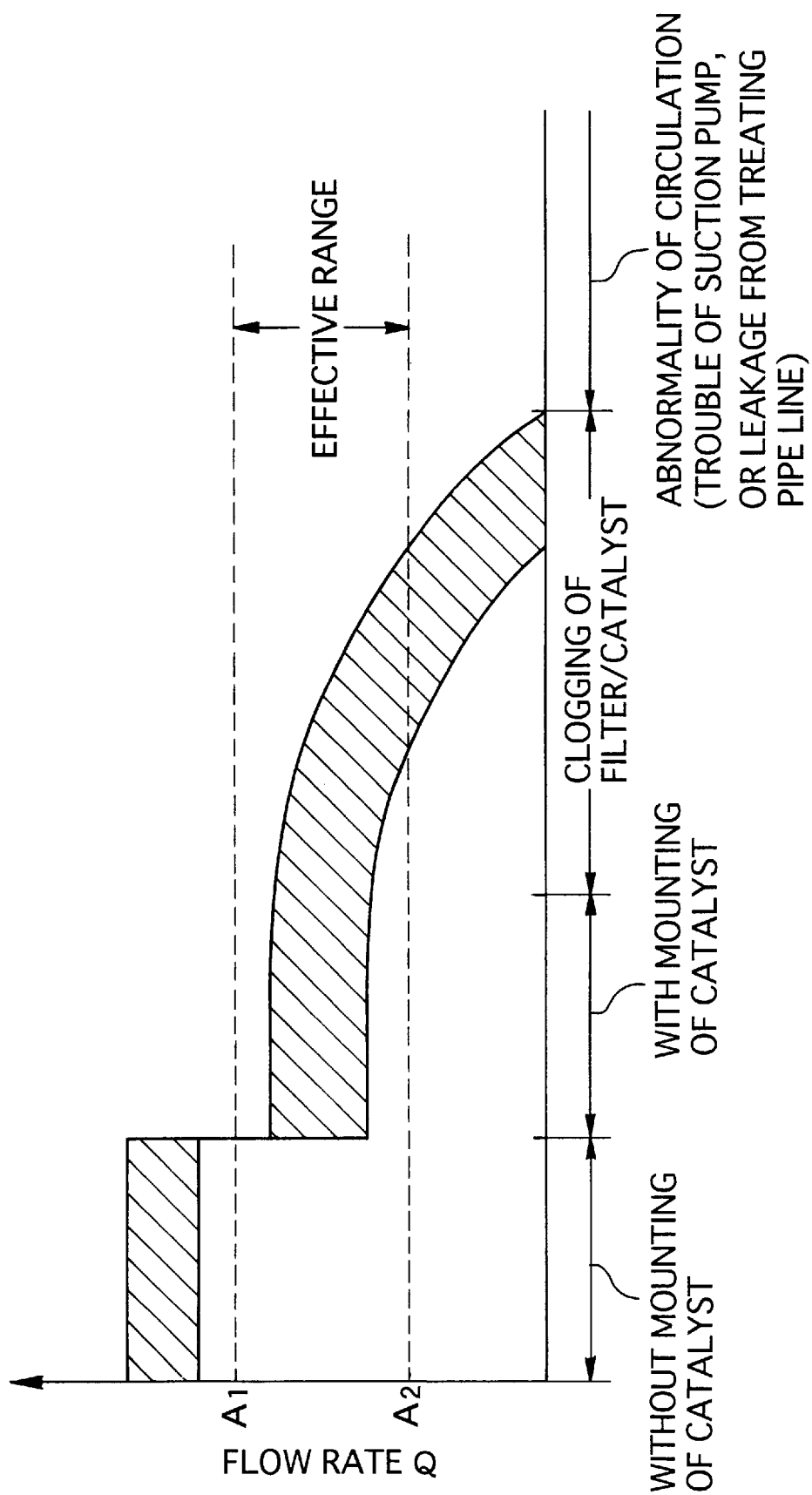
FIG. 34 is a graph illustrating the relationship between the situation of a treating system and the flow rate.

A memory means 215 is connected to the control means 213. An effective range of flow rate Q, namely, $A2 \leq Q \leq A1$ which is a range between an upper limit value A1 and a lower limit value A2 of flow rate, is previously stored in the memory means 215, as shown in FIG. 34. Further, a prohibiting means 216 is connected to the control means 213 for prohibiting the supplying of electric current to the carbon electrodes 13 in accordance with the output signal from the control means 213.

These means 213 to 216 are incorporated in the computer programmed control unit 10 to constitute an abnormal-point detector 217 for the treating system together with the flow rate sensor 36.

The indicating means 214 indicates, for example, a message which is displayed by characters on the liquid crystal display plate 131 on the upper surface of the left cover section 52 covering the control section C, as best shown in FIGS. 4 to 6. The prohibiting means 216 is operated to control the DC power source 9 to its OFF state.

Figure 35:
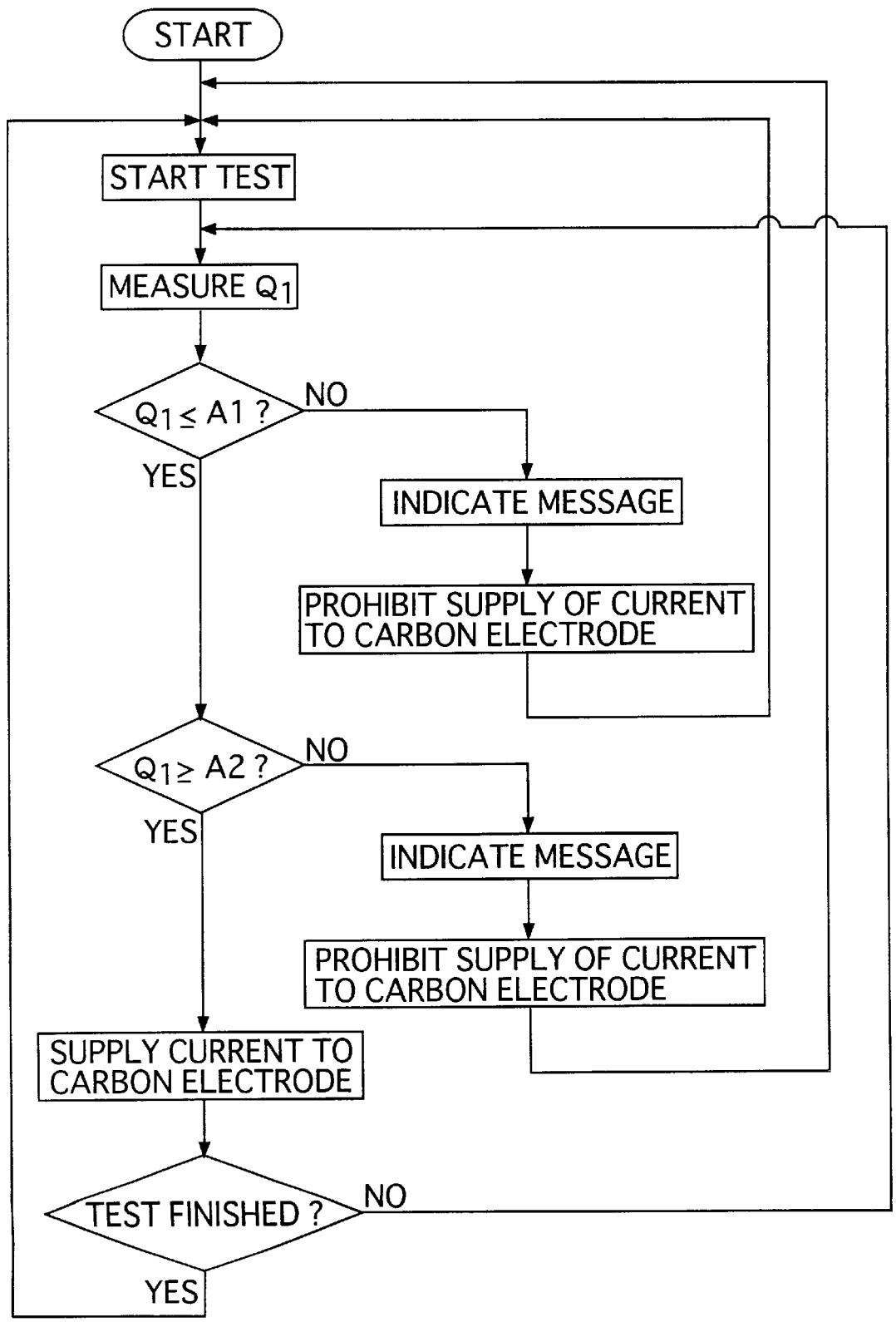
FIG. 35 is a flow chart illustrating the operation of the abnormal-point detector.

As shown in FIGS. 33 and 35, if a signal indicative of a command to start the test is inputted, the flow rate sensor 36 measures a flow rate $Q_1$ of the aqueous solution of NaCl 11 flowing in the treating pipe line 33. If the measured flow rate $Q_1$ is in the effective range of $A2 \leq Q_1 \leq A1$, the control means 213 determines that the flow rate sensor 36 is transmitting a normality signal and thus, the carbon electrodes 13 are energized to start the corrosion resistance test.

If the measured flow rate $Q_1$ is larger than A1, the control means 213 determines that the flow rate sensor 36 is transmitting the abnormality signal, which corresponds to the non-mounting of the catalyst in the chlorine gas purifying device 35, and the control means 213 transmits the corresponding output signal. Thus, a message "stop the test because of the non-mounting of the catalyst" is indicated by the indicating means 214, and the supplying of electric current to the carbon electrodes 13 is prohibited by the prohibiting means 216.

If the flow rate $Q_1$ measured in the flow rate sensor 36 is smaller than A2, operations similar to those described above are carried out. However, a message "stop the test" is indicated by the indicating means 214, because a clogging of the filter or catalyst, a circulation abnormality or the like has been produced.

The abnormal-point detector 217 for the treating system is controlled so that it is operated even during the corrosion resistance test.

The trouble point of the treating system can be easily and reliably detected by the detector 217 to precisely inform a testing personnel of the trouble point, and the detector 217 is relatively inexpensive because of its simple construction.

(3) Chlorine gas purifying device (FIG. 7, 9 and 36 to 38)

Figure 36:
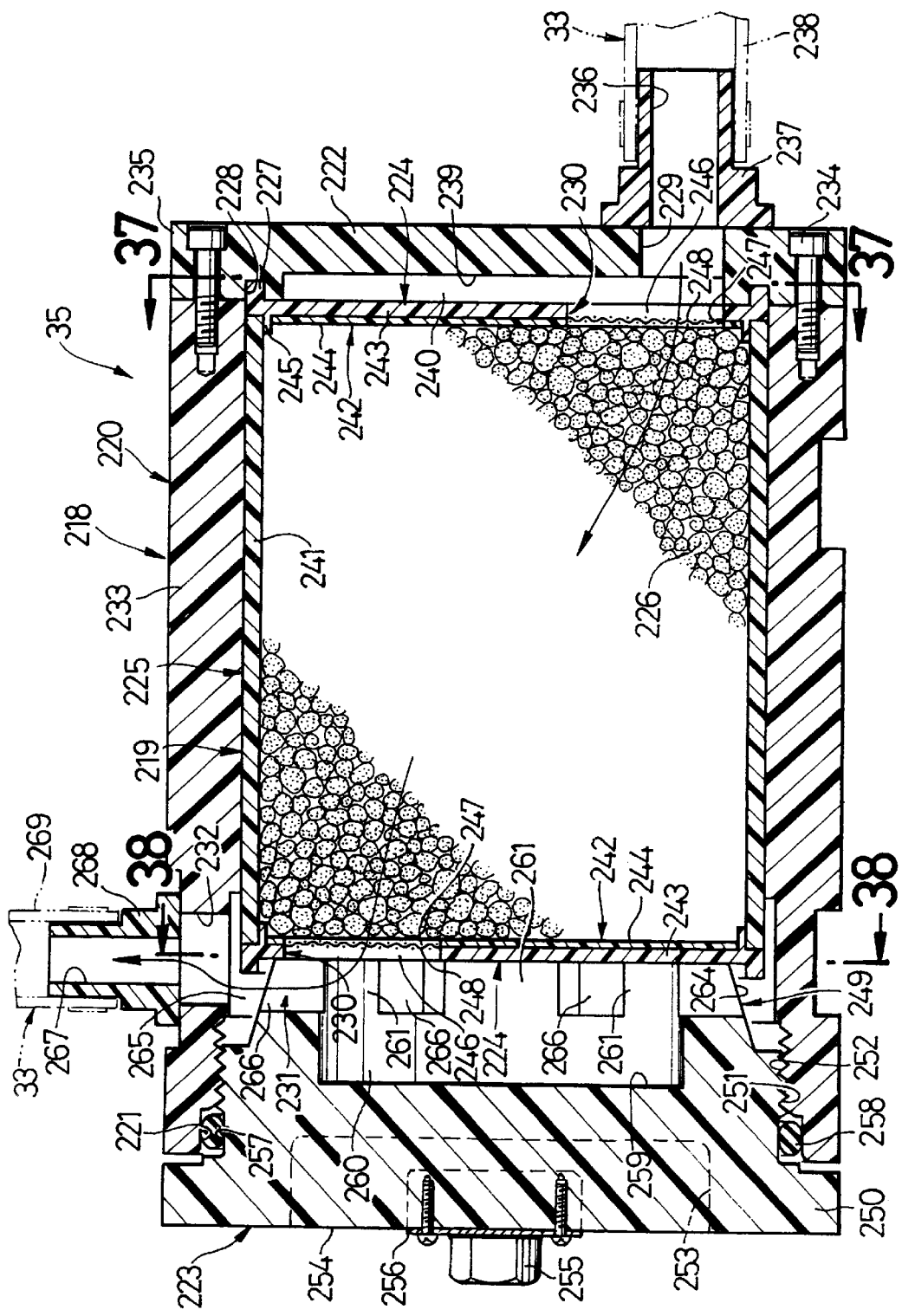
FIG. 36 is a vertical sectional side view of a chlorine gas purifying device, which corresponds to a sectional view taken along a line 36—36 in FIG. 7.

As best shown in FIG. 36, the chlorine gas purifying device 35 is comprised of an outer shell 218 made of a synthetic resin, and a tubular catalyst unit 219 accommodated in the outer shell 218. The outer shell 218 is comprised of a bottomed tubular body 220 into which the catalyst unit 219 is fitted, and a lid 223 capable of being attached to and detached from an opening 221 in the body 220 to close the opening 221 to urge the catalyst unit 219 to a bottom 222 of the body 220. The catalyst unit 219 is comprised of a tubular member 225 made of a synthetic resin and having end walls 224 at opposite ends thereof, and an activated carbon 226 as a catalyst accommodated in the tubular member 225.

One of the end walls 224 and the bottom walls 222 of the bottomed tubular body 220, i.e., an annular projection 227 located on the end wall 224 in the illustrated embodiment, is fitted into the other, i.e., an annular recess 228 provided in the bottom wall 222, so that an inlet 229 for the aqueous solution of NaCl provided in the bottom wall 222 at a location inner than the projection/recess fit portions communicate with a through-hole 230 provided in the end wall 224. The through-hole 230 provided in the other end wall 224 of the catalyst unit 219 communicates with an outlet 232 for the aqueous solution of NaCl in a peripheral wall of the bottomed tubular body 220 through a passage 231 in the lid 223.

In the outer shell 218, the bottomed tubular body 220 is comprised of a cylinder 233 and a circular end plate 235 mounted to one end face of the cylinder 233 by a plurality of bolts 234 to form the bottom wall 222. A liquid sealant is applied to one end face of the cylinder 233 against which the circular end plate 235 abuts. A connector 237 made of a synthetic resin is bonded to an outer surface of the circular end plate 235 and has a through-hole 236 communicating with the inlet 229. A pipe 238 which is a portion of the treating pipe line 33, extends from the outlet 210 of the suction pump 34, as also shown in FIG. 9, and is connected to the connector 237.

The circular end plate 235 has a circular recess 239 provided in its inner surface at a location inner than the annular recess 228, and a space 240 for flowing of the aqueous solution of NaCl is defined by cooperation of the circular recess 239 and the end wall 224 of the catalyst unit 219 and communicates with the inlet 229 and the through-hole 230.

Figure 37:
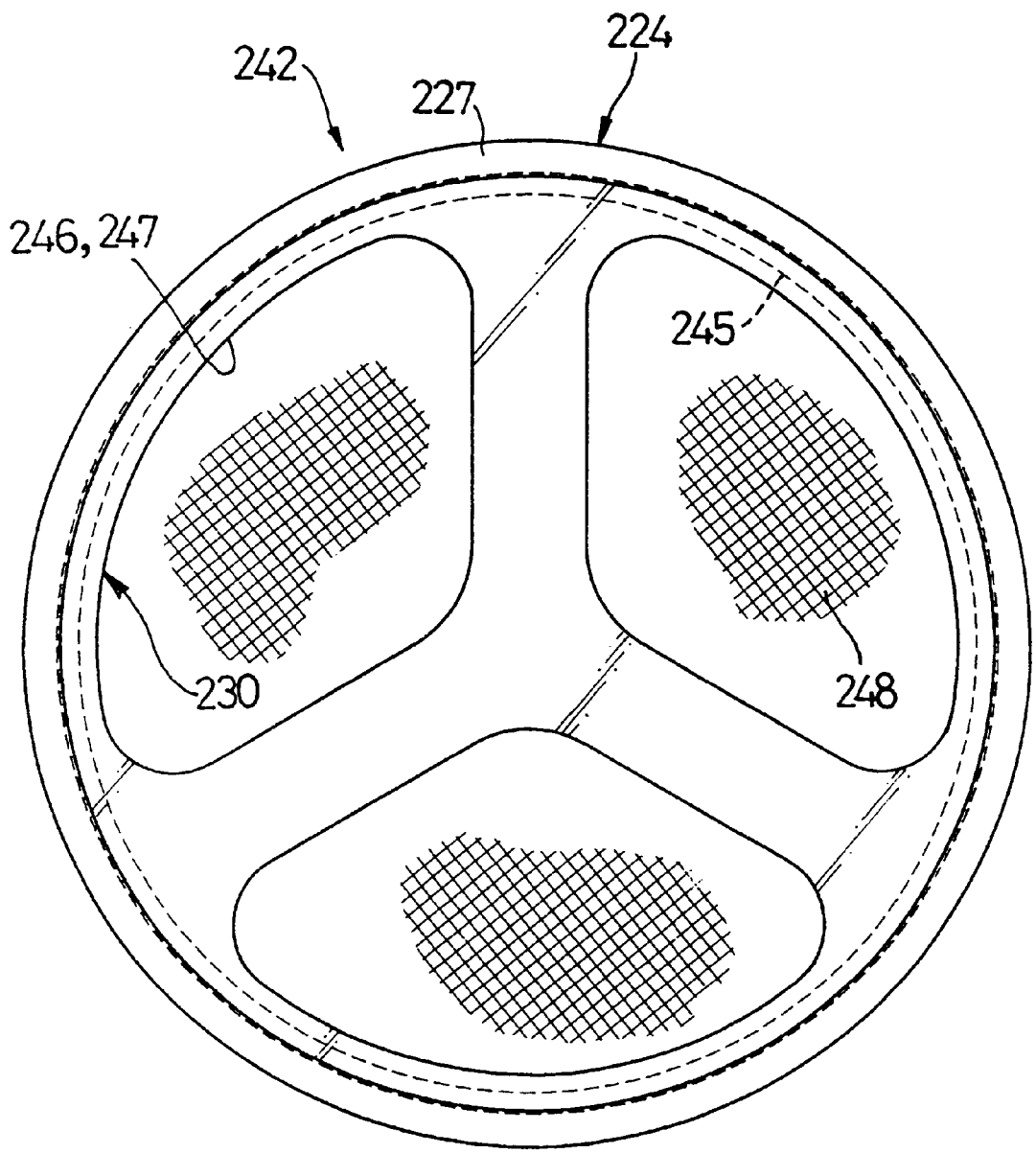
FIG. 37 is a view of a catalyst unit, which corresponds to a view taken along a line 37—37 in FIG. 36.

The tubular member 225 of the catalyst unit 219 is comprised of a cylinder 241 and a pair of circular end plates 242 mounted to openings at opposite ends to form the end walls 224 and having the same structure. The circular end plate 242 includes an outer plate 243 and an inner plate 244. The outer plate 243 has the annular projection 227 on an outer periphery of its outer surface, and also has an annular projection 245 fitted into and bonded in an opening in the cylinder 241 in the vicinity of an outer periphery of its inner surface. Further, the outer plate 243 has a plurality of openings 246, as also shown in FIG. 37, so that they open into an area surrounded by the annular projections 227 and 245. A net-like filter 248 made of a synthetic resin is placed in the entire area surrounded by the inner annular projection 245 of the outer plate 243, and the inner plate 244 having a plurality of openings 247 matched with the openings 246 in the outer plate 243 is fitted into and bonded in such area. A plurality of through-holes 230 are defined by the opposed openings 246 and 247 in the inner and outer plates 244 and 243 for permitting the communication between the flowing space 240 and the inside of the tubular member 225 of the catalyst unit 219. A filter 248 is located in each of the through-holes 230.

Figure 38:
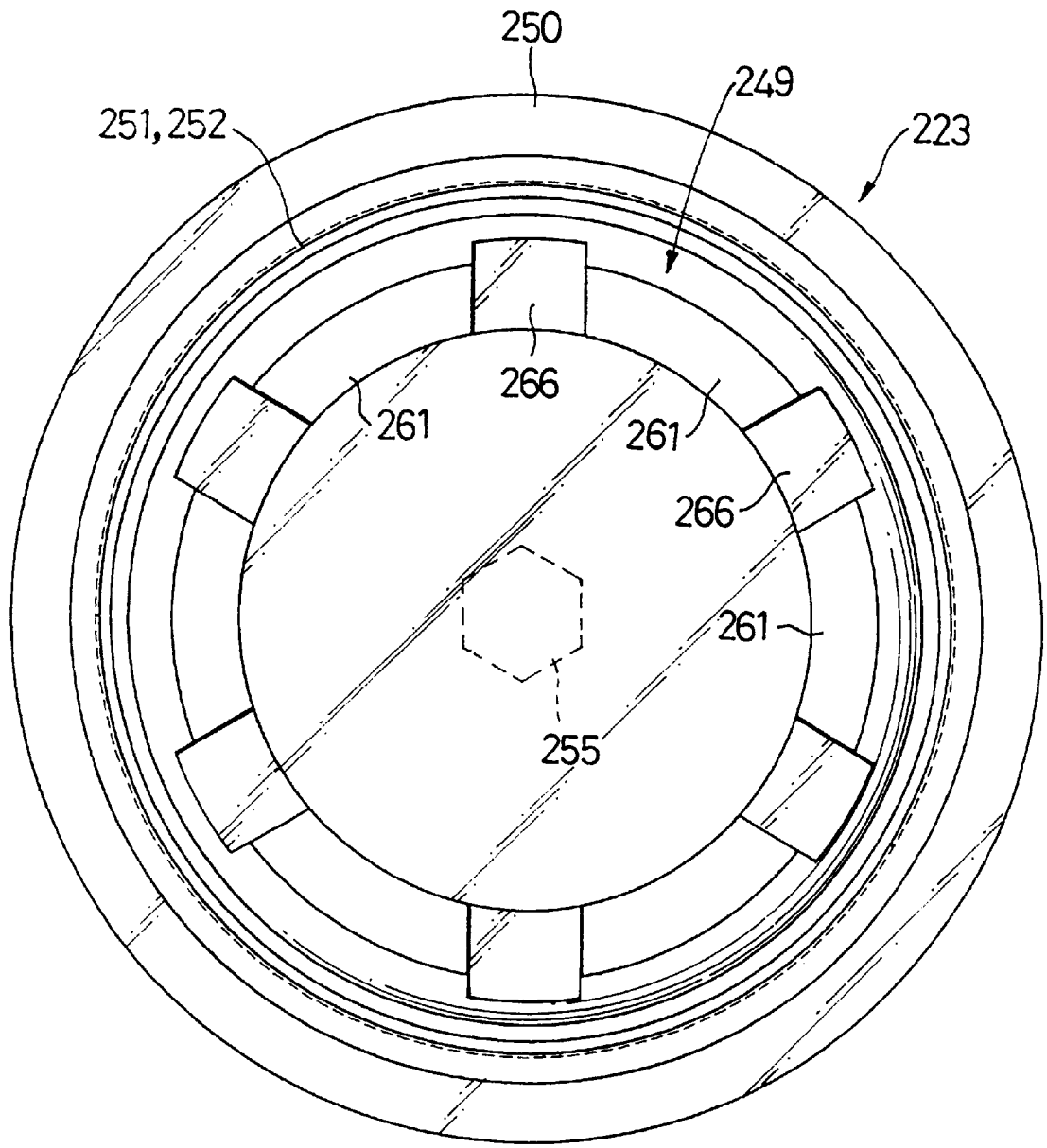
FIG. 38 is a view of a lid, which corresponds to a view taken along a line 38—38 in FIG. 36.

As also shown in FIG. 38, the lid 223 includes a circular tubular portion 249, and a circular flange portion 250 connected to an outer end of the circular tubular portion 249. External threads 251 on an outer peripheral surface of the circular tubular portion 249 are threadedly engaged with internal threads 252 on an inner peripheral surface of the opening 221 in the bottomed tubular body 220. A fitment 256 having a hexagonal head 255 is mounted to a projection 254 between a pair of half moon-shaped recesses 253 located in an outer surface of the circular flange portion 250. In carrying out the above-described threaded engagement, a tool is brought into engagement with the hexagonal head 255. A ring groove 257 is defined in the circular tubular portion 249 on the side of the flange portion 250, and the circular tubular portion 249 and the opening 221 in the bottomed tubular body 220 are sealed therebetween by a seal ring 258 made of a rubber and mounted in the ring groove 257.

The circular tubular portion 249 has a circular recess 259 in its inner surface, and a flowing space 260 for the aqueous solution of NaCl is defined by cooperation of the circular recess 259 and the end walls 224 of the catalyst unit 219 to communicate with the through-holes 230. A plurality of projections 261 are disposed at equal distances around the circular recess 259, so that an end face of each of the projections 261 is urged against the end wall 224 of the catalyst unit 219. That portion of an outer peripheral surface of the circular tubular portion 249, which is inner than the external threads 251, is formed into a tapered surface 264. A flowing space 265 is defined between the tapered surface 264 and an inner peripheral surface of the bottomed tubular body 220 to communicate with the outlet 232. A space 266 is defined between the adjacent projections 261 and permits the communication between the flowing spaces 260 and 265. Therefore, the flowing spaces 260 and 265 and the space 266 form the passage 231.

A connector 268 made of a synthetic resin having a through-hole 267 communicating with the outlet 232 is bonded to the outer peripheral surface of the bottomed tubular body 220, and a pipe member 269 of the treating pipe line 33 is connected to the connector 268, as shown in FIG. 9.

In the outer shell 218, the inlet 229 and the outlet 232 are disposed on opposite sides of an axis of the outer shell 218.

As best shown in FIG. 9, the chlorine gas purifying device 35 is disposed on the machine base 44 through the support 208 in an inclined manner such that the outlet 232 thereof lies at an upper location and the inlet 229 thereof lies at a lower location. In this case, the inclination angle β is set at a value such that when the aqueous solution of NaCl 11 within the bottomed tubular body 220 has been withdrawn from the inlet 229 through the suction pump 34 and the drainage pipe 211 for the purpose of replacing the catalyst unit 219, the liquid level of the remaining aqueous solution of NaCl 11 lies below the opening 221 in the body 220.

If the chlorine gas purifying device 35 is constructed in the above-described manner, the aqueous solution of NaCl 11 including the chlorine gas is reliably introduced into the catalyst unit 219 without entering from the inlet 229 into between the outer peripheral surface of the tubular member 225 of the catalyst unit 219 and the inner peripheral surface of the bottomed tubular body 220 of the outer shell 218, by virtue of a labyrinth structure formed by the recess-projection fit portions 228 and 227 between the outer shell 218 and the catalyst unit 219. Therefore, it is possible to enhance the purification rate of the chlorine gas.

In this case, the catalyst unit 219 is urged against the bottom wall 222 of the outer shell 218 by the lid 223 and hence, the labyrinth structure is reliably formed and maintained. The accomplishment and unaccomplishment of the labyrinth structure are easily judged by the condition of mounting of the lid 223 to the bottomed tubular body 220. For example, the unaccomplishment of the labyrinth structure is confirmed by the fact that the seal ring 258 can be viewed from a gap between the flange portion 250 and the body 220.

Further, the chlorine gas purifying device 35 is disposed in the inclined manner such that the outlet 232 is turned upwards, as described above and therefore, even when the unpurified chlorine gas is present in the device 35, the accumulation of the unpurified chlorine gas can be inhibited to the utmost.

Moreover, since the provision of the outlet 232 is not in the lid 223, the mounting and removal of the lid 223 can be easily performed, and the formation of the lid 223 and the catalyst into the unit ensures that the operation of replacing the catalyst can be performed with a good efficiency. In addition, even if the lid 223 is removed from the bottomed tubular body 220 after withdrawal of water, the dropping of the remaining aqueous solution of NaCl from the opening 221 in the body 220 can be prevented by the inclined disposition of the chlorine gas purifying device 35.

The opposite end walls 224 in the catalyst unit 219 have the same structure and hence, in fitting the catalyst unit 219 into the bottomed tubular body 220 to fit the annular projection 227 into the annular recess 228, the catalyst unit 219 may be fitted into the body 220 from the side of any of the end walls 224, leading to a good workability for mounting the catalyst unit 219.

The labyrinth structure in the chlorine gas purifying device 35 may be omitted in some cases.

(4) Determining Device for Determining Timing of Replacement of Catalyst (FIGS. 4 to 6, 39 and 40)

The purifying capability of the activated carbon 226 used as the catalyst is decreased in accordance with the product of the electric current flowing across the carbon electrode 13 and the time. Therefor, in order to replace the activated carbon 226 by a new activated carbon 226, e.g., the catalyst unit 219 in this embodiment before the purifying capability of the activated carbon in service is completely lost, the determining device 270 is mounted in the electrolytic test machine 1. The determining device 270 is incorporated in the computer programmed control unit 10.

Figure 39:
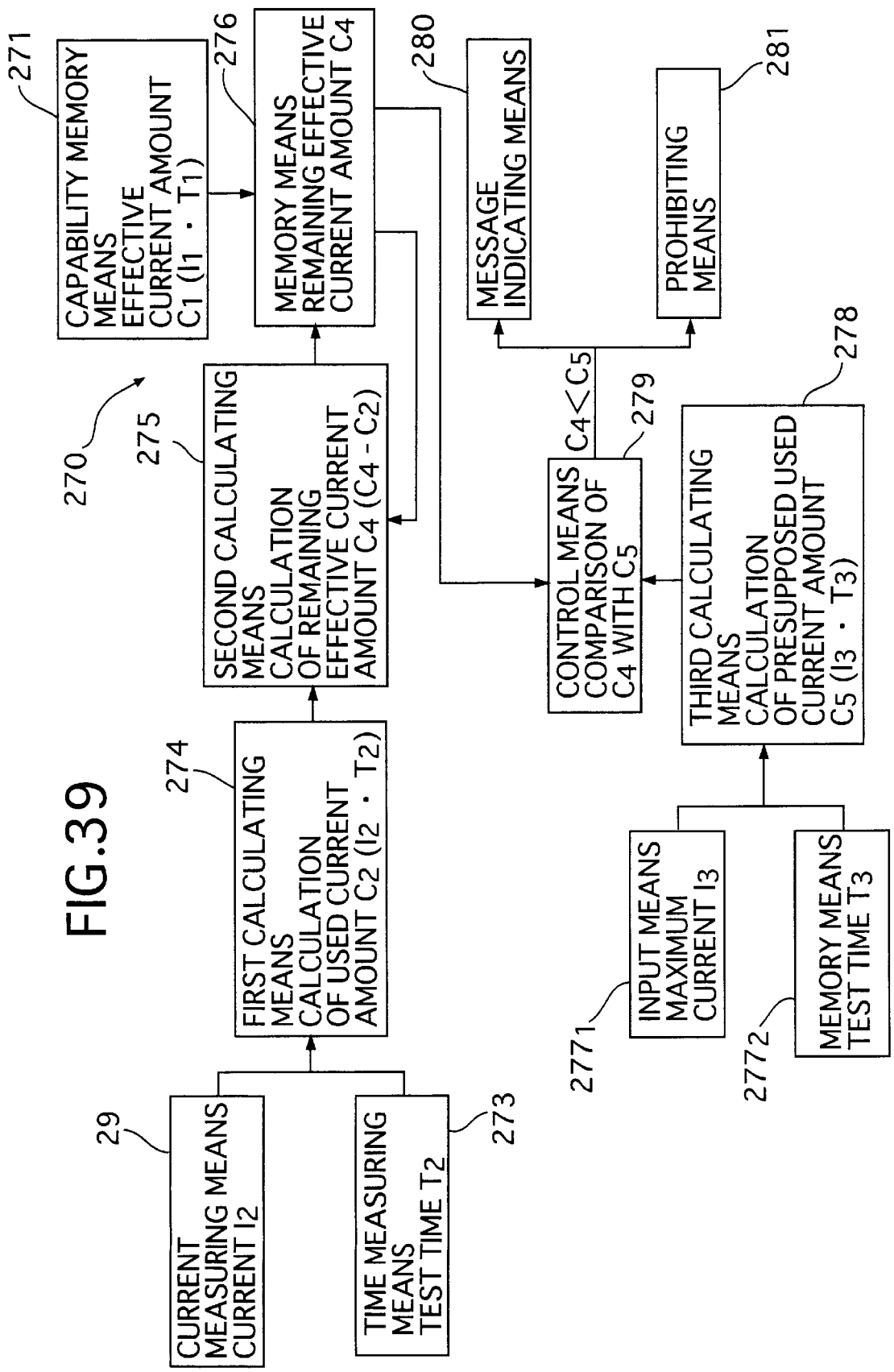
FIG. 39 is a block diagram of a determining device for determining a timing of replacement of a catalyst.
Figure 40:
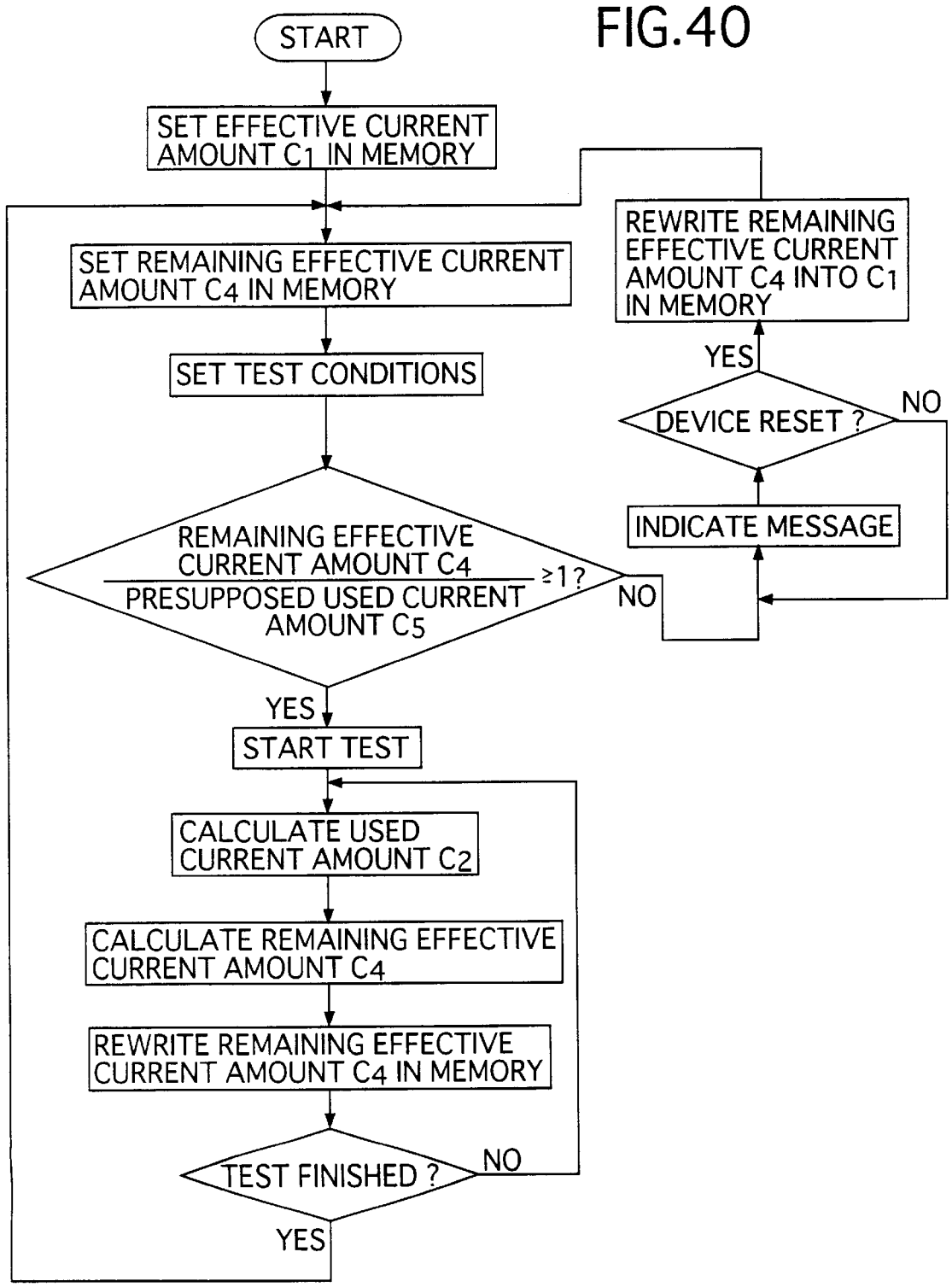
FIG. 40 is a flow chart illustrating the operation of the determining device for determining the timing of replacement of the catalyst.

FIG. 39 is a block diagram of the determining device 270, and FIG. 40 is a flow chart illustrating the operation of the determining device 270. The term "set test conditions" in FIG. 40 means that any is selected of the facts that the corrosion resistance test including the coating film peeling-off step and the steel plate corroding step is to be carried out, that the coating film peeling-off test is to be carried out, and that the test to be finished, and these conditions are inputted.

Referring to FIG. 39, the determining device 270 includes a capability storage means 217 for storing the purifying capability of the activated carbon 226 in terms of an effective current amount $C_1$ which is a product $I_1 \cdot T_1$ of a certain current $I_1$ flowing across the carbon electrode 13 and a total test time $T_1$ usable when the current $I_1$ is continued to flow; a memory means 276 for storing the effective current amount $C_1$ as a remaining effective current amount $C_4$; a current measuring means (ammeter) 29 for measuring a current $I_2$ flowing across the carbon electrode 13 during a test, and a time measuring means 273 for measuring a test time $T_2$; a first calculating means 274 for calculating a used current amount $C_2$ which is a product $I_2 \cdot T_2$ of the current $I_2$ and the test time $T_2$; a second calculating means 275 for subtracting the used current amount $C_2$ from the remaining effective current amount $C_4$ to calculate a new remaining effective current amount and to store the latter in the memory means 276; an input means $277_1$ for inputting a maximum current $I_3$ of the DC power source 9 at the start of the test, and a memory means $277_2$ for storing a test time $T_3$; a third calculating means 278 for calculating a presupposed used current amount $C_5$ which is a product $I_3 \cdot T_3$ of the maximum current $I_3$ and the test time $T_3$; and a control means 279 adapted to compare the remaining effective current amount $C_4$ and the presupposed used current amount $C_5$ with each other and to transmit a catalyst replacing signal, when $C_4<C_5$.

If the determining device 270 is constructed in the above manner, it is possible, before the carrying-out of the test, to automatically detect the fact that the timing of replacement of the activated carbon 226 has been reached due to the decrease in purifying capability of the activated carbon 226.

The determining device 270 also includes a message indicating means 280 adapted to inform a testing personnel of the reaching of the catalyst replacing timing based on the catalyst replacing signal from the control means 279, and a prohibiting means 281 for prohibiting the supplying of current to the carbon electrodes 13.

As best shown in FIGS. 4 to 6, a message indicated by the message indicating means 280 is displayed by characters on a liquid crystal display plate 131 mounted on the upper surface of the left cover section 52 covering the control section C. The prohibiting means 281 is operated to maintain the DC power source 9 in its OFF state. Thus, the testing personnel can reliably know the timing of replacement of the activated carbon 226.

As shown in FIG. 40, the determining device 270 is constructed so that the device 270 is not operated unless the device 270 is reset after replacement of the catalyst unit 219 to bring the remaining effective current amount $C_4$ in the memory means 276 into a relation of $C_4=C_1$.

If the remaining effective current amount $C_4$ and the presupposed used current amount $C_5$ are in a relation of $C_4 \geq C_5$ in starting the test, the test is started, and the calculation of the used current amount $C_2$ and the like are carried out.

[N] Exhaust Device (1) Entire Structure and Function thereof (FIGS. 7 to 9 and 41 to 44)

As described above, a chlorine gas is generated around the carbon electrodes 13 in the corrosion resistance test. Most of the chlorine gas is collected and purified by the chlorine gas treating device 6 described in the item [M], and a portion of the chlorine gas is floated up out of the aqueous solution of NaCl 11 to flow above the liquid level f. The exhaust device 7 is mounted in the electrolytic test machine 1 to collect the flowing chlorine gas.

Figure 41:
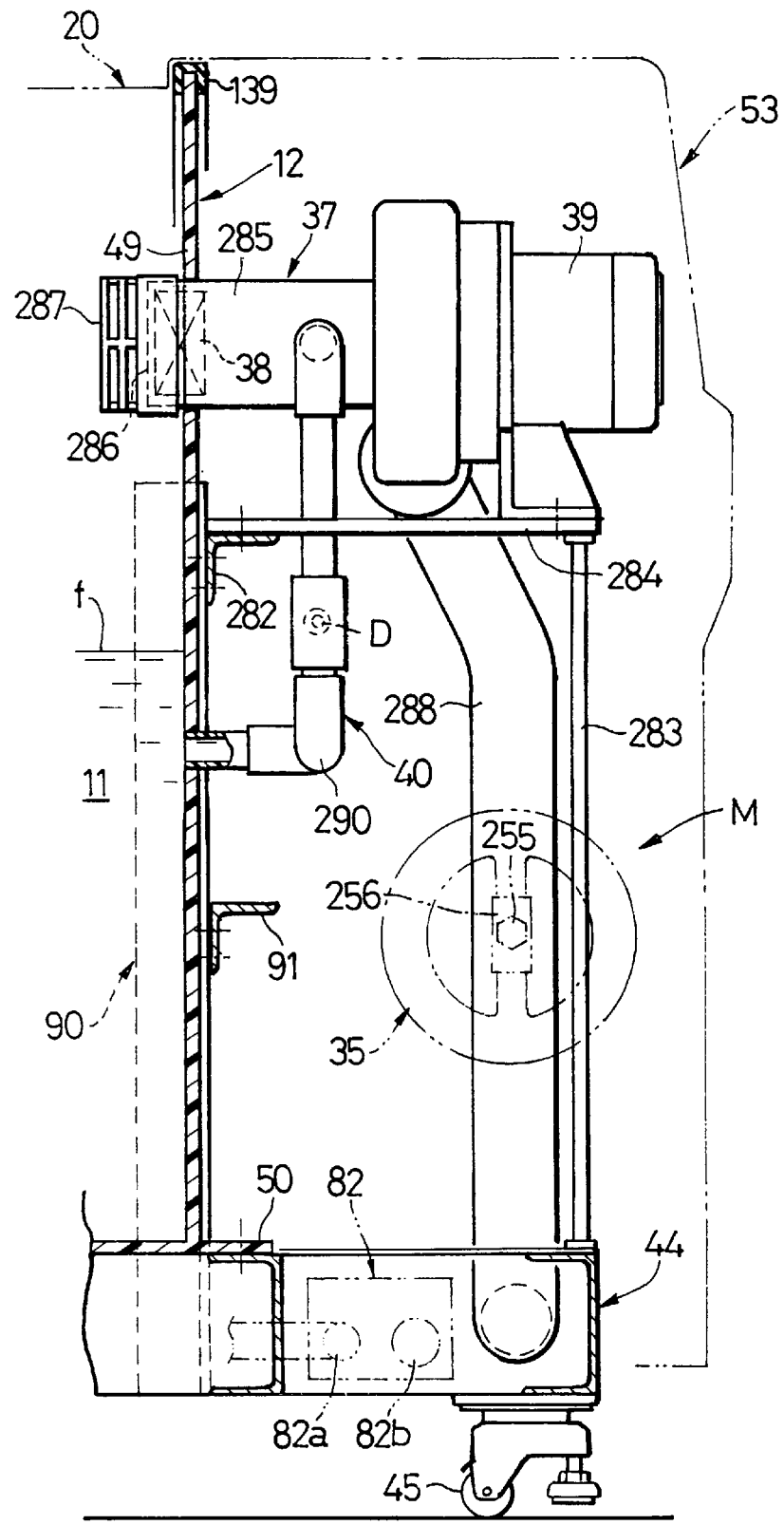
FIG. 41 is a sectional view taken along a line 41—41 in FIG. 9.

As best shown in FIGS. 9 and 41, the exhaust fan 39 of the exhaust device 7 is fixed on a mounting base 284 which is supported by an upper angle member 282 of the frame 90 and a support pillar 283. An intake pipe 285 extending from the inlet of the exhaust fan 39 in the exhaust pipe line 37 is passed through the right sidewall portion 49 of the electrolytic cell 12 to communicate with the inside of the electrolytic cell 12 above the liquid level f of the aqueous solution of NaCl 11. A cap-like grille 287 made of a synthetic resin is detachably mounted to an inlet 286 of the intake pipe 285. A discharge pipe 288 extending from the outlet of the exhaust fan 39 in the exhaust pipe line 37 extends downwards and is opened into the atmosphere in the vicinity of the water dispensing block 82.

On the suction side of the exhaust fan 39 in the exhaust pipe line 37, namely, in the intake pipe 285, the adsorbing member 38 for adsorbing chlorine gas is disposed at an upstream location, and the detecting means 40 for detecting an abnormality of the exhaust system is disposed at a downstream location. The adsorbing member 38 has a structure similar to that of the catalyst unit 219 and hence, includes an activated carbon and has a permeability, and is formed into a unit. Therefore, the grille 287 is removed from the inlet 286 of the intake pipe 285, and the adsorbing member 38 is placed into the intake pipe 285 through the inlet 286.

Figure 42:
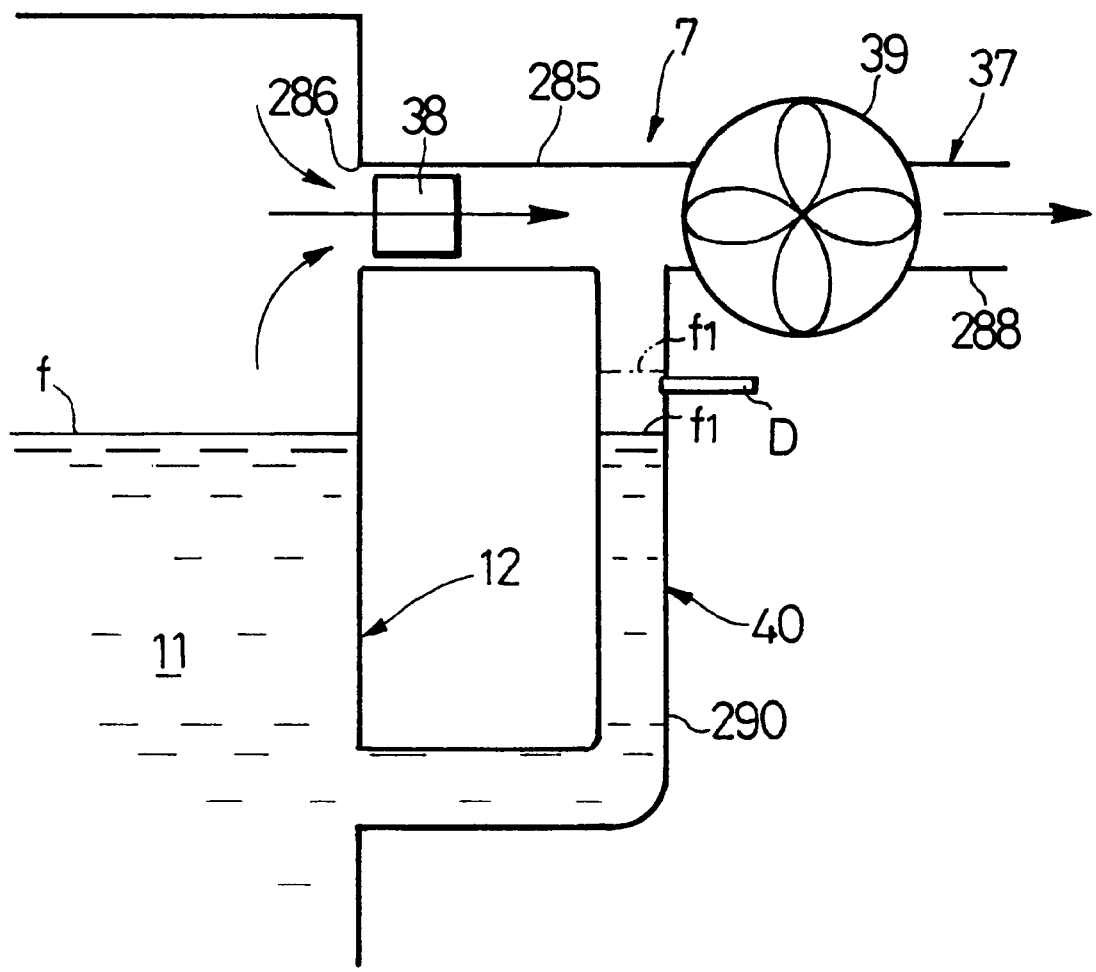
FIG. 42 is a diagram showing one example of an abnormality-generation detecting means in an exhaust system.

The detecting means 40 includes a detecting pipe 290 made of a synthetic resin and mounted between the intake pipe 285 and the electrolytic cell 12, and a water level sensor D mounted in the detecting pipe 290, as best shown in FIGS. 41 and 42. The detecting pipe 290 communicates at its upper end with a downstream portion of the intake pipe 285, and at its lower end with a zone of the electrolytic cell 12 in which the aqueous solution of NaCl 11 is stored. A sensor portion of the water level sensor D is disposed above a liquid level $f_1$ in the detecting pipe 290, which is the same level as the liquid level f in the electrolytic cell 12.

In the above-described construction, if the exhaust fan 39 is operated, the chlorine gas flowing above the liquid level f in the electrolytic cell 12 is adsorbed in the activated carbon when being passed through the adsorbing member 289, and thus, clean air is discharged to the atmosphere through the exhaust pipe 288.

Figure 43:
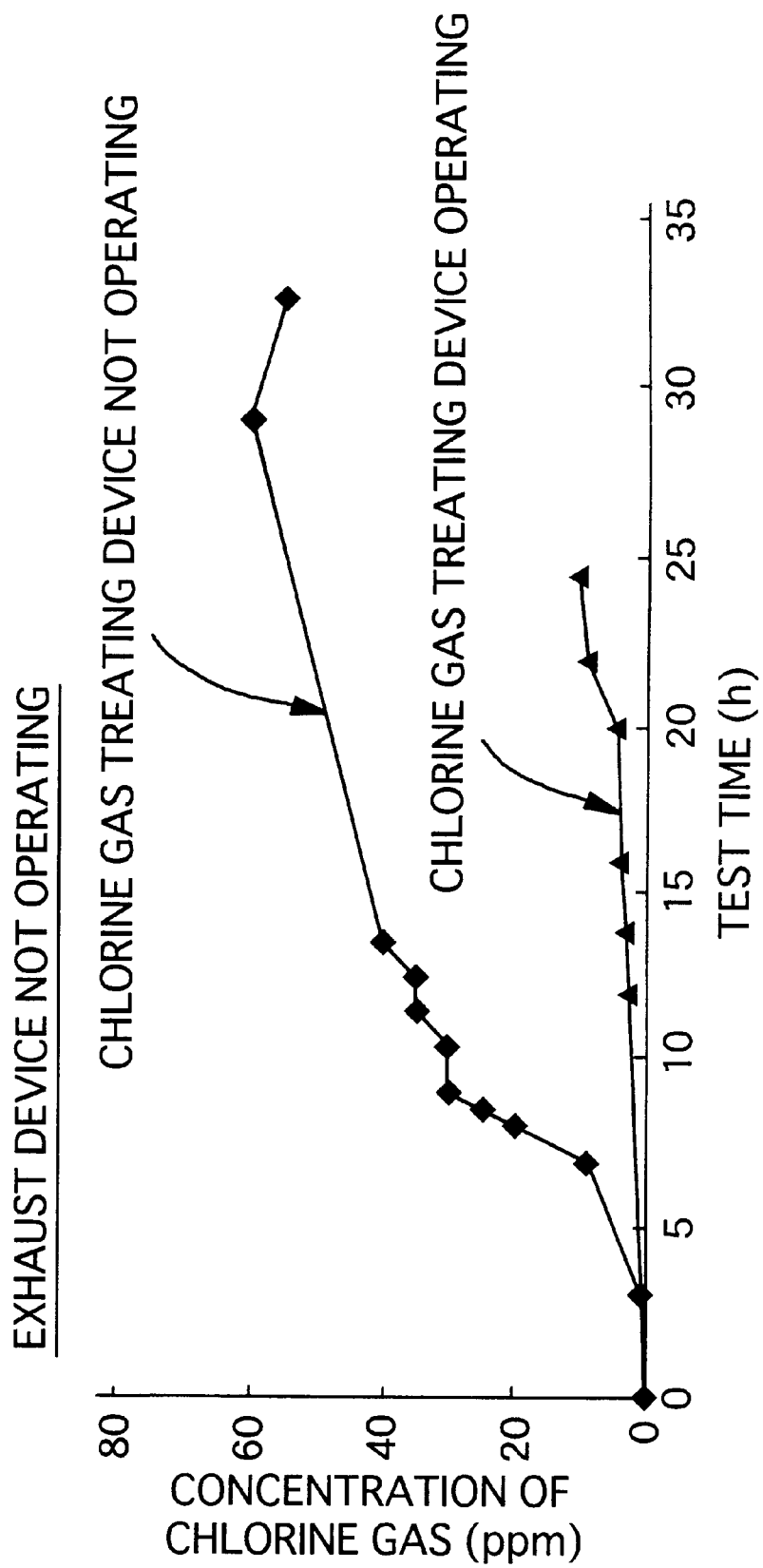
FIG. 43 is a graph illustrating one example of the relationship between the test time and the concentration of the chlorine gas.

FIG. 43 illustrates the relationship between the test time and the concentration of chlorine gas above the liquid level f within the electrolytic cell 12, when the exhaust device 7 was not operated and the chlorine gas treating device 6 described in the item [M] was operated, and when the device 6 was brought into a non-operated state. Test conditions were such that an electric current of 50 A was continuously supplied, and the temperature of the aqueous solution of NaCl 11 was 45° C. As apparent from FIG. 43, if the chlorine gas treating device 6 is operated under the non-operation of the exhaust device 7, the concentration of the chlorine gas can be maintained at an extremely low level, but if the exhaust device 7 is operated, the concentration of the chlorine gas can be further lowered.

Thereupon, to confirm an effect when the exhaust device 7 was used and the activated carbon was used as the adsorbent of the adsorbing member 38, the outlet of the exhaust pipe 288 was put into communication with the inside of the electrolytic cell 12 above the liquid level f in the electrolytic cell 12, and a test which involves circulating the inside gas above the liquid level f through the adsorbent was carried out.

Figure 44:
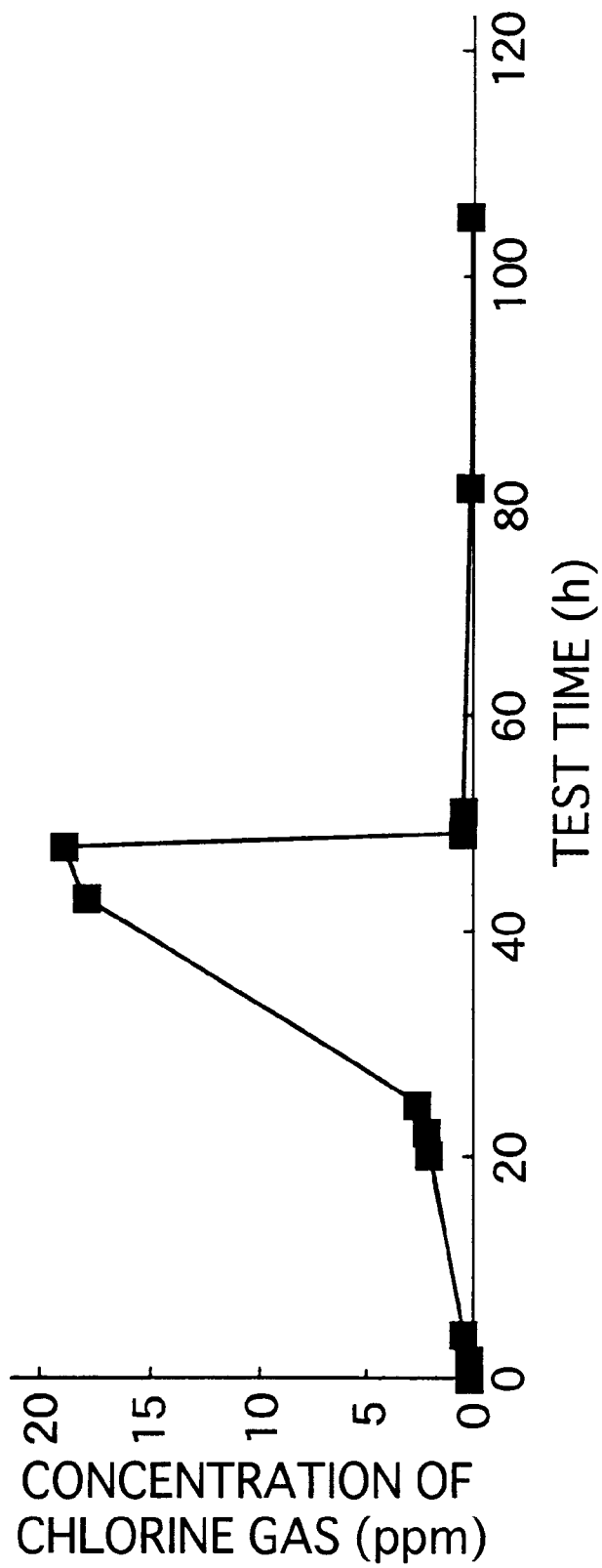
FIG. 44 is a graph illustrating another example of the relationship between the test time and the concentration of the chlorine gas.
Figure 46:
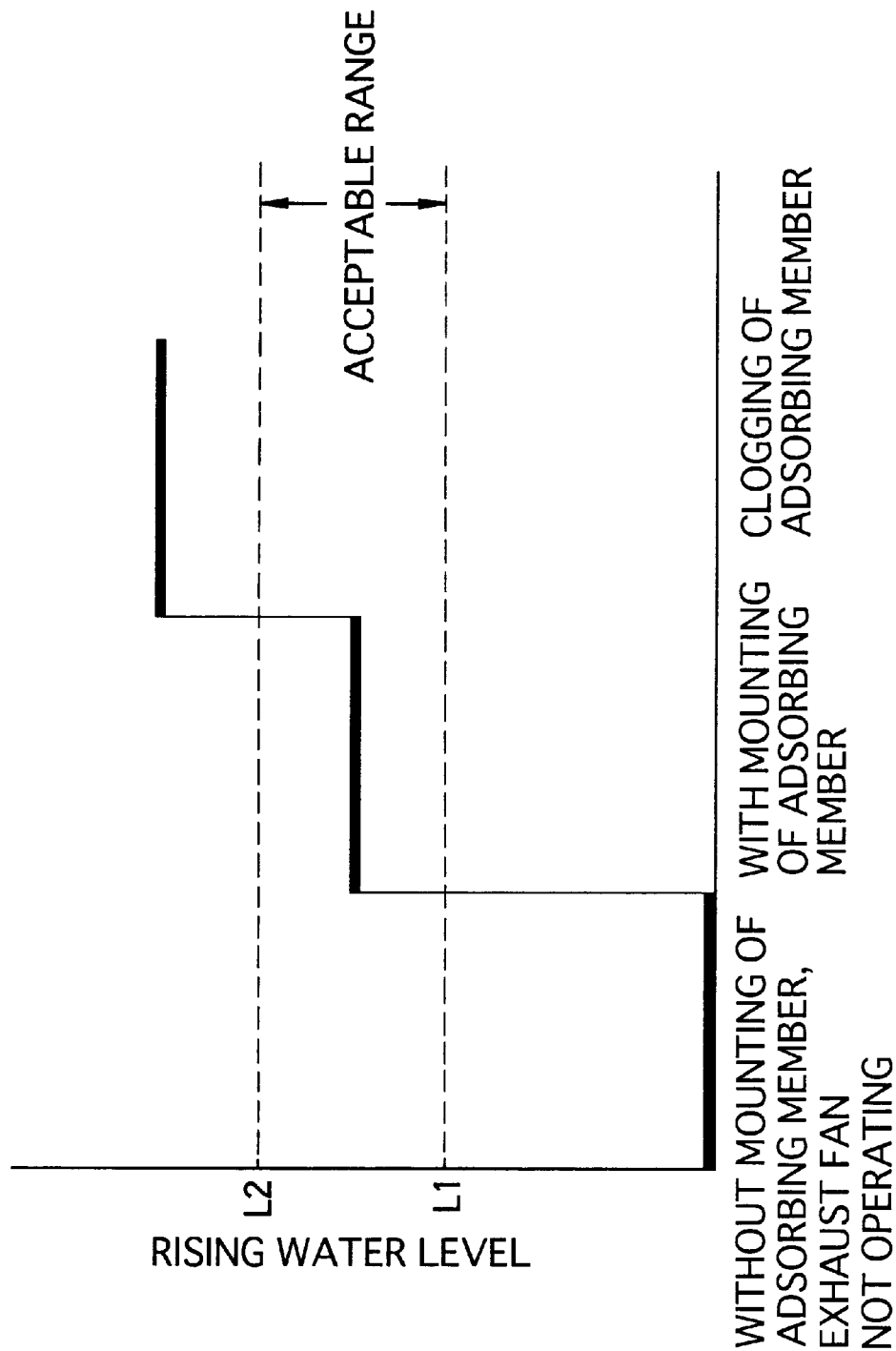
FIG. 46 is a graph illustrating the relationship between the situation of the exhaust system and the risen water level.

FIG. 44 illustrates the relationship between the test time and the concentration of the chlorine gas above the liquid level f within the electrolytic cell 12. Conditions for the test were such that an electric current of 20 A was continuously supplied, and the temperature of the aqueous solution of NaCl 11 was 45° C. In this case, the exhaust fan 39 was not operated for a period from the start of the test until the test time reached 50 hours and hence, the concentration of the chlorine gas was relatively steeply risen and reached about 18 ppm at a time point after lapse of 50 hours. If the exhaust fan 39 was operated thereafter, the concentration of chlorine gas was decreased extremely by the purifying effect of the adsorbent to reach 0.5 ppm or less. Thus, it is obvious that under the use of the exhaust device 7 with one end of the exhaust pipe 288 being opened to the atmosphere, the concentration of the chlorine gas above the liquid level f within the electrolytic cell 12 and the concentration of the chlorine gas discharged to the atmosphere are further decreased and suppressed at least to 0.5 ppm or less.

In the above-described construction, for example, if the adsorbing member 289 is normal, a corresponding negative pressure is generated in the downstream portion, and the liquid level $f_1$ within the detection pipe 290 is risen up to a level equal to or higher than the position of the water level sensor D by such negative pressure, as shown by a dashed line in FIG. 42. Thus, the water level sensor D detects that the exhaust system is normal. On the other hand, if a new adsorbing member 38 is not disposed within the intake pipe 285 due to the forgetting of mounting thereof during replacement of the adsorbing member 289, the negative pressure is considerably lowered more than that in the above-described case. Therefore, the liquid level $f_1$ is below the water level sensor D, and this state is detected by the water level sensor D.

According to such construction, an abnormality of the exhaust system can be easily and reliably detected.

(2) Abnormal-point Detector for Exhaust System (FIGS. 4 to 6, 45 to 47)

As shown in FIGS. 45(a) and 45(b), the detecting means 40 includes a function to transmit an abnormality signal varied depending upon the type of the abnormality of the exhaust system by the fact that the first and second water level sensors $D_1$ and $D_2$ are disposed at locations indicating the lower limit value LI and the upper limit value L2 of the risen water level L in the detection pipe 290, respectively. A control means 291 is connected to the first and second water level sensors $D_1$ and $D_2$ in the detecting means 40 and adapted to discriminate the type of the abnormality based on the abnormality signals from the first and second water level sensors $D_1$ and $D_2$ and to transmit an output signal corresponding to the type of the abnormality. An indicating means 292 is connected to the control means 291 for indicating the type of the abnormality in accordance with the output signal from the control means 291. A prohibiting means 294 is also connected to the control means 291 for prohibiting the supplying of electric current to the carbon electrodes 13 by the output signal from the control means 291.

These means 291 to 294 are incorporated in the computer programmed control unit 10 to constitute an abnormal-point detector 295 for the exhaust system together with the first and second water level sensors $D_1$ and $D_2$. The indicating means 292 indicates, for example, a message, which is displayed by characters on a liquid crystal display plate 131 mounted on the upper surface of the left cover section 52 covering the control section C, as best shown in FIGS. 4 to 6. The prohibiting means 294 is operated to maintain the DC power source 9 in its OFF state.

Figure 47:
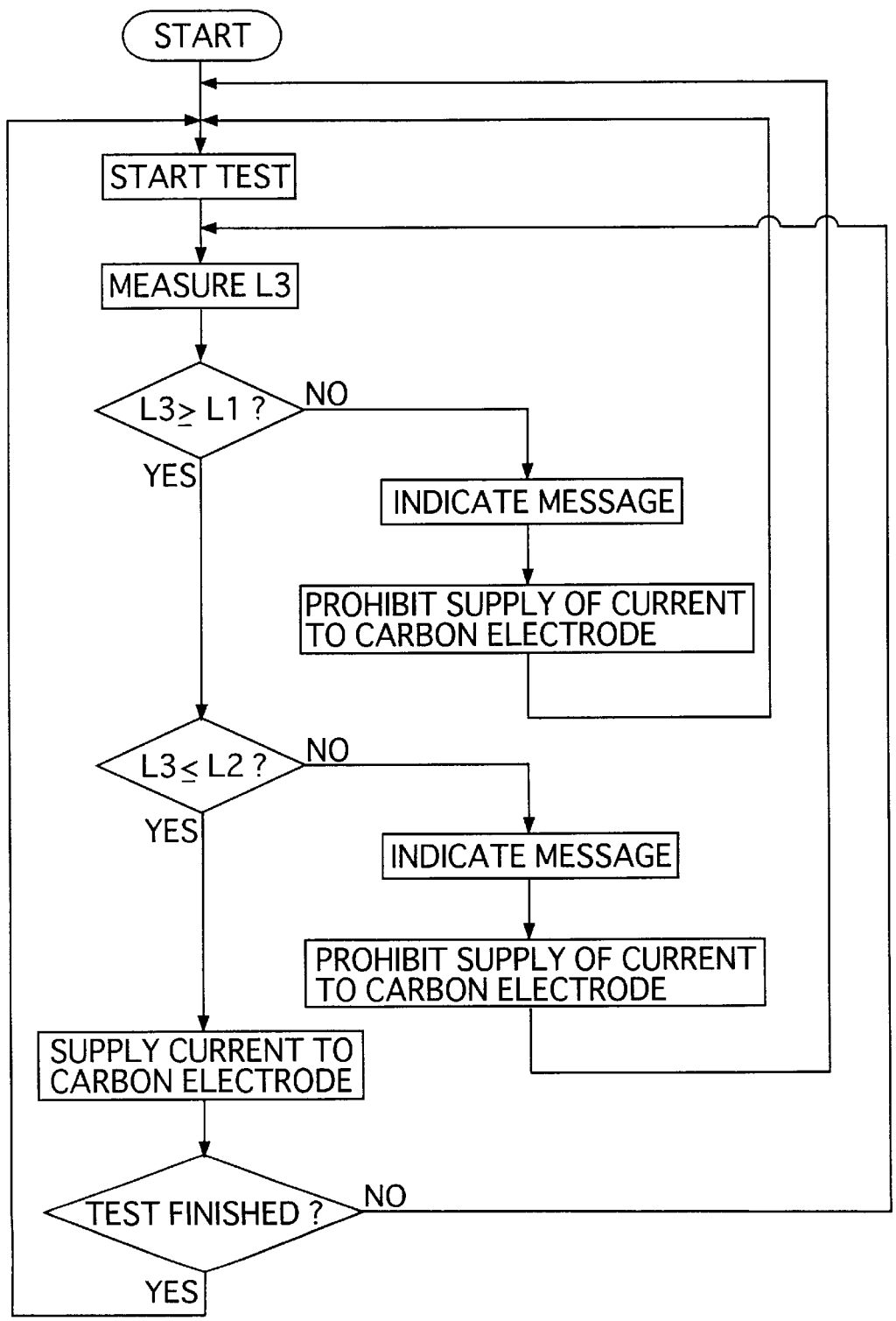
FIG. 47 is a flow chart illustrating the operation of the abnormal-point detector.

As shown in FIGS. 45 and 47, if a signal indicative of a command to start the test is inputted, the first and second water level sensors $D_1$ and $D_2$ detect water levels depending upon the negative pressure in the intake pipe 285. If the detected water level L3 is in an acceptable range of L1≦L3<L2, the first water level sensor $D_1$ is in its ON state, and the control means 291 determines that the first water level sensor $D_1$ is transmitting the normality signal. Therefore, an electric current is supplied to the carbon electrodes 13 to start the corrosion resistance test.

If the detected water level L3 is lower than L1, the first water level sensor $D_1$ is in its OFF state, and the control means 291 determines that the first water level sensor $D_1$ is not transmitting the normality signal, namely, is transmitting the abnormality signal, which corresponds to the non-mounting of the adsorbing member 38 and the non-operation of the exhaust fan 39, whereby the control means 291 transmits a corresponding output signal. Thus, a message "stop the test because of the non-mounting of the adsorbing member 38 or the non-operation of the exhaust fan 39" is indicated by the indicating means 292, and the supplying of current to the carbon electrodes 13 is prohibited by the prohibiting means 294.

If the detected water level L3 is equal to or higher L2, the second water level sensor $D_2$ is in its ON state, and the control means 291 determines that the second water level sensor $D_2$ is transmitting the abnormality signal, which corresponds to the clogging of the adsorbing member 38, whereby the control means 291 transmits a corresponding output signal. Thus, a message "stop the test because of the clogging of the adsorbing member 38" is indicated by the indicating means 292, and the supplying of current to the carbon electrodes 13 is prohibited by the prohibiting means 294.

The abnormal-point detector 295 for the exhaust system is controlled so that it is operated even during the corrosion resistance test.

The detector 295 enables a trouble point of the exhaust system to be easily and reliably detected to properly inform a testing personnel of it. In addition, the detector 295 is of a simple construction and hence, is relatively inexpensive.

Only the indicating means 292 may be connected to the control means 291. In addition, in place of the water level sensors $D_1$ and $D_2$, a diaphragm-type negative pressure sensor, an air flow sensor, a wind speed sensor or the like may be used.

Figure 48:
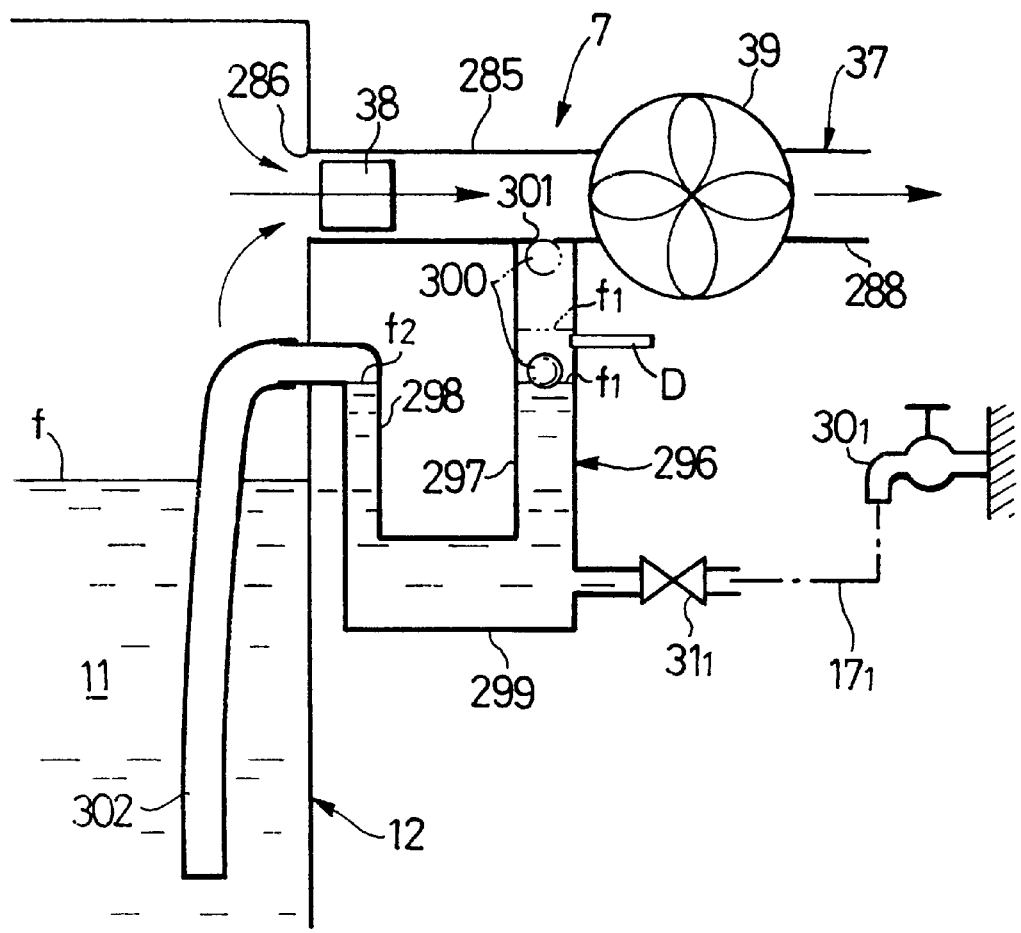
FIG. 48 is a diagram showing another example of an abnormality-generation detecting means in the exhaust system.

(3) Modification to Exhaust Device (FIG. 48)

The detection pipe 296 made of the synthetic resin is comprised of first and second pipe portions 297 and 298 extending vertically, and a third pipe portion 299 which connects lower ends of the first and second pipe portions 297 and 298 to each other. An upper end of the first pipe portion 297 communicates with the downstream portion of the intake pipe 285, and an upper folded end of the second pipe portion 298 communicates with space above the liquid level $f_1$ in the electrolytic cell 12 at a location lower than the upper end of the first pipe portion 297. A water supply pipe line $17_1$ made of a synthetic resin pipe material is connected to the third pipe portion 299 and also connected to the a cock $30_1$ in a water service.

A water level sensor D similar to those described above is mounted in the first pipe portion 297 to lie above the liquid level $f_1$, and a float valve 300 is accommodated in the first pipe portion 297. A valve seat 301 of the float valve 300 is formed at a communication portion of the first pipe portion 297 with the intake pipe 285.

A tube 302 made of a soft synthetic resin is connected to the upper end of the second pipe portion 298, and depends into the electrolytic cell 12. The tube 302 is used for supplying water to the electrolytic cell 12 and for washing the electrolytic cell 12.

A solenoid valve $31_1$ similar to the solenoid valve 31 described in the item [D] is mounted at an intermediate portion of the water supply pipe line $17_1$. The water supply pipe line 17 in the above-described example is eliminated by mounting of such water supply pipe line $17_1$.

The supplying of water to the electrolytic cell 12 is performed from the water supply pipe line $17_1$ through the detection pipe 296, and the liquid level $f_1$ in the first pipe portion 297 is defined at the same position as a liquid level $f_2$ at the upper folded portion of the second pipe portion 298 by overflowing of water from the upper folded end of the second pipe portion 298 into the electrolytic cell 12.

During supplying of water to the electrolytic cell 12, if water is substantially filled up in the first pipe portion 297 due to the force of water, the clogging of the tube 302 or the like, the float valve 300 is seated onto the valve seat 301 to prevent the overflow of water toward the exhaust fan 39. The same is true when the inside of the electrolytic cell 12 is washed through the tube 302.

A sensor portion of the water level sensor D is immersed in tap water with rising of the liquid level $f_1$ and hence, the sensor portion can be kept clean. The chlorine gas flowing above the liquid level f in the electrolytic cell 12 is prevented from being leaked to the outside by a trap effect of the detecting pipe 296.

[O] Overflow Device having Adsorbing Function (FIGS. 7, 8, 13, 14 and 49)

This device 8 is mounted in the electrolytic test machine 1 in order to discharge an extra amount of the aqueous solution of NaCl, when the amount of the aqueous solution of NaCl 11 exceeds a defined value due to a trouble of the water level sensor 15 placed in the electrolytic cell 12 on the intake side corresponding to the exhaust device 7.

Figure 49:
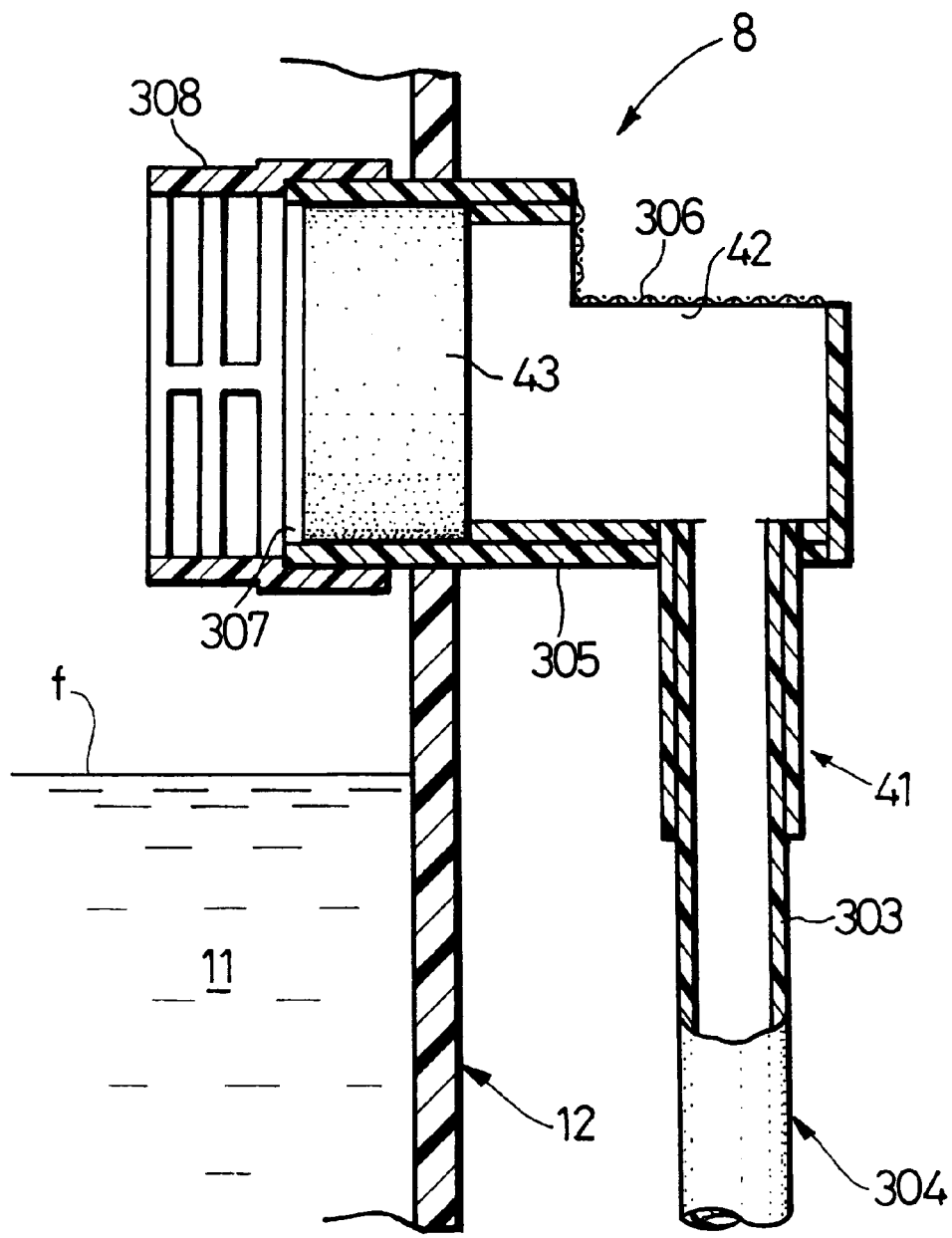
FIG. 49 is a sectional view taken along a line 49—49 in FIG. 7.

As best shown in FIGS. 8, 13 and 49, the overflow pipe 41 is comprised of a folded pipe section 304 having a vertical portion 303 extending along the outer surface of the rear wall portion 71 of the electrolytic cell 12, and a horizontal inlet-side pipe section 305 which is connected to an upper end of the vertical portion 303 and which has a diameter larger than that of the vertical portion 303. The inlet-side pipe section 305 is passed through the rear wall portion 71 of the electrolytic cell 12 to communicate with the space above the liquid level f. As shown in FIGS. 8 and 14, the folded pipe portion 304 is connected at its lower end to the drainage portion 82b of the water dispensing block 82.

In a portion of the inlet-side pipe section 305 protruding from the electrolytic cell 12, substantial upper half thereof from an outer end to an intermediate portion is notched, so that the inlet-side pipe section 305 is also used as an intake pipe. Thus, the gas intake port 42 is defined in the inlet-side pipe section 305. A net 306 for removing a foreign matter is mounted on a peripheral portion of the gas intake port 42 to cover the gas intake port 42.

The adsorbing member 43 for adsorbing the chlorine gas is disposed in the inlet pipe section 305 at a place nearer to an inlet 307 than the gas intake port 42. The adsorbing member 43 has a structure similar to that of the catalyst unit 219 and hence, includes an activated carbon and has an air/water permeability and is formed as a unit. Therefore, a cap-like grille 308 made of a synthetic resin attachable to and detachable from the inlet 307 of the inlet pipe section 305 is removed from the inlet 307 of the inlet-side pipe section 305, and the adsorbing member 43 is placed into the inlet pipe section 305 through the inlet 307.

In the above-described construction, if the amount of the aqueous solution of NaCl 11 within the electrolytic cell 12 exceeds the defined value, the extra amount of the aqueous solution is discharged from the inlet 307 through the adsorbing member 43 and the overflow pipe 41 to the water dispensing block 82. In this case, the aqueous solution of NaCl 11 flows in the lower portion of the inlet-side pipe section 305 and hence, the overflowing of the solution from the gas intake port 42 is not produced.

The suction of the gas into the electrolytic cell 12 produced by the operation of the exhaust device 7 is performed through the gas intake port 42 and the inlet-side pipe section 305. The leakage of the chlorine gas flowing above the liquid level f under the non-operation of the exhaust device 7 out of the electrolytic cell 12 is inhibited by the adsorbing member 43.

[P] Other Example of Determining Device for Determining Timing of Replacement of Carbon Electrode (FIG. 4 to 6, 50 and 51)

Figure 50:
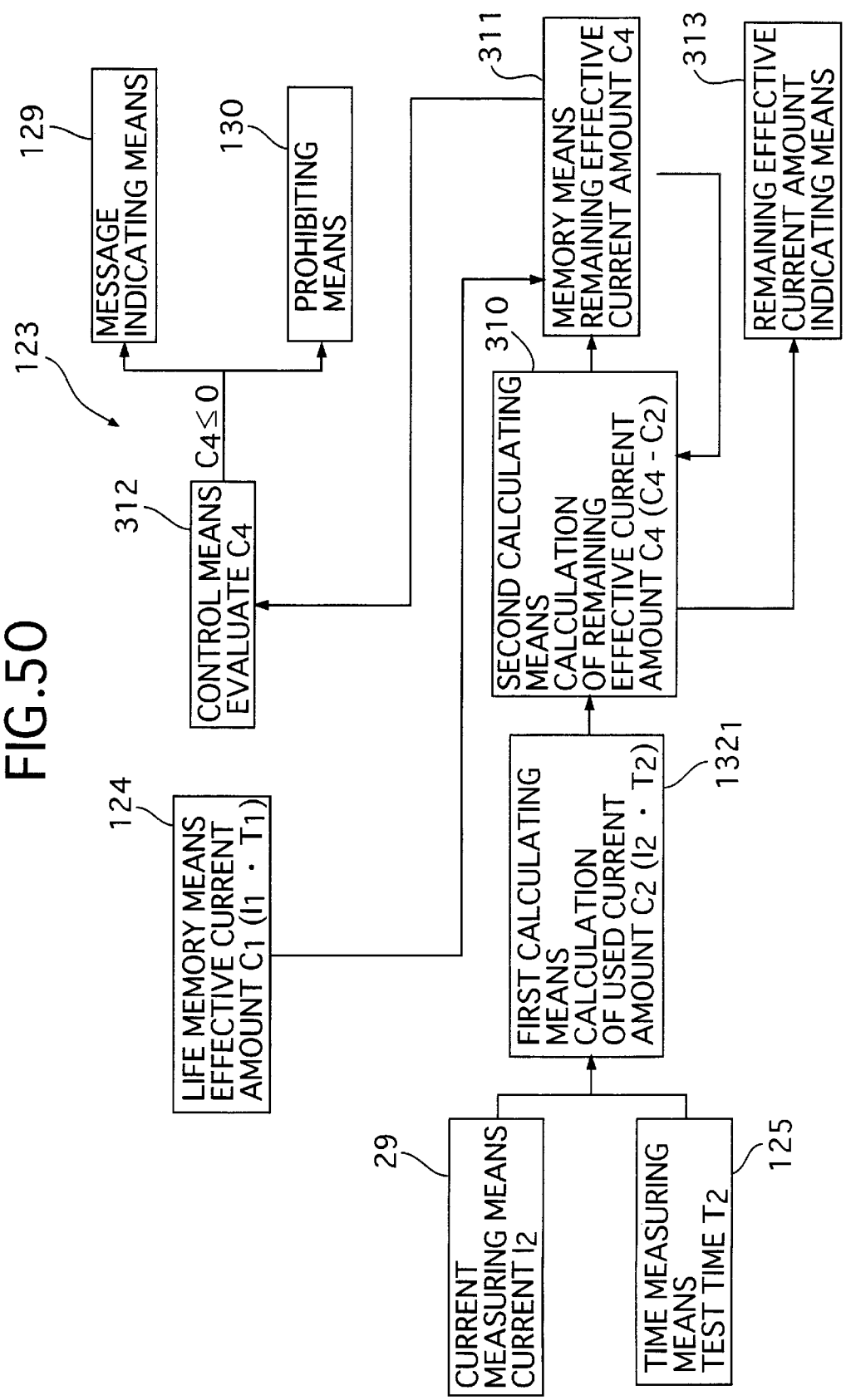
FIG. 50 is a block diagram showing another example of a determining device for determining a timing of replacement of the carbon electrode.
Figure 51:
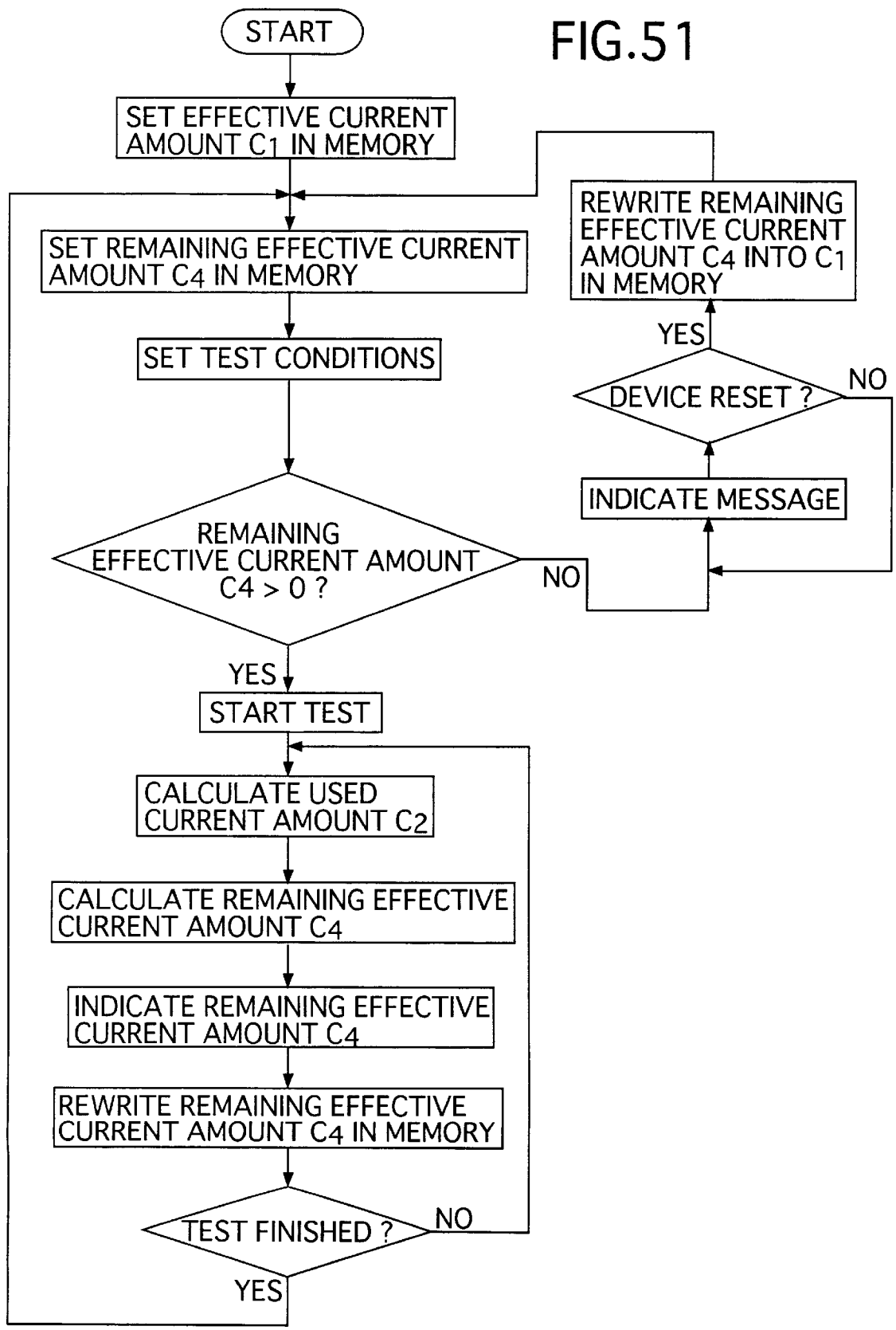
FIG. 51 is a flow chart illustrating the operation of the other example of the determining device for determining the timing of replacement of the carbon electrode.

FIG. 50 is a block diagram of the determining device 123 and FIG. 51 is a flow chart illustrating the operation of the determining device 123. The term "set test conditions" in FIG. 51 means that any of the fact that the corrosion resistance test including the coating film peeling-off step and the steel plate corroding step is to be carried out, the fact that the coating film peeling-off test is to be carried out, and the fact that the test is to be finished, is selected, and conditions therefor are inputted, as in the item [I].

Referring to FIG. 50, the determining device 123 includes a life storing means 124 for storing a service life of the carbon electrode 13 as an effective current amount $C_1$ which is a product $I_1 \cdot T_1$ of a certain current $I_1$ flowing across the carbon electrode 13 and a total test time $T_1$ usable when the current $I_1$ is continued to flow; a memory means 311 for storing the effective current amount $C_1$ as a remaining effective current amount $C_4$; a current measuring means (ammeter) 29 for measuring a current $I_2$ flowing across the carbon electrode 13 during a test, and a time measuring means 125 for measuring a test time $T_2$; a first calculating means $132_1$ for calculating a used current amount $C_2$ which is a product $I_2 \cdot T_2$ of the current $I_2$ and the test time $T_2$; a second calculating means 310 for subtracting the used current amount $C_2$ from the remaining effective current amount $C_4$ to provide a new remaining effective current amount and store it in the memory means 311; and a control means 312 adapted to evaluate the remaining effective current amount $C_4$ at the start of the test and to transmit an electrode replacing signal when $C_4 \leq 0$.

If the determining device 123 is constructed in the above manner, it is possible to automatically detect the timing of replacement, as the service life of the carbon electrode 13 which is a consumable electrode reaches the end.

In this case, even if the remaining effective current amount $C_4$ is smaller than 0 after the start of the test, the test is continued. This is permitted by counting on a margin of the effective current amount $C_1$ corresponding to several runs of the test.

The determining device 123 also includes a message indicating means 129 adapted to inform a testing personnel of the fact that the timing of replacement of the electrode has been reached, based on the electrode replacing signal from the control means 312, and a prohibiting means 130 for prohibiting the supplying of current to the carbon electrode 13.

As best shown in FIGS. 4 to 6, the message provided by the message indicating means 129 is displayed by characters on the liquid crystal display plate 131 mounted on the upper surface of the left cover section 52 covering the control section C as in the item [I]. The prohibiting means 130 is operated to maintain the DC power source 9 in its OFF state. Thus, the testing personnel can reliably know the timing of replacement of the carbon electrode 13.

As shown in FIG. 51, the determining device 123 is constructed so that the device 123 is not operated unless the device 123 is reset after the replacement of the electrode to bring the remaining effective current amount $C_4$ in the memory means 311 into a relation of $C_4 = C_1$.

If the remaining effective current amount $C_4$ is larger than 0 in starting the test, the test is started, and the calculation and the integration of the used current amount $C_2$ and the like are carried out.

The determining device 123 includes a remaining effective current amount indicating means 313 for indicating the remaining effective current amount $C_4$ of the carbon electrode 13. The remaining effective current amount $C_4$ indicated by the remaining effective current amount indicating means 313 is displayed in a bar graph on the liquid crystal display plate 131 such that the remaining effective current amount $C_4$ is gradually decreased, as shown in FIG. 24, as in the item [I]. Thus, the testing personnel can easily know the remainder and varying situation of the service life of the carbon electrode 13.

[Q] Other Example of Determining Device for Determining Timing of Replacement of Catalyst (FIGS. 4 to 6, 52 and 53)

Figure 52:
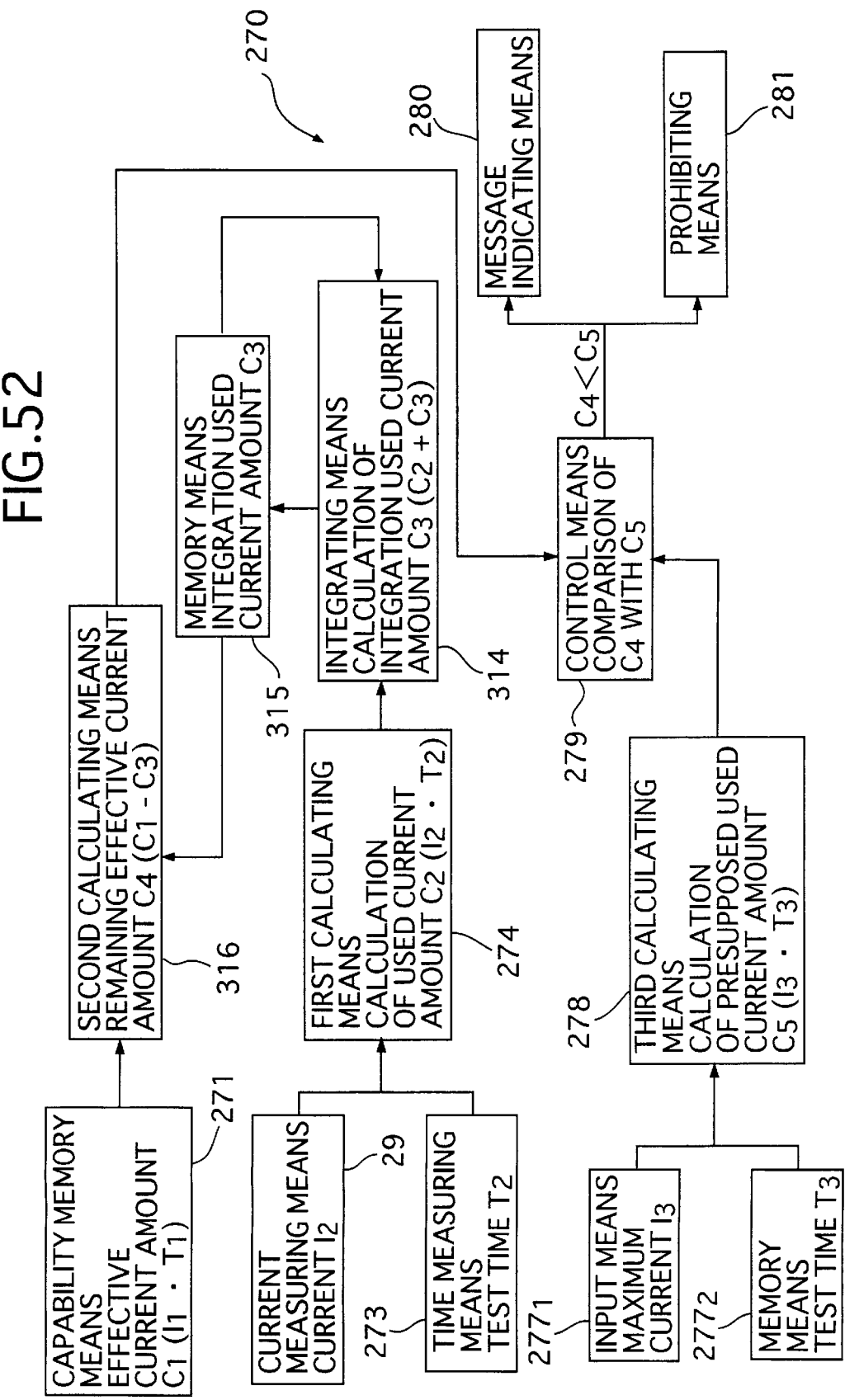
FIG. 52 is a block diagram showing the other example of a determining device for determining a timing of replacement of the catalyst.

(1) Referring to FIG. 52, the determining device 270 includes a capability storing means 271 for storing a purifying capability of an activated carbon 226 as an effective current amount $C_1$ which is a product $I_1 \cdot T_1$ of a certain current $I_1$ flowing across the carbon electrode 13 and a total test time $T_1$ usable when the current $I_1$ is continued to flow; a current measuring means (ammeter) 29 for measuring a current $I_2$ flowing across the carbon electrode 13 during a test, and a time measuring means 273 for measuring a test time $T_2$; a first calculating means 274 for calculating a used current amount $C_2$ which is a product $I_2 \cdot T_2$ Of the current $I_2$ and the test time $T_2$; an integrating means 314 for integrating the used current amount $C_2$; a memory means 315 for storing the integration used current amount $C_3$; a second calculating means 316 for subtracting the integration used current amount $C_3$ from the effective current amount $C_1$ to provide a remaining effective current amount $C_4$ of the activated carbon 226; an input means $277_1$ for inputting a maximum current $I_3$ in the DC power source 9 at the start of the test, and a memory means $277_2$ for storing a test time $T_3$; a third calculating means 278 for calculating a presupposed used current amount $C_5$ which is a product $I_3 \cdot T_3$ of the maximum current $I_3$ and the test time $T_3$; and a control means 279 adapted to compare the remaining effective current amount $C_4$ and the presupposed used current amount $C_5$ with each other and to transmit a catalyst replacing signal when $C_4 < C_5$.

If the determining device 270 is constructed in the above manner, it is possible before carrying-out of the test to automatically detect the fact that the timing of replacement of the activated carbon has been reached due to the decrease in purifying capability of the activated carbon 226.

The determining device 270 also includes a message indicating means 280 adapted to inform a testing personnel of the fact that the timing of replacement of the catalyst has been reached, based on the catalyst replacing signal from the control means 279, and a prohibiting means 281 for prohibiting the supplying of current to the carbon electrode 13.

As best shown in FIGS. 4 to 6, the message provided by the message indicating means 280 is displayed by characters on the liquid crystal display plate 131 mounted on the upper surface of the left cover section 52 covering the control section C as in the item [M], (4). The prohibiting means 281 is operated to maintain the DC power source 9 in its OFF state. Thus, the testing personnel can reliably know the timing of replacement of the activated carbon 226.

The determining device 270 is constructed such that the device 270 is not operated unless the device 270 is reset after replacement of the catalyst unit 219 to bring the integration used current amount $C_3$ in the memory means 315 into 0.

If the remaining effective current amount $C_4$ and the presupposed used current amount $C_5$ are in a relation of $C_4 \geq C_5$ in starting the test, the test is started, and the calculation of the used current amount $C_2$ and the like are carried out.

Figure 53:
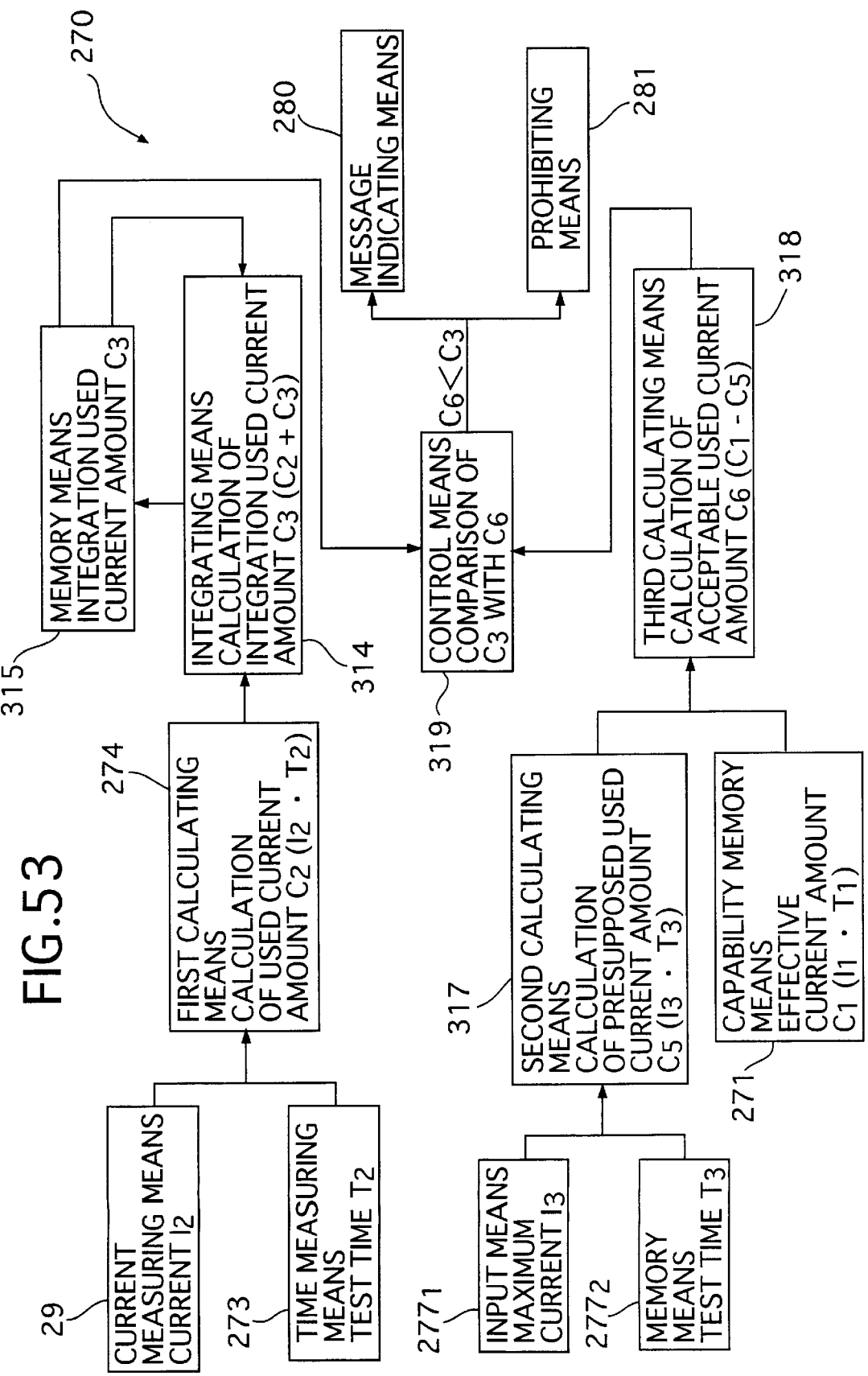
FIG. 53 is a block diagram showing a further example of a determining device for determining a timing of replacement of the catalyst.

(2) Referring to FIG. 53, the determining device 270 includes a capability storing means 271 for storing a purifying capability of an activated carbon 226 as an effective current amount $C_1$ which is a product $I_1 \cdot T_1$ of a certain current $I_1$ flowing across the carbon electrode 13 and a total test time $T_1$ usable when the current $I_1$ is continued to flow; a current measuring means (ammeter) 29 for measuring a current $I_2$ flowing across the carbon electrode 13 during a test, and a time measuring means 273 for measuring a test time $T_2$; a first calculating means 274 for calculating a used current amount $C_2$ which is a product $I_2 \cdot T_2$ of the current $I_2$ and the test time $T_2$; an integrating means 314 for integrating the used current amount $C_2$; a memory means 315 for storing the integration used current amount $C_3$; an input means 227, for inputting a maximum current $I_3$ in the DC power source 9 in the test, and a memory means $277_2$ for storing a test time $T_3$; a second calculating means 317 for calculating a presupposed used current amount $C_5$ which is a product $I_3 \cdot T_3$ of the maximum current $I_3$ and the test time $T_3$; a third calculating means 318 for subtracting the presupposed used current amount $C_5$ from the effective current amount $C_1$ to provide an acceptable used current amount $C_6$ in the activated carbon 226; and a control means 319 adapted to compare the acceptable used current amount $C_6$ and the integration used current amount $C_3$ with each other at the start of the test and to transmit a catalyst replacing signal when $C_6 < C_3$.

If the determining device 270 is constructed in the above manner, it is possible before carrying-out of the test to automatically detect the fact that the timing of replacement of the activated carbon 226 has been reached due to the decrease in purifying capability of the activated carbon 226.

The determining device 270 also includes a message indicating means 280 adapted to inform a testing personnel of the fact that the timing of replacement of the catalyst has been reached, based on the catalyst replacing signal from the control means 319, and a prohibiting means 281 for prohibiting the supplying of current to the carbon electrode 13.

As best shown in FIGS. 4 to 6, the message provided by the message indicating means 280 is displayed by characters on the liquid crystal display plate 131 mounted on the upper surface of the left cover section 52 covering the control section C as in the item [M], (4). The prohibiting means 281 is operated to maintain the DC power source 9 in its OFF state. Thus, the testing personnel can reliably know the timing of replacement of the activated carbon 226.

The determining device 270 is constructed such that the device 270 is not operated unless the device 270 is reset after replacement of the catalyst unit 219 to bring the integration used current amount $C_3$ in the memory means 315 into 0.

If the acceptable used current amount $C_6$ and the integration used current amount $C_3$ are in a relation of $C_6 \geq C_3$ in starting the test, the test is started, and the calculation of the used current amount $C_2$ and the like are carried out.

As discussed above, according to the present invention, it is possible to provide a corrosion resistance test in which the peeling-off of the coating film and the corrosion of the metal blank from the starting point provided by the damaged portion, the thinner portion, the pin hole or the like of the coating film can be promoted, whereby the overall estimation of the corrosion resistance of the test material can be performed within a short time.

In addition, according to the present invention, it is possible to provide an electrolytic test machine in which the corrosion resistance test can be easily carried out.

What is claimed is:

1. A process for promoting corrosion of a test material, comprising the steps of immersing, in an electrolytic liquid, a test material which is comprised of a metal blank and a coating film formed on said metal blank, which coating film has a damaged portion exposing a portion of a surface of the metal blank underlying said coating film, and allowing a DC current to flow between said metal blank and an electrode in said electrolytic liquid, while reversing the polarity of said metal blank alternately from positive to negative polarity and vice versa, thereby causing said coating film to be peeled off said metal blank around said damaged portion in one state of polarity and promoting corrosion of said metal blank in the reversed state of polarity.

2. The process according to claim 1, wherein the polarity of said metal blank is set at negative at the start of supplying of the current.

3. The process according to claim 2, wherein when the polarity of said metal blank is negative, the coating film peeling-off step is carried out, while when the polarity of said metal blank is positive, a metal blank corroding step is carried out, and after said coating film peeling-off step, an amount of coulomb in said metal blank corroding step is determined in accordance with a coating film peeled-off area of said metal blank.

4. The process according to claim 1, wherein when the polarity of said metal blank is negative, the coating film peeling-off step is carried out, while when the polarity of said metal blank is positive, a metal blank corroding step is carried out, and after said coating film peeling-off step, an amount of coulomb in said metal blank corroding step is determined in accordance with a coating film peeled-off area of said metal blank.

5. The process according to claim 1, wherein for said DC current an applied voltage is set at at least about 5.5 V.

6. The process according to claim 1, wherein for said DC current an applied voltage is set at least about 8 V.

7. The process according to claim 1, wherein said metal blank is entirely enclosed by said coating film.

8. A process for promoting corrosion of a test material, comprising the steps of immersing, in an electrolytic liquid, a test material which is comprised of a metal blank and a coating film formed on said metal blank, and allowing a DC current to flow between said metal blank and an electrode in said electrolytic liquid while reversing the polarity of said metal blank alternately from positive to negative and vice versa, thereby causing said coating film to be at least partly peeled off said metal blank in one state of polarity and promoting corrosion of said metal blank in the reversed state of polarity.

9. The process according to claim 8, wherein the polarity of said metal blank is set at negative at the start of supplying of the current.

10. The process according to claim 8, wherein when the polarity of said metal blank is negative, the coating film peeling-off step is carried out, while when the polarity of said metal blank is positive, a metal blank corroding step is carried out, and after said coating film peeling-off step, an amount of coulomb in said metal blank corroding step is determined in accordance with a coating film peeled-off area of said metal blank.

11. The process according to claim 8, wherein for said DC current an applied voltage is set at at least about 5.5 V.

12. The process according to claim 8, wherein for said DC current an applied voltage is set at at least about 8 V.

13. The process according to claim 8, wherein said metal blank is entirely enclosed by said coating film.

* * * * *